US009932577B2

(12) United States Patent
Piepenburg et al.

(10) Patent No.: US 9,932,577 B2
(45) Date of Patent: *Apr. 3, 2018

(54) METHODS FOR MULTIPLEXING RECOMBINASE POLYMERASE AMPLIFICATION

(71) Applicant: Alere San Diego, Inc., San Diego, CA (US)

(72) Inventors: Olaf Piepenburg, Hertfordshire (GB); Colin H. Williams, London (GB); Niall A. Armes, Essex (GB)

(73) Assignee: ALERE SAN DIEGO, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/066,334

(22) Filed: Oct. 29, 2013

(65) Prior Publication Data

US 2014/0295436 A1 Oct. 2, 2014

Related U.S. Application Data

(63) Continuation of application No. 13/177,007, filed on Jul. 6, 2011, now Pat. No. 8,580,507, which is a continuation of application No. 11/988,825, filed as application No. PCT/IB2006/004113 on Jul. 25, 2006, now Pat. No. 8,062,850.

(60) Provisional application No. 60/702,533, filed on Jul. 25, 2005, provisional application No. 60/728,424, filed on Oct. 18, 2005.

(51) Int. Cl.
| | | |
|---|---|---|
| C12Q 1/68 | (2018.01) | |
| C12N 15/113 | (2010.01) | |
| G01N 21/78 | (2006.01) | |
| G01N 33/558 | (2006.01) | |
| G01N 21/77 | (2006.01) | |

(52) U.S. Cl.
CPC .......... *C12N 15/113* (2013.01); *C12Q 1/6804* (2013.01); *C12Q 1/6816* (2013.01); *C12Q 1/6827* (2013.01); *C12Q 1/6844* (2013.01); *C12Q 1/6853* (2013.01); *G01N 21/78* (2013.01); *G01N 33/558* (2013.01); *G01N 2021/7759* (2013.01); *G01N 2021/7763* (2013.01); *G01N 2021/7793* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,965,188 A | 10/1990 | Mullis et al. |
| 5,223,414 A | 6/1993 | Zarling et al. |
| 5,273,881 A | 12/1993 | Sena et al. |
| 5,326,692 A | 7/1994 | Brinkley |
| 5,354,668 A | 10/1994 | Auerbach |
| 5,418,149 A | 5/1995 | Gelfand et al. |
| 5,430,136 A | 7/1995 | Urdea et al. |
| 5,455,166 A | 10/1995 | Walker |
| 5,536,649 A | 7/1996 | Fraiser et al. |
| 5,556,751 A | 9/1996 | Stefano |
| 5,591,609 A | 1/1997 | Auerbach |
| 5,614,389 A | 3/1997 | Auerbach |
| 5,635,347 A | 6/1997 | Link et al. |
| 5,656,430 A | 8/1997 | Chirikjian |
| 5,665,572 A | 9/1997 | Ikeda et al. |
| 5,670,316 A | 9/1997 | Sena et al. |
| 5,705,366 A | 1/1998 | Backus |
| 5,712,124 A | 1/1998 | Walker |
| 5,731,150 A | 3/1998 | Sandhu et al. |
| 5,733,733 A | 3/1998 | Auerbach |
| 5,744,311 A | 4/1998 | Fraiser et al. |
| 5,792,607 A | 8/1998 | Backman et al. |
| 5,834,202 A | 11/1998 | Auerbach |
| 5,849,547 A | 12/1998 | Cleuziat |
| 5,858,652 A | 1/1999 | Laffler et al. |
| 5,916,779 A | 6/1999 | Pearson et al. |
| 5,942,391 A | 8/1999 | Zhang et al. |
| 6,087,112 A | 7/2000 | Dale |
| 6,140,054 A | 10/2000 | Wittwer et al. |
| 6,165,793 A | 12/2000 | Stemmer |
| 6,251,600 B1 | 6/2001 | Winger et al. |
| 6,379,899 B1 | 4/2002 | Ullman |
| 6,387,621 B1 | 5/2002 | Wittwer |
| 6,448,065 B2 | 9/2002 | Laugharn, Jr. et al. |
| 6,509,157 B1 | 1/2003 | Martinez |
| 6,566,103 B2 | 5/2003 | Wijnhoven et al. |

(Continued)

FOREIGN PATENT DOCUMENTS

| | | |
|---|---|---|
| CA | 2444649 | 10/2002 |
| CA | 2476481 | 9/2003 |

(Continued)

OTHER PUBLICATIONS

Greco, NJ. et al. Simple fluorescent pyrimidine analogues detect the presence of DNA absic sites. JACS, vol. 127, p. 10784-10785, 2005.*
Extended European Search Report in corresponding Application No. 14170595.4, dated Jan. 7, 2015, pp. 1-5.
Office Action in corresponding Japanese Patent Application No. 2012-086528, dated Mar. 20, 2014, pp. 1-6.
Notice of Reasons for Rejection in corresponding Application No. JP2012-209422, dated Mar. 3, 2015, pp. 1-15.
Tetart et al., "Phylogeny of the Major Head and Tail Genes of the Wide-Ranging T4-Type Bacteriophages," Journal of Bacteriology, vol. 183(1):358-366 (2001).
Gill et al., "Nucleic acid isothermal amplification technologies: a review," Nucleosides Nucleotides Nucleic Acids 2008 27:224-243.

(Continued)

*Primary Examiner* — Prabha Chunduru
(74) *Attorney, Agent, or Firm* — Casimir Jones, S.C.

(57) ABSTRACT

This disclosure provides for methods and reagents for rapid multiplex RPA reactions and improved methods for detection of multiplex RPA reaction products. In addition, the disclosure provides new methods for eliminating carryover contamination between RPA processes.

9 Claims, 16 Drawing Sheets

(56) References Cited

U.S. PATENT DOCUMENTS

| | | | |
|---|---|---|---|
| 6,699,693 B1 | 3/2004 | Marians et al. | |
| 6,929,915 B2 | 8/2005 | Benkovic et al. | |
| 7,112,423 B2 | 9/2006 | Van Ness et al. | |
| 7,252,940 B2 | 8/2007 | Kutyavin et al. | |
| 7,270,981 B2 | 9/2007 | Armes et al. | |
| 7,282,328 B2 | 10/2007 | Kong | |
| 7,399,590 B2 | 7/2008 | Piepenburg et al. | |
| 7,435,561 B2 | 10/2008 | Piepenburg et al. | |
| 7,485,428 B2 | 2/2009 | Armes et al. | |
| 7,666,598 B2 | 2/2010 | Piepenburg et al. | |
| 7,763,427 B2 | 7/2010 | Piepenburg et al. | |
| 7,777,958 B2 | 8/2010 | Shimmo et al. | |
| 8,017,339 B2 | 9/2011 | Piepenburg et al. | |
| 8,030,000 B2* | 10/2011 | Piepenburg | C12Q 1/6844 435/6.12 |
| 8,062,850 B2 | 11/2011 | Piepenburg et al. | |
| 8,071,308 B2 | 12/2011 | Piepenburg et al. | |
| 8,426,134 B2 | 4/2013 | Piepenburg et al. | |
| 8,431,347 B2* | 4/2013 | Millar et al. | 435/6.12 |
| 8,574,846 B2 | 11/2013 | Piepenburg et al. | |
| 8,945,845 B2 | 2/2015 | Piepenburg et al. | |
| 8,962,255 B2 | 2/2015 | Piepenburg et al. | |
| 2001/0044111 A1 | 11/2001 | Carr et al. | |
| 2002/0061530 A1 | 5/2002 | Belotserkovskii et al. | |
| 2002/0155573 A1 | 10/2002 | Lanes et al. | |
| 2003/0082565 A1 | 5/2003 | Jang | |
| 2003/0082590 A1 | 5/2003 | Van Ness et al. | |
| 2003/0108936 A1 | 6/2003 | Wagner | |
| 2003/0119150 A1* | 6/2003 | Ankenbauer | C12Q 1/6848 435/91.2 |
| 2003/0138800 A1 | 7/2003 | Van Ness et al. | |
| 2003/0143525 A1 | 7/2003 | Benkovic et al. | |
| 2003/0219792 A1 | 11/2003 | Armes et al. | |
| 2003/0228611 A1 | 12/2003 | Chruch et al. | |
| 2004/0038213 A1 | 2/2004 | Kwon | |
| 2004/0058378 A1 | 3/2004 | Kong et al. | |
| 2004/0067559 A1* | 4/2004 | McCarthy | C12Q 1/682 435/91.2 |
| 2004/0091864 A1* | 5/2004 | French et al. | 435/6 |
| 2004/0101893 A1* | 5/2004 | Kutyavin et al. | 435/6 |
| 2004/0137456 A1 | 7/2004 | Yokota et al. | |
| 2004/0224336 A1 | 11/2004 | Wagner | |
| 2005/0003395 A1 | 1/2005 | Gellibolian et al. | |
| 2005/0059003 A1 | 3/2005 | Enoki et al. | |
| 2005/0112631 A1* | 5/2005 | Piepenburg et al. | 435/6 |
| 2005/0136443 A1 | 6/2005 | Shigemori | |
| 2006/0110765 A1 | 5/2006 | Wang | |
| 2006/0154286 A1 | 7/2006 | Kong et al. | |
| 2007/0031869 A1 | 2/2007 | McCoy et al. | |
| 2007/0042427 A1 | 2/2007 | Gerdes et al. | |
| 2007/0054296 A1 | 3/2007 | Piepenburg | |
| 2007/0154914 A1 | 7/2007 | Gelfand et al. | |
| 2007/0259348 A1 | 11/2007 | Phadke et al. | |
| 2008/0076160 A1 | 3/2008 | Armes et al. | |
| 2008/0293045 A1 | 11/2008 | Piepenburg et al. | |
| 2009/0017453 A1 | 1/2009 | Maples et al. | |
| 2009/0017462 A1 | 1/2009 | Piepenburg et al. | |
| 2009/0029421 A1 | 1/2009 | Piepenburg et al. | |
| 2009/0081670 A1 | 3/2009 | Maples et al. | |
| 2009/0269813 A1 | 10/2009 | Piepenburg et al. | |
| 2009/0325165 A1 | 12/2009 | Armes et al. | |
| 2010/0234245 A1 | 9/2010 | McGee et al. | |
| 2010/0311127 A1 | 12/2010 | Piepenburg et al. | |
| 2011/0053153 A1 | 3/2011 | Piepenburg et al. | |
| 2011/0059506 A1 | 3/2011 | Piepenburg et al. | |
| 2011/0065106 A1 | 3/2011 | Armes et al. | |
| 2012/0015367 A1 | 1/2012 | Piepenburg et al. | |
| 2012/0021462 A1 | 1/2012 | Armes et al. | |
| 2012/0058517 A1 | 3/2012 | Piepenburg et al. | |
| 2012/0082990 A1 | 4/2012 | Piepenburg et al. | |
| 2012/0129173 A1 | 5/2012 | Piepenburg et al. | |
| 2014/0099674 A1 | 4/2014 | Piepenburg et al. | |
| 2014/0141434 A1 | 5/2014 | Armes et al. | |
| 2014/0234846 A1 | 8/2014 | Piepenburg et al. | |
| 2014/0295436 A1 | 10/2014 | Piepenburg et al. | |

FOREIGN PATENT DOCUMENTS

| | | |
|---|---|---|
| EP | 0 624 643 | 4/1994 |
| EP | 0 702 090 | 3/1996 |
| EP | 0 810 436 | 12/1997 |
| EP | 1403379 | 3/2004 |
| EP | 1 420 069 | 5/2004 |
| EP | 1 564 306 | 8/2005 |
| JP | 2002-512044 | 4/2002 |
| JP | 2004-512843 | 4/2004 |
| JP | 2008-515447 | 5/2008 |
| JP | 2009-502161 | 1/2009 |
| JP | 2011-505127 | 2/2011 |
| WO | WO 91/17267 | 11/1991 |
| WO | WO 93/05178 | 3/1993 |
| WO | WO 97/20078 | 6/1997 |
| WO | WO 98/08975 | 3/1998 |
| WO | WO99/60158 | 11/1999 |
| WO | WO 99/60158 | 11/1999 |
| WO | WO 00/41524 | 7/2000 |
| WO | WO 00/46408 | 8/2000 |
| WO | WO 02/086167 | 10/2002 |
| WO | WO 03/027640 | 4/2003 |
| WO | WO 03/038053 | 5/2003 |
| WO | WO 03/072805 | 9/2003 |
| WO | WO 04/007078 | 1/2004 |
| WO | WO 04/027025 | 4/2004 |
| WO | WO 04/090169 | 10/2004 |
| WO | WO 05/118853 | 12/2005 |
| WO | WO06/040187 | 4/2006 |
| WO | WO 06/040187 | 4/2006 |
| WO | WO 07/096702 | 8/2007 |
| WO | WO2010141940 | 12/2010 |
| WO | WO2013185081 | 12/2013 |

OTHER PUBLICATIONS

Mukai et al., "Highly efficient isothermal DNA amplification system using three elements of 5'-DNA-RNA-3' chimeric primers, RNaseH and strand-displacing DNA polymerase," 2007, J. Biochem. 142:273-281.

Tan et al., "Isothermal DNA amplification coupled with DNA nanosphere-based colorimetric detection," Anal. Chem. 2005, 77:7984-7992.

Lizard et al., Nature Biotech. 1998, 6:1197-1202.

Mori et al., "Loop-mediated isothermal amplification (LAMP): a rapid, accurate, and cost-effective diagnostic method for infectious diseases," J. Infect. Chemother. 2009 15:62-69.

Kurn et al., "Novel isothermal, linear nucleic acid amplification systems for highly multiplexed applications," Clin. Chem. 2005, 51:10, 1973-1981.

Piekarowicz et al., "Characterization of the dsDNA prophage sequences in the genome of Neisseria gonorrhoeae and visualization of productive bacteriophage," 2007, BMC Microbiol., 7:66.

Liu et al., 2005, "Rapid identification of Streptococcus pyogenes with PCR primers from a putative transcriptional regulator gene," Res. Microbiol., 156:564-567.

Podbielski et al., Molecular characterization of the cfb gene encoding group B streptococcal CAMP-factor, 1994, Med. Microbiol. Immunol., 183:239-256.

Schoenmakers et al., 1992, Biotechniques, 12:870-874.

Fujishiro et al., 1995, Comput. Biol. Med., 25:61-80.

Bahador et al., 2005, Res. J. Agr. Biol. Sci. 1;142-145.

International Search Report and Written Opinion in corresponding Application No. PCT/US13/44796, dated Nov. 8, 2013, pp. 1.

El-Harakany AA et al., "Dissociation Constants and Related Thermodynamic Quantities of the Protonated Acid Form of Tris-(Hydroxymethyl)-Aminomethane in Mixtures of 2-Methoxyethanol and Water at Different Temperatures," Journal of Electroanalytical Chemistry:162:285-305 & 296 (1984).

Granholm K. et al., "Desorption of Metal Ions from Kraft Pulps. Part 1. Chelation of Hardwood and Softwood Kraft Pulp With EDTA," Bioresources:5(1)206-226 (2010).

Response to the Article 94 in EP Application No. 11184367.8, dated Oct. 23, 2013, pp. 1-12.

(56) References Cited

OTHER PUBLICATIONS

Reddy et al., Joints Made by RecA Protein in the Interior of Linear Duplex DNA: Effects of Single-Stranded Ends, Length of Homology, and Dynamic State, *Biochemistry*, 33:11486-11492 (1994).
Office Action from corresponding Japanese Application No. 2012-511958, dated Oct. 3, 2014, pp. 1-5.
English translation of Office Action from corresponding Japanese Application No. 2012-511958, dated Oct. 3, 2014, pp. 1-5.
Office Action in corresponding EP Application No. 10180482.1, dated May 30, 2014, pp. 1-5.
Adams et al., "Dissociation of RecA filaments from duplex DNA by the RuvA and RuvB DNA repair proteins," Proc. Natl. Acad. Sci. USA 91:9901-9905, 1994.
Alexseyev et al., "Genetic Characteristics of New recA Mutants of *Escherichia coli* K-12," J. Bacteriol., 178:2018-2024, 1996.
Amasino, "Acceleration of Nucleic Acid Hybridization Rate by Polyethylene Glycol," Anal. Biochem., 152:304-307, 1986.
Bains and Smith, "A Novel Method for Nucleic Acid Sequence Determination," J. Theor. Biol., 135:303-307, 1988.
Bar-Ziv and Libchaber, "Effects of DNA sequence and structure on binding of RecA to single-stranded DNA," PNAS USA, 98(16):9068-9073.
Baumann et al., "Purification of human Rad51 protein by selective spermidine precipitation," Mutat. Res., 384:65-72, 1997.
Benedict and Kowalczykowski, "Increase of the DNA Strand Assimiliation Activity of recA Protein by Removal of the C Terminus and Structure-Function Studies of the Resulting Protein Fragment," J. Biol. Chem., 263(30):15513-15520, 1988.
Benkovic et al., "Replisome-Mediated DNA Replication," Annu. Rev. Biochem., 70:181-208, 2001.
Bennett and Holloman, "A RecA Homologue in Ustilago maydis That is Distinct and Evolutionarily Distant from Rad51 Actively Promotes DNA Pairing Reactions in the Absence of Auxiliary Factors," Biochemistry, 40:2942-2953, 2001.
Better and Helinski, "Isolation and Characterization of the recA Gene of Rhizobium meliloti," J. Bacteriol, 155:311-316, 1983.
Bianco and Weinstock, "Interaction of the RecA protein of *Escherichia coli* with single-stranded oligodeoxyribonucleotides," Nucleic Acids Research, 24(24):4933-4939, 1996.
Bianco et al., "DNA Strand Exchange Proteins: A Biochemical and Physical Comparison," Frontiers in Bioscience, 3:D570-D603, 1998.
Borjac-Natour et al., "Divergence of the mRNA targets for the Ssb proteins of bacteriophages T4 and RB69," Virology J., 1(4):1-14, 2004.
Bork et al., "The RecOR proteins modulate RecA protein function at 5' ends of single-stranded DNA," EMBO J., 20:7313-7322, 2001.
Bork et al., "RecA Protein Filaments Disassemble in the 5' to 3' Direction on Single-stranded DNA," J. Biol. Chem., 276:45740-45743, 2001.
Butler et al., "Investigating Structural Changes Induced by nucleotide Binding to RecA Using Difference FTIR," Biophysical J., 82(4):2198-2210, 2002.
Byrd and Raney, "Protein displacement by an assembly of helicase molecules aligned along single-stranded DNA," Nat. Struct. Mol. Biol., 11(6):531-538, 2004.
Chan et al., "Effects of Polyethylene Glycol on Reverse Transcriptase and Other polymerase Activities," Biochim. Biophys. Acta., 606(2):353-361, 1980.
Compton, "Nucleic acid sequence-based amplification," Nature, 350:91-92, 1991.
Cox et al., "The importance of repairing stalled replication forks," Nature, 404:37-41, 2000.
Cox et al., "A Simple and Rapid Procedure for the Large Scale Purification of the recA protein of *Escherichia coli*," J. Biol. Chem., 256:4676-4678, 1981.
Cromie and Leach, "Control of Crossing Over," Mol. Cell., 6:815-826. 2000.

Decker et al., "In Vitro Initiation of DNA Replication in Simian Virus 40 Chromosomes," J. Biol. Chem., 262(22):10863-10872, 1987.
Demidov, "Rolling-circle amplification in DNA diagnostics: the power of simplicity," Expert Rev. Mol. Diagn., 2(6):89-95, 2002.
Digard et al., "The Extreme C Terminus of Herpes Simplex Virus DNA Polymerase is Crucial for Functional Interaction with Processivity Factor UL42 and for Viral Replication," J. Virol., 67(1):398-406, 1993.
Dillingham and Kowalczykowski, "A Step Backward in Advancing DNA Replication: Rescue of Stalled Replication Forks by RecG," Mol. Cell., 8:734-736, 2001.
Dong et al., "A coupled complex of T4 DNA replication helicase (gp41) and polymerase (gp43) can perform rapid and processive DNA strand-displacement synthesis," Proc. Natl. Acad. Sci. USA, 93:14456-14461, 1996.
Drmanac, et al., "Sequencing of Megabase Plus DNA by Hybridization: Theory of the Method," Genomics, 4:114-128, 1989.
Edwards et al., "Genetic Variation at Five Trimeric and Tetrameric Tandem Repeat Loci in Four Human Population Groups," Genomics, 12:241-253, 1992.
Eggler et al., "The C Terminus of the *Escherichia coli* RecA Protein Modulates the DNA Binding Competition with Single-stranded DNA-binding Protein," J. Biol. Chem., 278:16389-16396, 2003.
Eggleston and West, "Cleavage of Holliday Junctions by the *Escherichia coli* RuvABC Complex," J. Biol. Chem., 275:26467-26476, 2000.
Elias-Arnanz and Salas, "Bacteriophage ø29 DNA replication arrest caused by codirectional collisions with the transcription machinery," EMBO J., 16:5775-5783, 1997.
Ellis, "Macromolecular crowding: obvious but underappreciated," Trends in Biochem. Sci., 26(10):597-604, 2001.
Ellouze et al., "Evidence for elongation of the helical pitch of the RecA filament upon ATP and ADP binding using small-angle neutron scattering," Eur. J. Biochem., 23392):579-583, 1995.
Enright et al., The evolutionary history of methicillin-resistant *Staphylococcus aureus* (MRSA), Proc. Natl. Acad. Sci. USA, 99:7687-7692, 2002.
Fahy et al., "Self-sustained sequence replication (3SR): an isothermal transcription-based amplification system alternative to PCR," Genome Res, 1:25-33, 1991.
Ferrari et al., "Co-operative Binding of *Escherichia coli* SSB Tetramers to Single-stranded DNA in the $(SSB)_{35}$ Binding Mode," J. Mol. Biol, 236:106-123, 1994.
Formosa et al., "Affinity purification of bacteriophage T4 proteins essential for DNA replication and genetic recombination," Proc. Natl. Acad. Sci. USA, 80:2442-2446, 1983.
Formosa and Alberts, "Purification and Characterization of the T4 Bacteriophage uvsX Protein," J. Biol. Chem., 261:6107-6118, 1986.
Formosa and Alberts, "DNA Synthesis Dependent on Genetic Recombination: Characterization of a Reaction Catalyzed by Purified Bacteriophage T4 Proteins," Cell, 47:793-806, 1986.
Fu et al., "Dynamics of DNA-tracking by two sliding-clamp proteins," EMBO J., 15(16):4414-4422, 1996.
Fuller et al., "Enzymatic replication of the origin of the *Escherichia coli* chromosome," Proc. Natl. Acad. Sci. USA, 78(12):7370-7374, 1981.
Giedroc et al., "The Function of Zinc in Gene 32 Protein from T4," Biochem., 26:5251-5259, 1987.
Giedroc et al., "Zn(II) Coordination Domain Mutants of T4 Gene 32 protein," Biochem., 31:765-774, 1992.
Ginocchio, "Life Beyond PCR: Alternative Target Amplification Technologies for the Diagnosis of Infectious Diseases, Part II," Clin. Microbiol. Newsletter, 26(17):129-136, 2004.
Glover and McHenry, "The DNA Polymerase III Holoenzyme: An Asymmetric Dimeric Replicative Complex with Leading and Lagging Strand Polymerases," Cell., 105:925-934.
Goodman et al., "Cloning and expression in *Escherichia coli* of a recA-like gene from *Bacteroides fragilis*," Gene, 58:265-271, 1987.
Hacker and Alberts, "Overexpression, Purification, Sequence Analysis, and Characterization of the T4 Bacteriophage dda DNA Helicase," J. Biol. Chem., 267:20674-20681, 1992.

(56) References Cited

OTHER PUBLICATIONS

Hammond et al., "Evaluation of 13 Short Tandem Repeat Loci for Use in Personal Identification Applications," Am. J. Hum. Genetics, 55:175-189, 1994.
Harris and Griffith, "UvsY Protein of Bacteriophage T4 is an Accessory Protein for in Vitro Catalysis of Strand Exchange," J. Mol. Biol., 206:19-27, 1989.
Harris and Griffith, "Visualization of the Homologous Pairing of DNA Catalyzed by the Bacteriophage T4 UvsX Protein," J. Biol. Chem., 262:9285-9292, 1987.
Harris and Griffith, "Formation of D Loops by the UvsX Protein of T4 Bacteriophage: A Comparison of the Reaction Catalyzed in the Presence or Absence of Gene 32 Protein," Biochem., 27:6954-6959, 1988.
Harvey et al., "Characterization and applications of CataCleave probe in real-time detection assays," Anal. Biochem., 333(2):246-255, 2004.
Heid et al., "Real time quantitative PCR," Genome Res., 6(10):986-994, 1996.
Heyer and Kolodner, "Purification and Characteirzation of a Protein from *Saccharomyces cerevisiae* That Binds Tightly to Single-Stranded DNA and Stimulates a cognate Strand Exchange Protein," Biochem. 28:2856-2862, 1989.
Hickson et al., "A Temperature Sensitive RecA Protein of *Escherichia coli*," Mol. Gen. Genet., 184:68-72, 1981.
Hopp et al., "A Short Polypeptide Marker Sequence Useful for Recombinant Protein Identification and Purification," Biotech., 6:1204-1210, 1988.
Hsieh et al., "The synapsis event in the homologous pairing of DNAs: RecA recognizes and pairs less than one helical repeat of DNA," Proc. Natl. Acad. Sci. USA, 89:6492-6496, 1992.
Huletsky et al., "New Real-Time PCR Assay for Rapid Detection of Methicillin-Resistant *Staphylococcus aureus* Directly from Specimens Containing a Mixturre of Staphylococci," J. Clin. Microbiol., 42:1875-1884, 2004.
Ischenko and Saparbaev, "Alternative nucleotide incision repair pathway for oxidative DNA damage," Nature, 415(6868):183-187, 2002.
Jarvis et al., "'Macromolecular Crowding': Thermodynamic Consequences for Protein-Protein Interactions with in the T4 DNA Replication Complex," J. Biol. Chem., 265(25):15160-15167, 1990.
Kaboord and Benkovic, "Rapid assembly of the bacteriophage T4 core replication complex on a linear primer/template construct," Proc. Natl. Acad. Sci. USA, 90:10881-10885, 1993.
Kaiser et al., "A Comparison of Eubacterial and Archaeal Structure-specific 5'-Exonucleases," J. Biol. Chem., 274(30):21387-21394, 1999.
Kato and Kuramitsu, "RecA Protein from an Extremely Thermophilic Bacterium, Thermus thermophiles HB8," J. Biochem., 114:926-929, 1993.
Katz and Bryant, "Interdependence of the Kinetics of NTP Hydrolysis and the Stability of the RecA-ssDNA Complex," Biochem., 40:11082-11089, 2001.
Kelman and O'Donnell, "DNA Polymerase III Holoenzyme: Structure and Function of a Chromosomal Replicating Machine," Annu. Rev. Biochem., 64:171-2000.
Khrapko et al., "An oligonucleotide hybridization approach to DNA sequencing," FEBS Lett., 256:118-122, 1989.
Komori et al., "Both RadA and RadB are Involved in Homologous Recombination in *Pyrococcus furiosus*," J. Biol. Chem., 275:33782-33790, 2000.
Kowalczykowski et al., "Effects of the *Escherichia coli* SSB Protein on the Binding of *Escherichia coli* RecA Protein to Single-stranded DNA—Demonstration of Competitive Binding and the Lack of a Specific Protein-Protein Interaction," J. Mol. Biol., 193:81-95, 1987.
Kuil et al., "The internal dynamics of gene 32 protein-DNA complexes studied by quasi-elastic light scattering," Biophys. Chem., 32:211-227, 1988.
Kuil et al., "A Refined Calculation of the Solution Dimensions of the Complex Between gene 32 Protein and Single Stranded DNA Based on Estimates of the Bending Persistence Length," J. Biomol. Struct. Dyn. 7(4):943-957, 1990.
Kuramitsu et al., "A Large-Scale Preparation and Some Physicochemical Properties of RecA Protein," J. Biochem., 90:1033-1045, 1981.
Kurumizaka et al., "A Chimeric RecA Protein Exhibits Altered Double-stranded DNA Binding," J. Biol. Chem., 269:3068-3075, 1994.
Lavery and Kowalczykowski, "Enhancement of recA Protein-promoted DNA Strand Exchange Activity by Volume-occupying Agents," J. Biol. Chem., 267:9301-9314, 1992.
Lavery and Kowalczykowski, "A Postsynaptic Role for Single-stranded DNA-binding Protein in recA Protein-promoted DNA Strand Exchange," J. Biol. Chem., 267(13):9315-9320, 1992.
LeBowitz and McMacken, "The bacteriophage λ O and P protein initiators promote the replication of single-stranded DNA," 12(7):1-20, 1984.
Lerman, "A Transition to a Compact Form of DNA in Polymer Solutions," Proc. Nat. Acad. Sci. USA, 68(8):1886-1890, 1971.
Levin et al., "Homogeneous *Escherichia coli* Endonuclease IV," J. Biol. Chem., 263:8066-8071, 1988.
Liu et al., "The Ordered Assembly of the øX174-type Primosome," J. Biol. Chem., 271:15656-15661, 1996.
Lohman and Ferrari, "*Escherichia coli* Single-Stranded DNA-Binding Protein: Multiple DNA-Binding Modes and Cooperativities," Annu. Rev. Biochem., 63:527-570, 1994.
Lovett and Roberts, "Purification of a RecA Protein Analogue from *Bacillus subtilis*," J. Biol. Chem., 260:3305-3313, 1985.
Lusetti et al., "Magnesium Ion-dependent Activation of the RecA Protein Involves the C Terminus," J. Biol. Chem., 278(18):16381-16388, 2003.
Lutz-Freyermuth et al., "Quantitative determination that one of two potential RNA-binding domains of the A protein component of the U1 small nuclear ribonuclearprotein complex binds with high affinity to stem-loop II of U1 RNA," Proc. Natl. Acad. Sci. USA, 87:6393-6397, 1990.
Lysov et al., "Establishing Nucleotide Sequence of DNA using Oligonucleotide Hydridization. Novel Method," SSSR 303:1508-1511, 1988 (English translation).
Maeshima et al., "Purification and characterization of XRad51.1 protein, Xenopus RAD51 homologue: recombinant XRad51.1 promotes strand exchange reaction," Genes Cells, 1:1057-1068, 1996.
Maki et al., "DNA Polymerase III Holoenzyme of *Escherichia coli*," J. Biol. Chem., 263(14):6570-6578, 1988.
Malkov and Camerini-Otero, Photocross-links between Single-stranded DNA and *Escherichia coli* RecA Protein Map to Loops L1 (Amino Acid Residues 157-164) and L2 (Amino Acid Residues 195-209),: J. Biol. Chem., 270(50):30230-30233, 1995.
Marians, "Prokaryotic DNA Replication," Annu. Rev. Biochem., 61:673-719, 1992.
Marians, "PriA: At the Crossroads of DNA Replication and Recombination," Prog. Nucleic Acid Res. Mol. Biol., 63:39-67, 1999.
Marras et al., "Multiplex detection of single-nucleotide variations using molecular beacons," Genet. Anal. Biomolec. Eng., 14:151-156, 1999.
Martin et al., "GAP Domains Responsible for Ras p21-Dependent Inhibition of Muscarinic Atrial $K^+$ $^C$hannel Currents," Science, 255:192-194, 1992.
Maxam and Gilbert, "A new method for sequencing DNA," Proc. Natl. Acad. Sci. USA, 74:560-564, 1877.
Mazin and Kowalczykowski, "The function of the secondary DNA-binding site of RecA protein during DNA strand exchange," Proc. Natl. Acad. Sci. USA, 74:560-564, 1977.
McGlynn and Lloyd, "RecG helicase activity at three- and four-strand DNA structures," Nucl. Acid Res., 27:3049-3056, 1999.
McGlynn et al., "Characterisation of the catalytically active form of RecG helicase," Nucl. Acid Res., 28:2324-2332, 2000.
Minton, "The Influence of Macromolecular Crowding and Macromolecular Confinement on Biochemical Reactions in Physiological Media," J. Biol. Chem., 276(14):10577-10580, 2001.

(56) References Cited

OTHER PUBLICATIONS

Mitra and Church, "In situ localized amplification and contact replication of many individual DNA molecules," Nucl. Acids Res., 27(24):e34i-e34vi.
Mizuuchi, "In Vitro Transposition of Bacteriophage Mu: A Biochemical Approach to a Novel Replication Reaction," Cell, 35:785-794, 1983.
Morel et al., "Recombination-dependent Repair of DNA Double-strand Breaks with Purified Proteins from *Escherichia coli*," J. Biol. Chem., 272:17091-17096, 1997.
Morrical et al., "Amplification of Snap-back DNA Synthesis Reactions by the uvsX Recombinase of Bacteriophage T4," J. Biol. Chem., 266:14031-14038, 1991.
Morrical and Alberts, "The UvsY Protein of Bacteriophage T4 Modulates Recombination-dependent DNA Synthesis in Vitro," J. Biol. Chem., 265:15096-15103, 1990.
Morris and Raney, "DNA Helicases Displace Streptavidin from Biotin-Labeled Oligonucleotides," Biochem., 38(16):5164-5171, 1999.
Morrison et al., "Quantificationo f Low-Copy Transcripts by Continuous SYBR Green I Monitoring during Amplification," BioTechniques, 24:954-962, 1998.
Nadler et al., "A Novel Function for Zinc(II) in a Nucleic Acid-binding Protein," J. Biol. Chem., 265(18):10389-10394, 1990.
Nadeau et al., "Real-Time, Sequence-Specific Detection of Nucleic Acids during Strand Displacement Amplification," Anal. Biochem., 276(2):177-187, 1999.
Naimushin et al., "Effect of Polyethylene Glycol on the Supercoiling Free Energy of DNA," Biopolymers, 58(2):204-217, 2001.
Ng and Marians, "The Ordered Assembly of the øX174-type Primosome," J. Biol. Chem., 271:15642-15648, 1996.
Ng and Marians, "The Ordered Assembly of the øX174-type Primosome," J. Biol. Chem., 271:15649-15655, 1996.
Okazaki and Kornberg, "Enzymatic Synthesis of Deoxyribonucleic Acid," J. Biol. Chem., 239:259-268, 1964.
Paulus and Bryant, "Time-Dependent Inhibition of recA Protein-Catalyzed ATPHydrolysis by ATPγS: Evidence for a Rate-Determining Isomerization of the recA-ssDNA Complex," Biochem., 36:7832-7838, 1997.
Pevzner, "1-Tuple DNA Sequencing: Computer Analysis," J. Biomol. Struct. Dyn., 7:63-73, 1989.
Pham et al., "A model for SOS-lesion-targeted mutations in *Escherichia coli*," Nature, 409:366-370, 2001.
Piepenburg et al., "DNA Detection Using Recombination Proteins," PLOS Biology, 4(7):1115-1121, 2006.
Pierre and Paoletti, "Purification and Characterization of recA Protein from *Salmonella typhimurium*," J. Biol. Chem., 258:2870-2874, 1983.
Podust et al., "Replication Factor C Disengages from Proliferating Cell Nuclear Antigen (PCNA) upon Sliding Clamp Formation, and PCNA Itself Tethers DNA Polymerase δ to DNA," J. Biol. Chem., 273(48):31992-31999, 1998.
Pomp and Medrano, "Organic Solvents as Facilitators of Polymerase chain Reaction," Biotechniques, 10(1):58-59, 1991.
Qiu and Giedroc, "Effects of Substitution of Proposed Zn(II) Ligand His[81] or His[64] in Phage T4 Gene 32 Protein: Spectroscopic Evidence for a Novel Zinc Coordination Complex," Biochem., 33(26):8139-8148, 1994.
Rashid et al., "RecA/Rad51 Homolog from *Thermococcus kodakaraensis* KOD1," Methods Enzymol., 334:261-270, 2001.
Reddy et al., "Assembly of a functional replication complex without ATP hydrolysis: A direct interaction of bacteriophage T4 gp45 with T4 DNA polymerase," Proc. Natl. Acad. Sci. USA, 90:3211-3215, 1993.
Reddy et al., "Using Macromolecular Crowding Agents to Identify Weak Interactions within DNA Replication Complexes," Methods Enzymol., 262:466-476, 1995.
Riddles and Lehman, "The Formation of Plectonemic Joints by the recA Protein of *Escherichia coli*," J. Biol. Chem., 260:170-173, 1985.
Rivas et al., "Life in a crowded world—Workshop on the Biological Implications of Macromolecular Crowding," EMBO Reports, 5(1):23-27, 2004.
Ronaghi et al., "A Sequencing Method Based on Real-Time Pyrophosphate," Science, 281:363-365, 1998.
Rosselli and Stasiak, "Energetics of RecA-mediated Recombination Reactions Without ATP Hydrolysis RecA Can Mediate Polar Strand Exchange but is Unable to Recycle," J. Mol. Biol., 216:335-352, 1990.
Roux, "Optimization and troubleshooting in PCR," Genome Res., 4:S185-S194, 1995.
Saiki et al., "Primer-Directed Enzymatic Amplification of DNA with a Thermostable DNA Polymerase," Science, 239:487-491, 1988.
Salinas et al., "Homology Dependence of UvsX Protein-catalyzed Joint Molecule Formation," J. Biol. Chem., 270:5181-5186.
Salinas and Benkovic, "Characterization of bacteriophage T4-coordinated leading- and lagging-strand synthesis on a minicircle substrate," PNAS, 97(13):7196-7201, 2000.
Sanders et al., "Use of a macromolecular crowding agent to dissect interactions and define functions in transcriptional activation by a DNA-tracking protein: Bacteriphage T4 gene 45 protein and late transcription," Proc. Natl. Acad. Sci. USA, 91:7703-7707, 1994.
Sanders et al., "Dual targets of a transcriptional activator that tracks on DNA," EMBO J., 16(11):3124-3132, 1997.
Sanger et al., "DNA sequencing with chain-terminating inhibitors," Proc. Natl. Acad. Sci. USA, 75:5463-5467, 1977.
Savva and Pearl, "Cloning and Expression of the Uracil-DNA Glycosylase Inhibitor (UGI) From Bacteriophage PBS-1 and Crystallization of a Uracil-DNA Glycosylase-UGI Complex," Proteins, 22(3):287-289, 1995.
Scheerhagen et al., "Binding Stoichiometry of the Gene 32 Protein of Phage T4 in the Complex with Single Stranded DNA Deduced from Boundary Sedimentation," J. Biomol. Struct. Dyn., 3:887-898, 1986.
Scheerhagen et al., "Hydrodynamic studies of a DNA-protein complex—Dimensions of the complex of single-stranded 145 base DNA with gene 32 protein of phage T4 deduced from quasi-elastic light scattering," FEBS Lett., 184(2):221-225, 1985.
Shan et al., "RecA Protein Filaments: End-dependent Dissociation from ssDNA and Stabilization by RecO and RecR Proteins," J. Mol. Biol., 265:519-540, 1997.
Shibata et al., "Purified *Escherichia coli* recA protein catalyzes homologous pairing of superhelical DNA and single-stranded fragments," Proc. Natl. Acad. Sci. USA, 76:1638-1642, 1979.
Shibata et al., "Homologous pairing in genetic recombination: Formation of D loops by combined action of recA protein and a helix-destabilizing protein," Proc. Natl. Acad. Sci. USA, 77:2606-2610, 1980.
Shibata et al, "Homologous pairing in genetic recombination: Complexes of recA protein and DNA," Proc. Natl. Acad. Sci. USA, 76(10):5100-5104, 1979.
Singleton et al., "Structural Analysis of DNA Replication Fork Reversal by RecG," Cell, 107:79-89, 2001.
Skinner et al., "Use of the Glu-Glu-Phe C-terminal Epitope for Rapid Purification of the Catalytic Domain of Normal and Mutant ras GTPase-activating Proteins," J. Biol. Chem., 266:14163-14166, 1991.
Southern et al., "Analyzing and Comparing Nucleic Acid sequences by Hybridization to Arrays of Oligonucleotides: Evaluation Using Experimental Models," Genomics, 13:1008-1017, 1992.
Spies et al., "The RadA protein from a hyperthermophilic archaeon *Pyrobaculum islandicum* is a DNA-dependent ATPase that exhibits two disparate catalytic modes, with a transition temperature at 75° C.," Eur. J. Biochem., 267:1125-1137, 2000.
Steffen and Bryant, "Purification and Characterization of the RecA Protein from *Streptococcus pneumoniae*," Arch. Biochem. Biophys., 382:303-309, 2000.
Story et al., "Structural Relationship of Bacterial RecA Proteins to Recombination Proteins from Bacteriophage T4 and Yeast," Science, 259(5103):1892-1896, 1993.

(56) References Cited

OTHER PUBLICATIONS

Sun and Shamoo, "Biochemical characterization of Interactions between DNA Polymerase and Single-stranded DNA-binding Protein in Bacteriophage RB69," J. Biol. Chem., 278(6):3876-3881.
Takeshita et al., "Oligodeoxynucleotides Containing Synthetic Abasic Sites," J. Biol. Chem., 262:10171-10179, 1987.
Tang et al., "Roles of E. coliDNA polymerases IV and V in lesion-targeted and untargeted SOS mutagenesis," Nature, 404:1014-1018, 2000.
Tinker-Kulberg et al., "A direct interaction between a DNA-tracking protein and a promoter recognition protein: implications for searching DNA sequence," EMBO J., 15(18):5032-5039, 1996.
Tissier et al., "Purification and Characterization of a DNA Strand Transferase from Broccoli," Plant Physiol., 108:379-386, 1995.
Tracy and Kowalczykowski, "In vitro selection of preferred DNA pairing sequences by the Escherichia coli RecA protein," Genes Dev., 10:1890-1903, 1996.
Tsurimoto and Matsubara, "Replication of λ dv plasmid in vitro promoted by purified λ O and P proteins," Proc. Natl. Acad. Sci. USA, 79:7639-7643, 1982.
Tyagi et al., "Multicolor molecular beacons for allele discrimination," Nature Biotechnol., 16:49-53, 1998.
Van Ness et al., "Isothermal reactions for the amplification of oligonucleotides," Proc. Natl. Acad. Sci. USA, 100(8):4504-4509, 2003.
Villemain et al., "Mutations in the N-terminal Cooperativity Domain of Gene 32 protein Alter Properties of the T4 DNA Replication and Recombination Systems," J. Biol. Chem., 275:31496-31504, 2000.
Vincent et al., "Helicase-dependent isothermal DNA amplification," EMBO Rep., 5:795-800, 2004.
Volodin and Camerini-Otero, "Influence of DNA Sequence on the Positioning of RecA Monomers in RecA-DNA Cofilaments," J. Biol. Chem., 277(2):1614-1618, 2002.
Volodin et al., "Phasing of RecA monomers on quasi-random DNA sequences," FEBS Letters, 546:203-208, 2003.
Voloshin et al., "Homologous DNA Pairing Promoted by a 20-Amino Acid Peptide Derived from RecA," Science, 272:868-872, 1996.
Voloshin et al., "The Homologous Pairing Domain of RecA also Mediates the Allosteric Regulation of DNA Binding and ATP Hydrolysis: A Remarkable Concentration of Functional Residues," J. Mol. Biol., 303(5):709-720, 2000.
Walker et al., "Isothermal in vitro amplification of DNA by a restriction enzyme/DNA polymerase system," Proc. Natl. Acad. Sci. USA, 89:392-396, 1992.
Walker, "Empirical aspects of strand displacement amplification," Genome Res., 3:1-6, 1993.
Walker et al., "Distantly related sequences in the α- and β-subunits of ATP synthase, myosin, kinases and other ATP-requiring enzymes and a common nucleotide binding fold," EMBO J., 1:945-951, 1982.
Wang and Mosbaugh, "Uracil-DNA Glycosylase Inhibitor of Bacteriophage PBS2: Cloning and Effects of Expression of the Inhibitor Gene in Escherichia coli," J. Bacteriol., 170(3):1082-1091, 1988.
Webb et al., "An Interaction between the Escherichia coli RecF and RecR Proteins Dependent on ATP and Double-stranded DNA," J. Biol. Chem., 270:31397-31404, 1995.
Webb et al., "Recombinational DNA Repair: The RecF and RecR Proteins Limit the Extension of RecA Filaments beyond Single-Strand DNA Gaps," Cell, 91:347-356, 1997.
Webb et al., "ATP Hydrolysis and DNA Binding by the Escherichia coli RecF Protein," J. Biol. Chem., 274:15367-15374, 1999.
West et al., "Purification and Properties of the recA Protein of Proteus mirabilis," J. Biol. Chem., 258:4648-4654, 1983.
Wetmur et al, "Cloning, Sequencing, and Expressiono f RecA Proteins from Three Distantly Related Thermophilic Eubacteria," J. Biol. Chem., 269:25928-25935, 1994.
Wittwer et al., "Continuous Fluorescence Monitoring of Rapid Cycle DNA Amplification," Biotechniques, 22(1):130-1, 134-138, 1997.
Xu and Marians, "A Dynamic RecA Filament Permits DNA Polymerase-catalyzed Extension of the Invading Strand in Recombination Intermediates," J. Biol. Chem., 277:14321-14328, 2002.
Yang et al., "Comparison of Bacteriophage T4 and UvsX and Human Rad51 Filaments Suggests that RecA-like Polymers May Have Evolved Independently," J. Mol. Biol., 312(5):999-1009, 2001.
Yonesaki et al., "Purification and some of the functions of the product of bacteriophage T4 recombination genes, uvsX and uvsY," Eur. J. Biochem., 148:127-134, 1985.
Young et al., "The Kinetic Mechanism of Formation of the Bacteriophage T4 DNA polymerase Sliding Clamp," J. Mol. Biol., 264:440-452, 1996.
Zhang et al., "Ramification Amplification: A Novel Isothermal DNA Amplification Method," Mol. Diagn., 6:141-150, 2001.
Zimmerman and Trach, "Macromolecular crowding extends the range of conditions under which DNA polymerase is functional," Biochim. Biophys. Acta., 949:297-304, 1988.
Zimmerman and Minton, "Macromolecular Crowding: Biochemical, Biophysical, and Physiological Consequences," Annu. Rev. Biophys. Biomol. Struct., 22:27-65, 1993.
Zimmerman and Harrison, "Macromolecular crowding increases binding of DNA polymerase to DNA: An adaptive effect," Proc. Natl. Acad. Sci. USA, 84(7):1871-1875, 1987.
Zinchenko and Yoshikawa, "$Na^+$ Shows a Markedly Higher Potential than $K^{30}$ Compaction in a Crowded Environment," Biophysical Journal, 88:4118-4123, 2005.
Partial European Search Report for EP 08012222.9, 3 pgs., dated Nov. 12, 2008.
Office Action for U.S. Appl. No. 10/813,693 (U.S. counterpart to WO 00/41524—Foreign Patent Document No. 1 above), dated May 28, 2009.
Office action in corresponding Canadian application 2,476,481, dated May 16, 2013, 9 pages.
Notice of Allowance and allowed text for corresponding EP Application No. 06849466.5 (total of 82 pages), dated Oct. 23, 2012.
Barnes and Rowlyk, "Magnesium precipitate hot start method for PCR," Mol. and Cell. Probes, 16(3):167-171, 2002.
Crowe et al., "Is Trehalose Special for Preserving Dry Biomaterials?," Biophys. J., 71(4):2087-2093, 1996.
Mannarelli and Kurtzman, "Rapid Identification of Candida albicans and Other Human Pathogenic Yeasts by Using Short Oligonucleotides in a PCR," J. Clin. Microbiol., 36(6):1634-1641, 1998.
Ramos et al., "Stabilization of Enzymes against Thermal Stress and Freeze-Drying by Mannosylglycerate," Appl. and Env. Microbiol., 63(10):4020-4025, 1997.
Kim and Chae, "Optimized protocols for the detection of porcine circovirus 2 DNA from formalin-fixed paraffin-embedded tissues using nested polymerase chain reaction and comparison of nested PCR with in situ hybridization," J. Vir. Methods, 92:105-11, 2001.
Miyamoto et al., "Development of a New Seminested PCR Method for Detection of Legionella Species and Its Application to Surveillance of Legionellae in Hostpial Cooling Tower Water," Applied and Environmental Microbiology, 63(7):2489-2494, 1997.
Monis and Saint, "Development of a Nested-PCR Assay for the Detection of Cryptosporidium Parvum in Finished Water," Wat. Res., 35(7):1641-1648, 2001.
Ozbas et al., "Development of a multiplex and semi-nested PCR assay for detection of Yersinia enterocolitica and Aeromonas hydrophila in raw milk," Food Microbiology, 17:197-203, 2000.
European Office Action, for the corresponding EP Application No. 11151743.9, dated Aug. 8, 2012.
"UvsX RecA-like recombination protein [Enterobacteria phage RB69]", online NBCI, http://www.ncbi.nlm.nih.gov/protein/32350347?sat—&satkey=7100722, Apr. 5, 2005 (retrieved on Aug. 22, 2012).
"UvsX [Aeromonas phage Aeh1]", online NBCI, http://www.ncbi.nlm.nih.gov/protein/38639939?sat=12&satkey=851579, Mar. 30, 2006 (retrieved on Aug. 22, 2012).

(56) References Cited

OTHER PUBLICATIONS

Desplats and Krisch, "The diversity and evolution of the T4-type bacteriophages," Res. Microbiol, 154(4):259-267, 2003.
Miller et al., "Complete Genome Sequence of the Broad-Host-Range vibriophage KVP40: Comparative Genomics of a T4-Related Bacteriophage," J. Bacteriol., 185(17):5220-5233, 2003.
Accession: NP_861734 [GI:32453528], Definition: UvsX RecA-like recombination protein [Enterobacteria phage RB69]. NCBI Sequence Revision History [online]; Mar. 30, 2006 uploaded, NCBI, <URL:http://www.ncbi.nlm.nih.gov/protein/32453528?sat=12&satkey=7706006> [retrieved on Aug. 30, 2011].
Accession: NP_861890 [GI: 32453681], Definition: UvsY recombination, repair and ssDNA binding protein [Enterobacteria phage RB69]. NCBI Sequence Revision History [online]; Mar. 30, 2006 uploaded, NCBI, <URL: http://www.ncbi.nlm.nih.gov/protein/32453681?sat=12&satkey=7706006> [retrieved on Aug. 30, 2011].
Cai, "An inexpensive and simple nucleic acid dipstick for rapid pathogen detection," LAUR #05-9067 of Los Alamos National Laboratory, Aug. 22, 2006.
Conklin and Drake, "Isolation and Characterization of conditional Alleles of bacteriophage T4 Genes uvsX and uvsY," Genetics, 107:505-523, 1984.
Huang et al., "Relationship between Bacteriophage T4 and T6 DNA Topoisomerases," J. Biol. Chem., 260(15):8973-8977, 1985.
Ishmael et al., "Protein-Protein Interactions in the Bacteriophage T4 Replisome," J. Biol. Chem., 278(5):3145-3152, 2003.
Kool, "Replacing the Nucleobases in DNA with Designer Molecules," Acc. Chem. Res., 35:936-943, 2002.
Kreader, "Relief of amplification inhibition in PCR with bovine serum albumin or T4 gene 32 protein," Appl. Env. Microbiol., 62:1102-1106, 1996.
Mosig et al., "Two recombination-dependent DNA replication pathways of bacteriophage T4, and their roles in mutagenesis and horizontal gene transfer," Proc. Natl. Acad. Sci. USA, 98:8306-8311, 2011.
Nagai et al., "Additive Effects of Bovine Serum Albumin, Dithiothreitol, and Glycerol in PCR," 44:157-163, 1998.
Petrov et al., "Plasticity of the Gene Functions for DNA Replication in the T4-like Phages," J. Mol. Biol., 361:46-68, 2006.
Raap, "Advances in fluorescence in situ hybridization," Mutation Research, 400:287-298, 1998.
Raap et al., "Synthesis and Proton-NMR Studies of Oligonucleotides Containing and Apurinic (AP) Site," J. Biom. Structure & Dynamics, 5(2):219-247, 1987.
Waidner, et al., "Domain effects on the DNA-interactive properties of bacteriophage T4 gene 32 protein," J. Biol. Chem., 276:2509-16 (2001).
Wang et al., "Modular Organization of T4 DNA Polymerase," J. Biol. Chem., 270(44):26558-26564, 1995.
Yeh et al., "Divergence of a DNA Replication Gene Cluster in the T4-Related Bacteriophage RB69," J. Bacteriol., 180(8):2005-2013, 1998.
Response to EP Office Action for corresponding EP Application No. 06849466.5, dated Jun. 30, 2009.
Australian Office Action, for the corresponding Australia Application No. 2006339057, filed Jul. 25, 2006, dated Jul. 5, 2010.
Response to Canadian Examination Report dated Jul. 2, 2010, for corresponding Canadian application Serial No. 2,616,241, as filed on Jan. 4, 2011.
Response to EP Office Action, for corresponding EP Application No. 06849466.5, dated May 13, 2011.
Response to Office Action, for the corresponding Australian Application No. 2006339057, Aug. 5, 2011.
Japanese Office Action, for the corresponding Japanese Patent Application No. 2008-523491, dated Nov. 20, 2011 (dated Dec. 6, 2011).
Examination Report from corresponding European Application No. 11184367.8-1403, dated Aug. 7, 2014, pp. 1-7.
Crannell et al., "Quantification of HIV-1 DNA Using Real-Time Recombinase Polymerase Amplification," American Chemical Society 2014, 86, 5615-5619.
Office Action from corresponding Japanese Patent Application No. 2013-029664, dated May 8, 2015, pp. 1-7.
Jill S. Bleuit et al., "Mediator proteins orchestrate enzyme-ssDNA assembly during T4 recombination-dependent DNA replication and repair," PNAS:98(15):8298-8305, Jul. 17, 2001.
Beernink and Morrical, "RMPs: recombination/replication mediator proteins," TIBS Oct. 24, 1999:385-389.
Thomas Kodadek "Functional Interactions Between Phage T4 and E. coli DNA-Binding Proteins During the Presynapsis Phase of Homologous Recombination," Biochemical and Biophysical Research Communications, 172(2):804-810 (1990).
Efim I. Golub et al., "Joints formed by RecA protein from oligonucleotides and duplex DNA block initiation and elongation of transcription," Nucleic Acids Research, 20(12):3121-3125 (1992).
Menetski and Kowalczykowski, "Enhancement of *Escherichia coli* RecA Protein Enzymatic Function by dATP," Biochemistry 1989, 28, 5871-5881.
Riddles and Lehman, "The Formation of Paranemic and Plectonemic Joints between DNA Molecules by the recA and Single-stranded DNA-binding Proteins of *Escherichia coli*," The Journal of Biological Chemistry, 260(1):165-169 (1985).
Steffen and Bryant, "Reevaluation of the Nucelotide Cofactor Specificity of the RecA Protein from *Bacillus subtilis*," The Journal of Biological Chemistry, 274(37):25990-25994 (1999).
Toshihiro Horii et al., "Organization of the recA gene of *Escherichia coli*," Proc. Natl. Acad. Sci. USA., 77(1):313-317 (1980).
Kozer et al., "Effect of Crowding on Protein-Protein Association Rates: Fundamental Differences between Low and High Mass Crowding Agents," J. Mol. Biol. (2004) 336, 763-774.
Kadyrov et al., "Properties of Bacteriophage T4 Proteins Deficient in Replication Repair," the Journal of Biological Chemistry, 276(27):25247-25255, 2003.
Transmittal of 3$^{rd}$ Party Observations in Application No. 10180482. 1, dated Dec. 3, 2015, p. 1.
Third Party Observations under Article 115 EPC in Application No. 10180482, pp. 1-8, dated Nov. 27, 2015.
Third Party Observation for Application No. EP20100180482, pp. 1-2, dated Nov. 27, 2015 16:42.
Third Party Observation for Application No. EP20100180482, pp. 1-2, dated Nov. 27, 2015 16:46.
Third Party Observation for Application No. EP20100180482, pp. 1-2, dated Nov. 27, 2015 16:49.
Office Action in corresponding European Application No. 10180482.1, dated Jan. 17, 2017, pp. 1-7.

* cited by examiner

Carry-over contamination control using *E.coli* UNG & UNG inhibitor

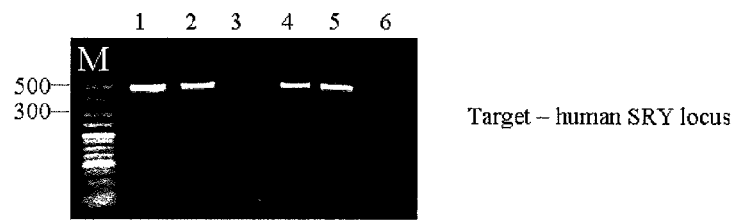

Target – human SRY locus

1. Template
2. Template + UNG (5 minutes) + UNG Inhibitor (after 5 minutes)
3. Template + contaminating DNA (containing dUTP) + UNG
4. Template + contaminating DNA (containing dUTP) + UNG(5mins) + UNG Inhibitor
5. Contaminating DNA (containing dUTP)
6. Contaminating DNA (containing dUTP) + UNG(5mins) + UNG Inhibitor

Fig. 6

METHODS FOR MULTIPLEXING RECOMBINASE POLYMERASE AMPLIFICATION

RELATED APPLICATIONS

This application is a continuation of U.S. application Ser. No. 13/177,007 filed Jul. 6, 2011, which is a continuation of U.S. application Ser. No. 11/988,825 filed Jun. 2, 2009, which is a National Stage Application of PCT/IB06/04113 filed Jul. 25, 2006, and claims the benefit of priority from U.S. Application Ser. No. 60/702,533 filed Jul. 25, 2005 and U.S. Application Ser. No. 60/728,424 filed Oct. 18, 2005. The contents of the prior applications are incorporated by reference herein.

BACKGROUND

Recombinase Polymerase Amplification (RPA) is a DNA amplification process that utilizes enzymes to match synthetic oligonucleotide primers to their complementary partners in duplex DNA. (Armes and Stemple, U.S. patent Appl. 60/358,563 filed Feb. 21, 2002). RPA depends upon components of the cellular DNA replication and repair machinery. The notion of employing some of this machinery for in vitro DNA amplification has existed for some time (Zarling et al. U.S. Pat. No. 5,223,414), however the concept has not transformed to a working technology until recently as, despite a long history of research in the area of recombinase function involving principally the E. coli recA protein, in vitro conditions permitting sensitive amplification of DNA have only recently been determined (Piepenburg et al. U.S. patent application Ser. No. 10/931,916 filed Sep. 1, 2004, also Piepenburg et al., PlosBiology 2006).

RPA offers a number of advantages over traditional methods of DNA amplification. These advantages include the lack of a need for any initial thermal or chemical melting, the ability to operate at low constant temperatures without a need for absolute temperature control, as well as the observation that complete reactions (lacking target) can be stored in a dried condition. These characteristics demonstrate that RPA is a uniquely powerful tool for developing portable, accurate, and instrument-free nucleic acid detection tests.

BRIEF DESCRIPTION OF THE INVENTION

The present invention relates to methods of nucleic acid amplification which include novel recombinase polymerase amplification (RPA) protocols for rapid and efficient amplification of nucleic acids in a process that can be easily multiplexed.

One embodiment of the invention is directed to a method wherein a plurality of RPA which can be performed simultaneously in a single reaction (in a single tube) and wherein the results may be detected simultaneously. The single RPA reaction is described first below and methods of multiplexing said reaction is described second.

One aspect of the invention is directed to methods of RPA which generates easily detectable amplimers (an amplified nucleic acid which is the product of an RPA reaction). The RPA process amplified a double stranded target nucleic acid molecule comprising a first and a second strand of DNA. Step (a) involves contacting a recombinase agent with a first and a second nucleic acid primer and a third extension blocked primer which comprises one or more noncomplementary or modified internal residue to form a first, second and third nucleoprotein primer. Step (b) involves contacting the first and second nucleoprotein primers to said double stranded target nucleic acid thereby forming a first double stranded structure between said first nucleoprotein primer and said first strand of DNA at a first portion of said first strand (forming a D loop) and a second double stranded structure between said second nucleoprotein primer and said second strand of DNA at a second portion of said second strand (forming a D loop) such that the 3' ends of said first nucleoprotein primer and said first nucleoprotein primer are oriented toward each other on the same target nucleic acid molecule with a third portion of target nucleic acid between said 3' ends; Step (c) involves extending the 3' end of said first nucleoprotein primer and second nucleoprotein primer with one or more polymerases and dNTPs to generate a first amplified target nucleic acid with an internal region comprising the third portion of nucleic acid. Step (d) involves contacting said amplified target nucleic acid to said third nucleoprotein primer to form a third double stranded structure at the third portion of said amplified target nucleic acid (forming a D loop) in the presences of a nuclease; wherein said nuclease specifically cleaves said noncomplementary internal residue only after the formation of said third double stranded structure to form a third 5' primer and a third 3' extension blocked primer. Step (d) involves extending the 3' end of said third 5' primer with one or more polymerase and dNTP to generate a second double stranded amplified nucleic acid which comprises said first nucleic acid primer and said third 5' primer. The RPA reaction is continued until a desired degree of the second double stranded amplified nucleic acid is reached. It should be noted that this process, along with any related embodiments, may be used for multiplex RPA reaction (described below).

The recombinase agent may be, for example, uvsX, RecA and functional analogs thereof. Further, the RPA reaction may be performed in the presence of uvxY, gp32, single strand binding proteins and other usual RPA reagents. Methods for performing RPA are disclosed, for example, in U.S. Appl. 60/358,563 filed Feb. 21, 2002, U.S. application Ser. No. 10/371,641, filed Feb. 21, 2003, 2003, U.S. patent application Ser. No. 10/931,916 filed Sep. 1, 2004 and PCT/IB2005/001560 (WO2005/118853) filed Apr. 11, 2005.

The nuclease used in this RPA reaction should specifically cleave the noncomplementary residue or the modified internal residue preferentially when the third extension blocked primer is hybridized to a DNA to form a double stranded structure. It is preferred that the nuclease do not cleave the noncomplementary residue or the modified internal residue when the extension blocked primer is in single stranded form—regardless of whether the primer is attached to recombinase or SSB. In a preferred embodiment, the nuclease is a DNA glycosylase or AP endonuclease. If the modified internal residue is a uracil or inosine, the preferred nuclease is uracil glycosylase or hypoxanthine-DNA glycosylase respectively. The nuclease may recognize the non-complementary base by nature of a mismatch which forms a region of noncomplementary residues (i.e., a bubble) in an otherwise double stranded structure. In this case, the nuclease recognizes a base mismatch between the noncomplementary residues and cleaves primer at the noncomplementary base.

The nuclease used in any of the processes of the invention may be a DNA glycosylase or an AP endonuclease. The nuclease may function by recognizing a base mismatch between said first extension blocked primer and said target nucleic acid and cleaving the extension blocked primer at the base mismatch without cleaving the target nucleic acid. The nuclease, alternatively, may recognize a damaged residue, an abasic site or abasic site mimic, or any other modification which may be incorporated into synthetic oligonucleotides. The nuclease may be, for example, fpg, Nth, MutY, MutS, MutM, *E. coli*. MUG, human MUG, human Ogg1, a vertebrate Nei-like (Neil) glycosylases, Nfo, exonuclease III, uracil glycosylase, hypoxanthine-DNA and functional analogs and homologs thereof. The functional analogs and homologs may be of any mammalian, bacterial or viral original. As additional examples, if the modified base is inosine, the nuclease may be hypoxanthine-DNA glycosylase; if the modified base is uracil, the nuclease may be uracil glycosylase. In a preferred embodiment, these nucleases may be from *E. coli*. In a preferred embodiment, the nuclease is *E. coli* Nfo or *E. coli* exonuclease III and the modified internal residue is a tetrahydrofuran residue or a linker group. A 'linker' (also called a carbon linker or 'spacer') is a carbon-containing chain which is used to join the 3' position of one sugar to the (usually) 5' position of another. Common spacers may comprise about 3, 6, 9, 12 or 18 carbon chains although it may be of any number of carbon chains. Carbon-oxygen-carbon linkages are common in these spacers, presumably to reduce hydrophobicity. Nfo and exonuclease III (and homologs) can recognize the sugar 3'-O—C linkage on the 3' end of a nucleotide linked to a spacer and cleave it. See, for example, C18 spacer (18-O-Dimethoxytritylhexaethyleneglycol, 1-[(2-cyanoethyl)-(N,N-diisopropyl)]-phosphoramidite (Glen Research, Sterling, Va., USA, cat#10-1918-90).

As used herein, an "abasic residue" in an oligonucleotide refers to a molecular fragment (MF) within an oligonucleotide chain where the molecular fragment approximates the length of a ribofuranose or a deoxyribofuranose sugar in such a way that bases adjacent to the molecular fragment are separated from one another by the same, or effectively the same, distance as if a ribofuranose or a deoxyribofuranose sugar of any of A, G, C, T, or U were present in place of the abasic residue. The abasic residue may incorporate a ribofuranose or deoxyribofuranose ring as in native A, G, C, T, or U. However, the abasic residue does not contain a base or other molecule that can interact with the base on the opposite strand of a duplex which is formed with the abasic residue-containing oligonucleotide. Thus, an abasic residue may be an apurine or apyrimidine structure, a base analog, or an analogue of a phosphate backbone. The abasic substitution may also consist of a backbone of N-(2-aminoethyl)-glycine linked by amide bonds. In a preferred embodiment, the abasic residue is tetrahydrofuran or D-spacer (a type of tetrahydrofuran). Both a D-spacer and tetrahydrofuran effectively are a deoxyribose sugar in which both the 1' and 2' position lack OH residues. Normally the 1' position of a true abasic residue in DNA would have a hydroxyl in the position where the base is normally attached, however this is unstable as the ring form interconverts with an open-ring aldehyde form (see below) which can then degrade by the process of beta-elimination. Removal of this hydroxyl leads to a stable form readily synthesized into oligonucleotides. Tetrahydrofuran-type abasic sites and their use as abasic residues are known. The tetrahydrofuran may be placed into oligonucleotides during synthesis by ordering reagents from Glen Research (Sterling, Va., USA).

The one or more noncomplementary or modified internal residue is internal because it is not the 5' most or 3' most residue of the first extension blocked primer. In a preferred embodiment, the one or more noncomplementary internal residue is at least 10 residues away from the 5' or 3' residue of a primer. In a more preferred embodiment, the one or more noncomplementary internal residue is at least 15, or at least 20 residues away from the 5' or 3' residue of a primer.

The one or more noncomplementary internal residue may be introduced by synthesizing an oligonucleotide primer with one or more noncomplementary residue. A noncomplementary residue is any residue that does not form a Watson Crick base pair (hydrogen bond) with its corresponding residue in a double stranded structure. For example, if a "T" at a particular location is needed to form a Watson-Crick base pair between a primer and a target nucleic acid, the use of an "A" would cause the "A" to be non complementary. As a further example, each of the middle bases in the following double stranded structure is a noncomplementary base.

```
primer    aaaaa    (SEQ ID NO: 1)
          || ||
target    ttatt    (SEQ ID NO: 2)
primer    aagaa    (SEQ ID NO: 3)
          || ||
target    ttatt    (SEQ ID NO: 4)
primer    aacaa    (SEQ ID NO: 5)
          || ||
target    ttatt    (SEQ ID NO: 6)
```

It is known that the presence of noncomplementary residues in a double stranded nucleic acid will produce a bubble within the double stranded nucleic acid. While one noncomplementary or modified internal residue is sufficient for functioning with the methods of the invention, more than one noncomplementary or modified internal residues may be used. When more than one is used, they may adjacent to each other on an oligonucleotide or they may be separated. It should be noted that if the nuclease cleaves the target nucleic acid at the mismatch or noncomplementary location, the target DNA is repaired rapidly by dNTP and polymerase using the primer as a template. Because of this, this reaction would not affect the processes of this disclosure.

The one or more noncomplementary internal residue of the first extension blocked primer may be a modified internal residue. The modified internal residue may be any chemical structure (residue) that cannot form a Watson-Crick base pairing structure with its corresponding base in a double stranded nucleic acid structure. If more than one noncomplementary internal residue is used, they can be a mixture of noncomplementary internal residues or modified internal residues. The term "modified internal residue," also includes, at least, any residue not normally found in DNA—that is any residue which is not an "A", "G", "C" or "T" such as, for example uracil or inosine.

The modified internal residue may be inosine, uracil, 8-oxoguanine, thymine glycol, or an abasic site mimic. Preferred abasic site mimics include a tetrahydrofuran residue or D-spacer (which can be produced as a product of employing a 5'-O-Dimethoxytrityl-1',2'-Dideoxyribose-3'-[(2-cyanoethyl)-(N,N-diisopropyl)]-phosphoramidite during oligonucleotide synthesis.

The extension blocked primer is blocked at its 3' end so that it cannot normally be elongated by polymerase and dNTP even in the presence of a complimentary template. Methods of blocking a primer are well known and include, at least, the inclusion of a blocked 3' nucleotide. The blocked 3' nucleotide may contain, for example, a blocking group that prevents polymerase extension. Generally, the blocking groups are attached to the 3' or 2' site of the 3' sugar residue but other locations of attachments are possible. One of the most common 3' blocking methods is to place a dideoxy sugar at the 3' end of an oligonucleotide. The blocking group may be, for example, a detectable label.

A detectable label is defined as any moiety that may be detected using current methods. These labels include, at least, a fluorophore (also called a fluorescent molecule, fluorochrome), an enzyme, a quencher, an enzyme inhibitor, a radioactive label, a member of a binding pair, a digoxygenin residue, a peptide, and a combination thereof.

"A member of a binding pair" is meant to be one of a first and a second moiety, wherein said first and said second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, peptide/anti-peptide, ligand/receptor and rhodamine/anti-rhodamine), biotin/avidin (or biotin/streptavidin) and calmodulin binding protein (CBP)/calmodulin. Other suitable binding pairs include polypeptides such as the FLAG-peptide (DYKDDDDK; SEQ ID NO:7) [Hopp et al., BioTechnology, 6:1204 1210 (1988)]; the KT3 epitope peptide (Martin et al., Science 255:192 194 (1992)); tubulin epitope peptide (Skinner et al., J. Biol. Chem. 266:15163 15166 (1991)); and the T7 gene 10 protein peptide tag (Lutz-Freyermuth et al., Proc. Natl. Acad. Sci. USA, 87:6393 6397 (1990)) and the antibodies each thereto. Generally, in a preferred embodiment, the smaller of the binding pair partners serves as the detectable label, as steric considerations may be important. In addition to the above, any of the nucleic acid and nucleotides of the RPA reaction may be labeled with a detectable label.

In any of the RPA processes of the invention where a detectable label is used, the detectable label may be used to monitor the progress (the production of amplimers) of the RPA reaction. In one aspect, if the primers are labeled, monitoring may involve detecting a label in an amplimer. Since amplimers would be expected to be larger than the primers used, detection may involve, for example gel electrophoresis and the detection of the proper sized amplimer. Alternatively, labeled amplimers may be separated by labeled primers by a more rapid process such as column chromatography (including spin columns, push columns and the like). Since the RPA methods of the invention has high specificity and low artifact production (high signal to noise), monitoring may involve performing RPA using nucleotides attached to detectable labels and measuring the amount of labels attached to high molecular weight nucleic acid (e.g., nucleic acid of more than 100 bases in length). For example, radioactive dNTPs may be used and the progress of the RPA reaction may be monitored by following the incorporation of radiation into high molecular weight DNA. Techniques that monitor incorporation of nucleotides into high molecular weight DNA include gel electrophoresis, size exclusion column (e.g., conventional, spin and push columns) and acid precipitation.

If the first nucleic acid primer and the third 5' primer are each labeled with a different detectable label, then the amplified product (the second double stranded amplified nucleic acid) will be the only nucleic acid species with both labels. This double labeled nucleic acid species may be detected by a variety of means. In one preferred method, the amplified product may be detected using a flow strip. In one preferred embodiment, one detectable label produces a color and the second label is an epitope which is recognized by an immobilized antibody. A product containing both labels will attach to an immobilized antibody and produce a color at the location of the immobilized antibody. An assay based on this detection method may be, for example, a flow strip (dip stick) which can be applied to the whole RPA reaction. A positive amplification will produce a band on the flow strip while a negative amplification would not produce any color band.

It should be noted that this RPA amplification process using 3 primers may be multiplexed (referred to herein as multiplex RPA). That is, multiple RPA process using 3 primers, as discussed above, may be performed in the same reaction (tube). Multiplex RPA may be performed with one or more target nucleic acids. Each process is performed with a different combination of first and second nucleic acid primers which is specific for a different region of one or more target nucleic acids. In a preferred embodiment, when multiple RPA processes are performed in the same reaction, each RPA process uses a first nucleic acid with the same label but not necessarily the same sequence. Further, each process uses the same third extension blocked primer with a second detectable label. In this way, by measuring the accumulation of double stranded nucleic acid product with both the first detectable label and the second detectable label, the cumulative amplification of each RPA process may be measured.

Multiplexed RPA is useful for many purposes. For example, multiple pathogens may share a common nucleic acid sequence that is too small for direct amplification by RPA. Furthermore, the common nucleic acid sequence have different flanking sequence in each organism so that a single set of RPA primers cannot be designed to amplify this common nucleic acid sequence in multiple organisms. Using the process of multiplex RPA as described above, a plurality of combination of RPA primers may be used in one reaction, wherein each combination would amplify the common nucleic acid sequence in one organism and this common nucleic acid sequence would be concomitantly amplified by the common third primer (third extension blocked primer). Multiplex RPA with primer combinations designed to detect multiple pathogens, may be used for example, in an assay to detect methicillin resistant *S. aureus* strains by amplifying and detecting a common sequence (e.g., mec2) in each strain. By using the multiplexed RPA of the invention, a plurality of loci (DNA sequences) may be detected by concurrent RPA amplification. In a preferred embodiment, at least 2 simultaneous RPA are performed in an RPA. In a more preferred embodiment, at least 3, at least 5, at least 7 or at least 10 RPA reactions may be performed in the same tube.

Thus, another aspect of the invention is directed to a multiplex method of RPA comprising the steps of performing more than one RPA process in one reaction. Each individual reaction is performed as described above for RPA using 3 primers. Briefly, each reaction involves the steps of (a1) contacting a recombinase agent with a first and a second nucleic acid primer and a third extension blocked primer which comprises a noncomplementary or modified internal residue to form a first, second and third nucleoprotein primer; (a2) contacting the first and second nucleoprotein primers to said double stranded target nucleic acid thereby forming a first double stranded structure between said first nucleoprotein primer and said first strand of DNA at a first portion of said first strand and a second double stranded structure between said second nucleoprotein primer and said second strand of DNA at a second portion of said second strand such that the 3' ends of said first nucleoprotein primer and said first nucleoprotein primer are oriented toward each other on the same target nucleic acid molecule with a third portion of nucleic acid between said 3' ends; (a3) extending the 3' end of said first nucleoprotein primer and second nucleoprotein primer with one or more polymerases and dNTPs to generate a first amplified target nucleic acid with an internal region comprising the third portion of nucleic acid; (a4) contacting said amplified target nucleic acid to said third nucleoprotein primer to form a third double stranded structure at the third portion of said amplified target nucleic acid in the presences of a nuclease; wherein said nuclease specifically cleaves said noncomplementary or modified internal residue only after the formation of said third double stranded structure to form a third 5' primer and a third 3' extension blocked primer; (a5) extending the 3' end of said third 5' primer to generate a second double stranded amplified nucleic acid which comprises said first nucleic acid primer and said third 5' primer; (a6) continuing the reaction through repetition of (a2) and (a5) until a desired degree of the second double stranded amplified nucleic acid is reached. In this process, each RPA process is performed with a different combination of first and second nucleic acid primers but each process is performed with the same third extension blocked primer.

It should be noted that while each RPA process will have a different combination of first and second nucleic acid primers, primers can still be shared between RPA processes. For example, RPA process 1 may use primers 1 and 2 while RPA process 2 may use primers 2 and 3. Thus, RPA process 1 and RPA process 2 share the same primer (primer 2).

In any RPA process that involves an extension blocked primer (e.g., the third extension blocked primer) the primer may further comprises one or more detectable labels and the progress of the RPA may be monitored a second way by monitoring the detectable label on this primer. The detectable label may be a fluorophore, an enzyme, a quencher, an enzyme inhibitor, a radioactive label, one member of a binding pair and a combination of thereof. Where a fluorophore or quencher is used, the attachment may be by a fluorophore-dT amidite residue or a quencher-dT amidite residue.

In a preferred embodiment, the third extension blocked primer comprises a fluorophore and a quencher. The fluorophore and quencher are separated by between 0 to 2 bases, 0 to 5 bases, 0 to 8 bases or 0 to 10 bases, 3 to 5 bases, 6 to 8 bases, or 8 to 10 bases. In addition, the fluorophore and quencher may be separated by a greater distance when the extension blocked primer is unhybridized than when the extension blocked primer is hybridized to the target nucleic acid. Furthermore, the fluorophore or quencher may be attached to the noncomplementary or modified internal residue as long as the fluorophore and quencher are separated following cleavage of the modified internal base by the nuclease. Preferred fluorophores include fluorescein, FAM, TAMRA and preferred quenchers include a dark quencher (e.g., Dark Quencher 1, Dark Quencher 2, Black Hole Quencher 1 and Black Hole Quencher 2).

One advantage of the methods of this RPA process is that it can be performed at a low temperature such as between 14° C. and 21° C., between 21° C. and 25° C., between 25° C. and 30° C., between 30° C. and 37° C. or between, 40° C. and 43° C. Under these temperature conditions, the reaction are accelerated in the presence of 1% to 12% PEG such as between 6% to 8% PEG.

Another advantage of using extension blocked primers, for any of the methods of the invention, is that the progress of the reaction may be monitored in real time. Monitoring may involve, for example, measuring fluorescence in the RPA reaction. In this method, the fluorophore and quencher are located at a sufficiently close distance (less than 10 residues apart, as disclosed in this specification) on the primer such that the quencher prevents fluorescence from the fluorophore. However, as the extension blocked primer is cleaved by the nuclease, the quencher is separated from the fluorophore and the primer becomes fluorescent. This allows the monitoring of RPA in real time, merely by using a light source which can excite the fluorophore to fluoresce and using an optical detector to detect any fluorescence from the fluorophore which has separated from the quencher.

The primers for any of the RPA reactions of this disclosure, including the extension blocked primers, may be between 2 to 100 residues in length, such as between 12 to 30 residues in length, 12 to 40 residues in length, 12 to 50 residues in length, or 12 to 60 residues, 30 to 40 residues in length, 40 to 45 residues in length, or 45 to 50 residues in length. In a preferred embodiment, the primers may be between 30 to 100, between 35 to 100, between 40 to 100 or between 45 to 100 in length. In the most preferred embodiment, the primers are between 30 to 60 in length, between 35 to 60, between 40 to 60 or between 45 to 60 in length—these primers may be used in any RPA reactions and are especially preferred for RPA reactions below 30° C. degrees, below 15° C. degrees or below 20° C. Primers lengths of greater than 30, greater than 35, greater than 40, greater than 45 or greater than 50 bases are preferred for RPA processes performed at or below 30° C. It is understood that in the field of molecular biology, the subunits of a nucleic acid are referred to as "bases" or "residues." For example, DNA and oligonucleotide structures and lengths are referred to in bases (kilobases), basepairs or residues.

Any of the RPA reaction of the invention may be performed between 14° C. and 21° C., between 21° C. and 25° C., between 25° C. and 30° C., between 30° C. and 37° C., between 38° C. to 40° C. or between 40° C. and 48° C. Applicants have found that RPA reactions are optimal at 25° C. in the presence of between 1% to 12% percent PEG. Preferably, the concentration of PEG is between 6 to 9% such as, for example between 7 to 8%. These optimal RPA conditions applies to the RPA reactions disclosed in this application and to all RPA reactions in general.

In a typical RPA reaction of the invention, at least one strand of the target nucleic acid is amplified at least $10^7$ folds, at least $10^8$ folds or at least $10^9$ folds.

For any of the RPA methods of the invention, it is understood that the target nucleic acid may be single stranded. Single stranded nucleic acid may be converted to double stranded nucleic acid by methods known in the art including, for example, the hybridization of random primers followed by elongation by polymerase. Furthermore, the RPA reaction may be performed directly with single stranded target nucleic acid because in a first step, a RPA primer would hybridize to the single stranded target nucleic acid and extension (in the presence of nuclease in the case of the extension blocked primer) by polymerase and dNTPs would generate a double stranded target nucleic acid for subsequent RPA. Further, a specific primer may be added at the beginning of the RPA reaction to hybridize to the single stranded target nucleic acid and by extension with polymerase already present in the RPA reaction, convert the single stranded target nucleic acid into a double stranded target nucleic acid.

To reduce background and contamination, any of the RPA reactions of the invention may be performed with dUTP in the dNTP mix. We have found, surprisingly, that an RPA may be performed in the presence of dUTP and active uracil glycosylase for a first period before the uracil glycosylase is inactivated. This first period is preferably less than 20 minutes, less than 10 minutes, less than 5 minutes or less than 2 minutes. Furthermore, the uracil glycosylase may be added at any time during the first period. That is, the RPA reaction may be started with dUTP (and other dNTPs) without uracil glycosylase and the uracil glycosylase may be added at any time during the first period.

After the first period, uracil glycosylase inhibitor is added to the RPA reaction and the reaction is allowed to continue for the remainder of the RPA reaction—until a desired degree of amplification is reached. Importantly, the process is performed without temperature based inactivation of the uracil glycosylase. The uracil glycosylase inhibitor in this reaction may be a *Bacillus subtilis* phages PBS1 uracil glycosylase inhibitor or *Bacillus subtilis* phages PBS2 uracil glycosylase inhibitor. Where dUTP is used, for any RPA of this disclosure, the dNTP may consist of (1) dTTP, dATP, dUTP, dCTP and dGTP or (2) dATP, dUTP, dCTP and dGTP. In a preferred embodiment, when dUTP is used, the dNTP mixture does not contain dTTP. This method of reducing background, by adding dUTP and uracil glycosylase to a first portion of an RPA reaction has general applicability to any type of RPA. Further, this method may be combined with any of the RPA processes of this disclosure.

Another aspect of the invention relates to a method of performing RPA of a double stranded target nucleic acid molecule comprising a first and a second strand of DNA with an increased signal to noise ratio. In step A, a recombinase agent is contacted with (1) a first extension blocked primer which comprises one or more noncomplementary or modified internal residue which can be a modified internal residue, and (2) a second nucleic acid primer to form a first and a second nucleoprotein primer.

In step B, the first and second nucleoprotein primers are mixed with (contacted to) a nuclease and to the double stranded target nucleic acid such that a first double stranded structure (part of a first D-loop) between the first nucleoprotein primer and said first strand of DNA at a first portion of said first strand is formed. Furthermore, a second double stranded structure (part of a second D loop) between said second nucleoprotein primer and said second strand of DNA at a second portion of said second strand is also formed. The 3' ends of the first extension blocked primer and said second nucleic acid primer are oriented toward each other on the same double stranded target nucleic acid molecule. The nuclease specifically recognizes and cleaves the one or more noncomplementary or modified internal residue in the first extension blocked primer only after the primer forms a double stranded structure. After cleavage by the nuclease, the first extension blocked primer is cleaved into two primers, a first 5' primer and a first 3' extension blocked primer. Because the blocking group is on the 3' end of the first extension blocked primer, the first 5' primer is not blocked but the first 3' extension blocked primer is blocked and cannot be elongated by polymerase.

In step C, the 3' end of the first 5' primer and second nucleoprotein primer is extended with one or more polymerases and dNTPs (e.g., a mixture of dATP, dTTP, dCTP, and dGTP) to generate an amplified target nucleic acid. The amplified target nucleic acid may be single stranded (for example a displaced strand) or double stranded. Furthermore, single stranded amplified target nucleic acid may hybridize to form double stranded target nucleic acid. Furthermore, the RPA system of this disclosure can amplify both single stranded target nucleic acid (discussed below) or double stranded target nucleic acid so the production of single stranded or double stranded amplified target nucleic acid would not affect the outcome of RPA.

Step B and step C are repeated until a desired degree of amplification is reached. It should be noted that the RPA reaction is self perpetuating as long as the reagents do not run out. The product of one round of amplification (amplified target nucleic acid) serves as the input for subsequent round of RPA. Thus, an RPA reaction may be continued by merely continued incubation of the reaction at a desired temperature. Furthermore, since the RPA reaction disclosed is not temperature sensitive, the reaction may be continued even if there if fluctuation in the temperature. For example, a RPA reaction tube may be performed in a waterbath, on the bench top (room temperature), or even in the pocket of the experimentor (when working in the field, for example). Thus, the RPA reaction may be performed at less than 50° C., less than 40° C., less than 37° C., less than 30° C., less than 25° C., or less than 20° C.

In a preferred embodiment, the first extension blocked primer further comprises one or more detectable labels. Where the detectable label is a fluorophore or a quencher, it may be attached to the extension blocked primer by a fluorophore-dT amidite residue or quencher-dT amidite residue respectively. Other attachments are possible and widely known.

In another preferred embodiment, the extension blocked primer comprises both a fluorophore and a quencher. The fluorophore and quencher may be separated by between 0 to 2 bases, 0 to 5 bases, 0 to 8 bases or 0 to 10 bases. Naturally, it is preferred that the fluorophore and the quencher be sufficiently close to each other such that the combination is not fluorescent until they are separated. It is preferred that the fluorophore and quencher are separated by a greater distance in the nucleoprotein primer than when the primer is hybridized to the target nucleic acid. This is possible because of the action of the attached proteins (recombinase and/or SSB protein) which tend to stretch out the unhybridized primer.

In another aspect, either fluorophore or the quencher may be attached to the modified internal residue and the fluorophore and quencher can be separated following cleavage of the modified internal residue by the nuclease.

While any fluorophore may function for the methods of the invention, fluorescein, FAM and TAMRA are preferred fluorophores. The preferred quencher is a dark quencher which may be, for example, Dark Quencher 1, Dark Quencher 2, Black Hole Quencher 1 or Black Hole Quencher 2.

Another aspect of the invention is directed to an RPA process of DNA amplification of a single stranded target nucleic acid molecule comprising the steps of (a) hybridizing a first nucleic acid primer to said single stranded target nucleic acid and elongating said primer one or more polymerases and dNTPs to generate a double stranded target nucleic acid molecule comprising a first and a second strand; (b) contacting a recombinase agent with a first extension blocked primer which comprises a noncomplementary internal residue, and a second nucleic acid primer to form a first and a second nucleoprotein primer; (c) contacting the first and second nucleoprotein primers to a nuclease and to said double stranded target nucleic acid thereby forming a first double stranded structure between said first nucleoprotein primer and said first strand of DNA at a first portion of said first strand and a second double stranded structure between said second nucleoprotein primer and said second strand of DNA at a second portion of said second strand such that the 3' ends of said first extension blocked primer and said second nucleic acid primer are oriented toward each other on the same double stranded target nucleic acid molecule, wherein said nuclease specifically cleaves said modified noncomplementary internal residue only after the formation of said first double stranded structure to form a first 5' primer and a first 3' extension blocked primer; (d) extending the 3' end of said first 5' primer and second nucleoprotein primer with one or more polymerases and dNTPs to generate an amplified target nucleic acid molecule; (e) continuing the reaction through repetition of (c) and (d) until a desired degree of amplification is reached. As explained above, the first nucleic acid primer may be the first extension blocked primer, said second nucleic acid primer, first nucleoprotein primer or second nucleoprotein primer. Naturally, if the first primer is the first extension blocked primer, step (a) should be performed in the presence of the nuclease. Further, it should be noted that any RPA reaction which uses a single stranded nucleic acid target DNA as a starting material will necessarily go through an intermediate stage where the target nucleic acid is double stranded and would be amplified by double stranded amplification.

Another aspect of the invention is directed to a primer for RPA which is an extension blocked primer of between 12 to 100 residues in length and wherein the primer comprises one or more modified internal residues. This primer may be any of the extension blocked primer, including any variants thereof, described anywhere in this application. Briefly, the modified internal residue is selected from the group consisting of a uracil residue, an inosine residue, 8-oxoguanine, thymine glycol, an abasic site mimic and analogs thereof. The abasic site mimic may be a tetrahydrofuran residue or a 5'-O-Dimethoxytrityl-1',2'-Dideoxyribose-3'-[(2-cyanoethyl)-(N,N-diisopropyl)]-phosphoramidite (commonly known as a "D-spacer") and analogs thereof.

The primer is extension blocked and cannot be elongated by polymerase (e.g., Klenow fragment) and dNTP. Methods of blocking a primer from extension are known and are also described in this disclosure. Briefly, the primer may have a blocked 3' residue. The blocked 3' residue may be a blocking moiety. The blocking moiety, which optionally may comprise a detectable label, may be attached to the 2' or 3' site of the 3' most residue of the primer. For example, the blocked 3' residue may be a 2'3'-dideoxy nucleotide.

In another embodiment, the primer comprises one or more detectable labels. The detectable label may be a fluorophore, an enzyme, a quencher, an enzyme inhibitor, a radioactive label, one member of a binding pair and a combination thereof. In a more preferred embodiment, the primer comprises both a fluorophore and a quencher. The quencher may be close to the fluorophore to suppress the fluorescence of the fluorophore. For example, the separation between the fluorophore and the quencher may be 0 to 2 bases, 0 to 5 bases, 0 to 8 bases, 0 to 10 bases, 3 to 5 bases, 6 to 8 bases, and 8 to 10 bases. In a preferred embodiment, the fluorophore and quencher are separated by a greater distance when the extension blocked primer is unhybridized (but attached to recombinase and/or single stranded binding protein) than when the extension blocked primer is hybridized to the target nucleic acid. The fluorophore and quencher may be any fluorophore and quencher known to work together including, but not limited to, the fluorophore and quenchers any of the fluororophores described in this disclosure.

BRIEF DESCRIPTION OF THE DRAWINGS

FIG. 6. shows that UNG inhibitor peptide from *Bacillus* phage can be used in combination with *E. coli* UNG for a carry-over contamination system which avoids a need for thermal denaturation of UNG.

FIG. 7B discloses the probe sequence as SEQ ID NOS 64 and 81, respectively.

FIG. 10A discloses the sequence as SEQ ID NOS 93 and 94, respectively.

FIG. 13B discloses the sequence as SEQ ID NOS 95 and 96, respectively.

DETAILED DESCRIPTION OF THE INVENTION

Figure 1:
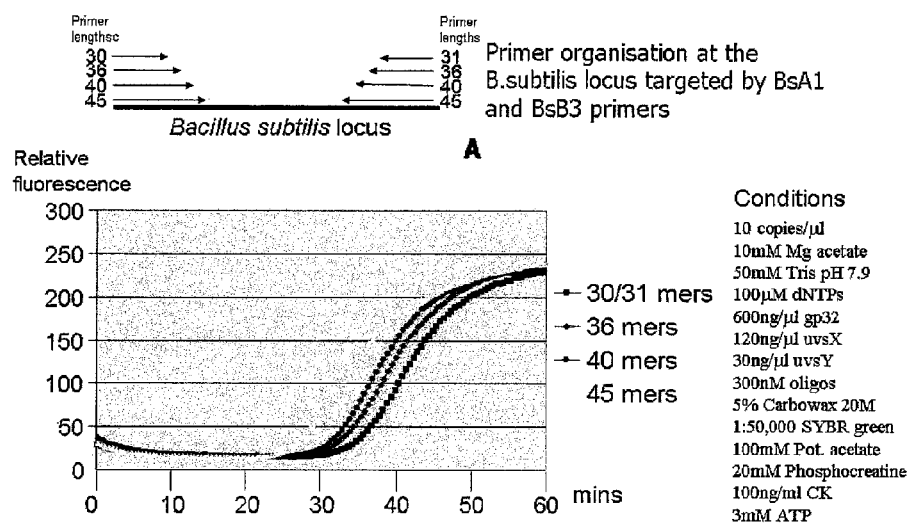
FIG. 1 depicts experimental data showing that lengthening primers accelerate reaction kinetics in the case of primers targeting a *Bacillus subtilis* genomic locus.

In RPA the isothermal amplification of specific DNA fragments is achieved by the binding of opposing oligonucleotide primers to template DNA and their extension by a polymerase (FIG. 1A). Unlike PCR, which requires global melting of the target template, RPA employs recombinase-primer complexes to scan double-stranded DNA and facilitate strand exchange at cognate sites. The resulting structures are stabilized by single-stranded DNA binding proteins (SSBs) interacting with the displaced template strand, thus preventing the ejection of the primer by branch migration.

Recombinase disassembly leaves the 3'-end of the oligonucleotide accessible to a strand displacing DNA polymerase in this case the large fragment of *B. subtilis* PolI (Bsu) (See, Okazaki et al., 1964), and primer extension ensues. Exponential amplification is accomplished by the cyclic repetition of this process.

In this disclosure, we showed a number of improvements over the basic RPA process. First, we found that with modifications to standard conditions, RPA may be performed efficiently at 25° C. or 30° C. These reaction temperatures allows for equipment-free RPA tests with results in under an hour.

Second, we improved the sensitivity and specificity of RPA reactions by using DNA repair enzymes in the RPA reaction. In this study, we employed a wide spectrum of previously identified repair enzymes directly in RPA reactions to see if these enzymes would have an effect on RPA efficiency and fidelity. We hypothesize that primer artifacts arise in RPA principally by errant extension of short-lived hairpin structures formed by the primers, or possibly by forming primer dimers (PCT Application PCT/IB2005/001560 filed Apr. 11, 2005). Although such events are presumably rare, the high concentration of oligonucleotide in a reaction, typically of the order $10^{12}$-$10^{13}$ molecules would tend to promote a significant degree of such events when the concentration of target template nucleic acid (i.e., the nucleic acid to be amplified) is low. It should be noted that these side reactions are distinct in nature from those often reported in PCR in which poorly-related sequences are amplified from complex DNA samples due to low fidelity of extension from hybridization products in which only a limited number of 3' residues are homologous to parts of the sample DNA. In RPA we believe that the primary recombinase-mediated pairing requires significant homology over significant regions, and rather that single-stranded DNA's are the species mainly sensitive to artifacts through snapback events occurring at the relatively low temperatures employed. Because of this distinction, methods for reducing primer artifacts in PCR do not necessarily work in RPA reaction. This distinction is important to comprehending the approach and mechanism described below for decreasing the background noise generated in the system even in the absence of any target nucleic acids, and the way in which this increases sensitivity by decreasing the competitive primer noise.

We disclose herein the use of primers deliberately modified with a 3'-blocking group (with a biotin, ddC residue, or otherwise), and additionally containing a roughly centrally positioned modified (or absent) base. The internally positioned modification became a nuclease target for a repair endonuclease enzyme, which could split the primer to generate two separate primers only if first paired to a target to generate a stable duplex, and then secondarily processed by the enzyme. If one of the new daughter primers (i.e. the most relatively 5' positioned) possesses, or can subsequently be processed to possess, a free extendable 3' hydroxyl group, then it could subsequently function as a polymerase substrate. In contrast the daughter oligonucleotide positioned relatively 3' would retain the original blocking modification and be unable to function as a polymerase substrate. A dependence on splitting the oligonucleotide to form two duplex hybrids separated by a nick or single-nucleotide gap adds noise reduction to the RPA system as there is little or no opportunity for the un-split primer to be erroneously extended in transient fold-back structures due to the presence of the 3' blocking group. We demonstrate the utility of this approach to reduce primer noise here by showing that trace DNA samples can be detected and discriminated from water merely by assessing whether two labeled DNA primers become physically linked. The possibility of such simple assays presents RPA as a powerful tool in the development of cheap, disposable, equipment-free DNA tests.

Finally we have adapted the above duplex-specific nuclease system to the development of proprietary real-time fluorescent probes. We anticipated that the design of effective fluorescent probes would be quite distinct in the RPA system in comparison to other described systems, such as in the PCR method. Why is this? We identified two key areas of difference. First, the organization of the functional groups on the probe would likely be necessarily different due to the extreme difference between RPA reaction environments and those of other amplification systems. Earlier work demonstrated that the RPA reaction environment was fundamentally and critically distinct from that encountered in other nucleic acid amplification reactions. Saturating quantities of single-stranded DNA binding protein and recombinase protein ensures that oligonucleotides with non-modified backbones do not adopt a random coil structure. DNA's are relatively 'stretched out' and rigid as these proteins imbue the nucleoprotein filament with a filament length roughly 1.5 times that of B-form DNA (Yang et al., 2001; Scheerhagen et al., 1985; Kuil M E et al., 1990). Consequently the supposition that probes covalently linked to fluorophores and quenchers distant in the primary sequence will still quench due to frequent random approach does not hold true. The second key area in which RPA probes were anticipated to be quite distinct form those in other described systems relates to the enzymes employed in probes processing. We discovered experimentally that described approaches using the 5' exonuclease domain of Pol I class enzymes appeared incompatible with RPA (so-called 'Taqman' method), likely due to FLAP endonuclease activity of these enzymes (Kaiser et al., 1999). We further anticipated that other systems such as molecular beacons or scorpion probes were similarly unlikely to be practical (due to the instability of short duplex anchors in RPA conditions). Instead, we here show that it is possible to configure excellent real-time RPA probes by placing fluorophore and quencher moieties close to one another separated by a modified base that leads to backbone splitting only in a duplex context. This approach promises to add tremendous value to the RPA process as it brings the real-time quantitative detection and multiplexing specifications into alignment with the current state-of-the-art using the other methods. Specifically it provides an approach to assess absolute numbers of target nucleic acid molecules in a sample, to increase specificity and sensitivity to allow single molecule detection, and also to permit multiplex analysis of several targets. All of these properties can be attained using this method without a need for gel electrophoresis, or other approaches requiring experimental intervention, but rather reactions can be monitored continuously and automatically by dedicated equipment. To illustrate the power of combining the RPA process with these highly fidelitous detection approaches we have developed an ultrasensitive, internally-controlled, test for the hospital pathogen MRSA, a difficult target due to the complex and diverse nature of pathogenic strains, and a need for multiplexing.

Each aspect of the invention is described in more detail below:

Low Temperature RPA

RPA reactions operate optimally at about 37° C., reflecting the temperature optimum of the enzymes involved in an RPA reaction. While 37° C. is easily achieved in the laboratory, an RPA reaction that can function efficiently at 30° C.

or 25° C. would increase the utility of RPA and allow real time amplification under field conditions where a 37° C. incubate in not available.

To determine if primer length has an effect on RPA efficiency, RPA reactions were performed at 37° C. with primer pairs of different lengths (FIG. 1). The results of the experiments, as shown in FIG. 1, shows that primer 'rates' can be enhanced by lengthening primers. Panel A of FIG. 1 shows the primer organization at the B. Subtilis locus targeted by BsA1 and BsB3 primers for RPA amplification. The primers BsA1 and BsB3 (30 and 31 residues respectively), or derivatives containing extensions which retain appropriate homolog with the target which were used in the RPA reactions. Panel B shows the results of amplification kinetics monitored in a BIOTEK Flx-800 microplate reader with heated stage set to 38° C. SYBR-green was employed to assess DNA accumulation. Precise reaction conditions and component concentrations are as follows: 10 copies/µl; 10 mM Mg acetate; 50 mM Tris pH 7.9; 100 µM dNTPs; 600 ng/µl gp32; 120 ng/µl uvsX; 30 ng/µl uvsY; 300 nM oligos; 5% Carbowax 20M; 1:50,000 SYBR green; 100 mM Pot. acetate; 20 mM Phosphocreatine; 100 ng/ml CK (creatin kinase); 3 mM ATP.

It is understood that the primers for any of the methods of the invention may be made from DNA, RNA, PNA, LNA, morpholino backbone nucleic acid, phosphorothioate backbone nucleic acid and a combination thereof. Combinations thereof in this case refer to a single nucleic acid molecule which may contain one or more of one base connected to one of more of another base. Preferred concentration of these molecules may be in the range of between 25 nM to 1000 nM. In one preferred embodiment, the primers may contain a non-phosphate linkage between the two bases at its 3' end and is resistant to 3' to 5' nuclease activity.

Our results show that there was a gradual increase in kinetic rate as the primers were lengthened. In fact lengthening the primers from 30/31-mers to 45-mers cut the amplification time to threshold detection by about 10 minutes, from roughly 35 minutes to 25 minutes under the conditions used here (10 mM magnesium, 5% carbowax 20M). Based on the results of this experiment, we conclude that primers with slow kinetics may be enhanced by increasing primer length.

We also investigated whether primer length has an effect on RPA performed in lower temperatures. RPA may not work at a lower temperature for at least two reasons. First, there can be a sudden and dramatic cessation of RPA reaction function below a certain temperature if, for example, one of the components of the reaction cease to function below a certain temperature. For example, the carbowax may go through a phase transition at a lower temperature and cease to function in the desired fashion. Second, the reaction rate may simply slow progressively so that doubling times lengthen, a reflection of slower enzyme catalysis and diffusion. In the second case, the primer 'rate' could be very important because the reaction would possibly be 'up-against-the-clock' with regard to exhaustion of reaction components such as ATP.

Figure 2:
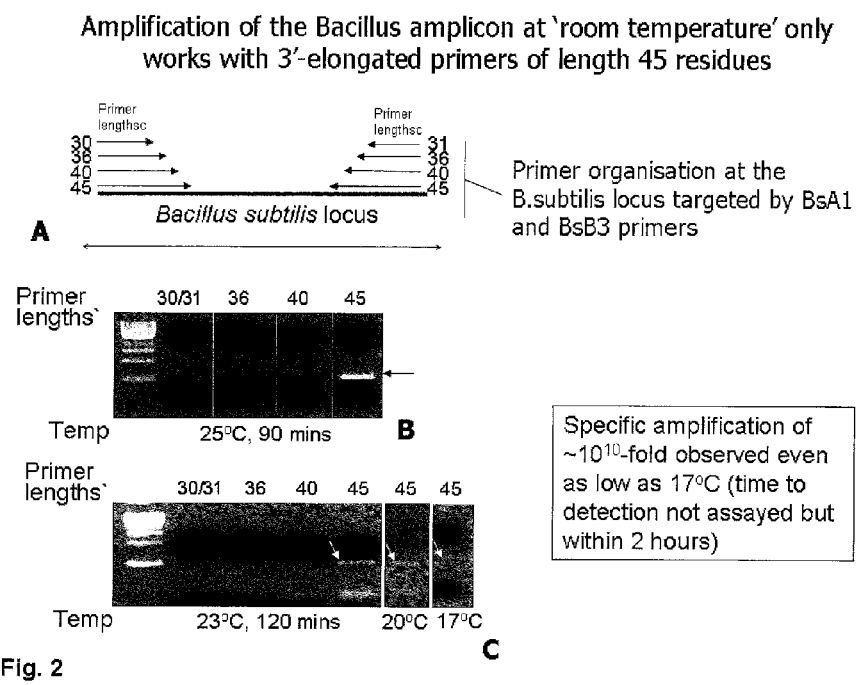
FIG. 2. depicts experimental results showing only the longer (45-mer) and faster primers successfully amplify DNA to gel detectable levels using ethidium bromide stain at 25° C., 23° C., 20° C., and 17° C.

To test our hypothesis, we attempted to amplify the same fragments as in FIG. 1 but at 25 oC. The results, shown in FIG. 2, indicate that primers with fast kinetics can amplify DNA at typical ambient (room) temperatures. The primers used in FIG. 1 were used to amplify a specific fragment from the B. subtilis genome. FIG. 2A shows the schematic arrangement of primers. FIG. 2B shows that only 45-mers amplify to detectable levels at 25° C. Conditions used were: 50 mM Tris pH 8.4, 100 mM Potassium acetate, 10 mM Magnesium acetate, 2 mM DTT, 7.5% PEG compound (Carbowax-20M), 3 mM ATP, 25 mM Phosphocreatine, 100 ng/µl creatine kinase, 700 ng/µl gp32, 160 ng/µl uvsX, 40 ng/µl uvsY, 200 µM dNTPs, 300 nM each oligonucleotide. Reaction time, 90 minutes. Start copy density 2 copies/µl, reaction volume 50 µl. FIG. 2C shows that only 45-mers amplify DNA at 23° C., and amplification to detectable levels can also occur at 20° C. and 17° C. when the 45-mer is used although progressively less amplification product was recovered. Conditions used: 50 mM Tris pH 8.4, 100 mM Potassium acetate, 14 mM Magnesium acetate, 2 mM DTT, 7.5% PEG compound (Carbowax-20M), 3 mM ATP, 50 mM Phosphocreatine, 100 ng/µl creatine kinase, 650 ng/µl gp32, 125 ng/µl uvsX, 40 ng/µl uvsY, 200 µM dNTPs, 300 nM each oligonucleotide. Reaction time, 120 minutes. Start copy density 1 copy/µl, reaction volume 20 µl.

As seen in FIG. 2, specific amplification of about $10^{10}$ fold observed even at temperatures at low as 17° C. The time to detection was within 2 hours. In the experiments performed at 23° C. or below only 20 copies of genomic DNA were added, and although some trace carry-over contamination had been in evidence from water controls (not shown), the attainment of visible product when using ethidium bromide stain (estimated 20 ngs at 17° C.) suggests an amplification level of around $10^9$-fold, or 30 cycles. Importantly high levels of 'noise' are not apparent, although we did observe one additional fast-migrating extra band of unidentified nature (quite possibly classical primer dimer, or single-stranded DNA related to the product).

Figure 3:
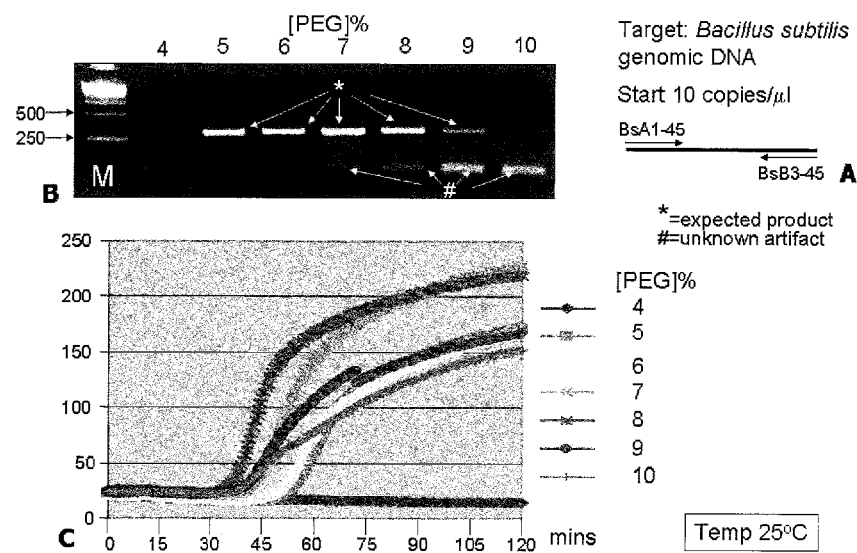
FIG. 3. depicts amplification kinetics at 25° C. appear roughly half those at 37° C. This figure also shows that PEG levels influence both rate and specificity (a primer artifact is increased at high PEG concentrations).

The kinetic behavior of the 45-mer primers at 25° C., under different concentrations of PEG, is shown in FIG. 3. In FIG. 3, the 45-mer primers used in FIGS. 1 and 2 were used to amplify a fragment of the B. subtilis genome at 25° C. FIG. 3A shows the arrangement of the primer pair used. FIG. 3B shows agarose gel electrophoresis and ethidium bromide staining of samples at reaction endpoint. The expected band (*) is accompanied by an additional band at higher PEG concentrations (#). FIG. 3C shows the kinetics of the amplification reaction monitored using SYBR-green. Conditions used was as follows: 50 mM Tris pH 8.4, 100 mM Potassium acetate, 10 mM Magnesium acetate, 2 mM DTT, PEG compound (Carbowax-20M) as indicated, 3 mM ATP, 25 mM Phosphocreatine, 100 ng/µl creatine kinase, 650 ng/µl gp32, 160 ng/µl uvsX, 40 ng/µl uvsY, 200 µM dNTPs, 300 nM each oligonucleotide, SYBR-green 1:50,000 from stock. Reaction time, 120 minutes. Start copy density 10 copy/µl, reaction volume 50 µl.

The lack of a signal in the 4% lane is possibly due to experimental error. The results show that higher PEG concentrations can accelerate kinetics up to a point, and then some inhibition in rate and overall reaction behavior/outcome is observed. In this case 7% or 8% PEG were optimal for maximizing the amount of amplified nucleic acids of the correct length. When the PEG concentrations are higher, there is progressive domination of the faster-migrating anomalous band. In the presence of 8% PEG detection was observed by about 37 minutes at 25° C., which corresponds to a doubling time of around 1 minute 25 seconds. At 5% PEG detection was made at about 54 minutes (corresponding to a 2 minutes doubling time). This reaction at 25° C. is about half as fastas the experiment shown in FIG. 1 (detection time of 27 minutes and doubling time of 1 minute. Based on this, we estimate RPA reaction rates halve with roughly every 10° C. drop in temperature. Further, due to limited pools of reagents such as ATP, detectable product formation may be limited regardless of incubation time depending on the temperature, activity of the primers, and product length. Our results suggest that effective low temperature RPA would be improved with primers that show fast kinetics, and which are not rate limiting in the reaction.

Figure 4:
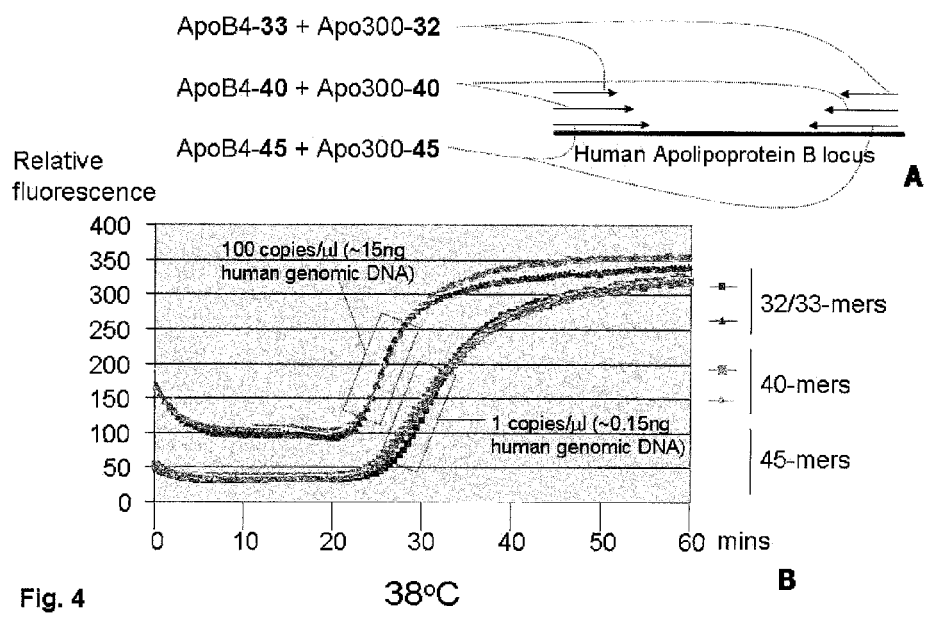
FIG. 4. shows that primers for the Human ApolipoproteinB locus, ApoB4 and Apo300, demonstrate rapid kinetics when only 33 and 32 residues respectively in length, and reaction kinetics (at 37° C.) are not accelerated by elongation.

The experiment of FIG. 3 was repeated using primers targeting the human Apolipoprotein B gene and the results are shown in FIG. 4. FIG. 4A shows the arrangement of primers targeting the human Apolipoprotein B locus. Three primer pairs were used as shown, and overlapping primers shared a common 5' extremity but different 3' ends. (B) Kinetics of amplification at 38° C. Reactions with the indicated primer pairs were monitored in real-time using SYBR-green dye. Start target copy numbers were either 1 copy/µl or 100 copies/µl of human DNA. Reaction conditions were as follows: 50 mM Tris pH 7.9, 100 mM Potassium acetate, 10 mM Magnesium acetate, 2 mM DTT, 5% PEG compound (Carbowax-20M), 3 mM ATP, 25 mM Phosphocreatine, 100 ng/µl creatine kinase, 600 ng/µl gp32, 120 ng/µl uvsX, 30 ng/µl uvsY, 100 µM dNTPs, 300 nM each oligonucleotide, SYBR-green 1:50,000 from stock. Reaction time, 60 minutes. Reaction volume 50 µl.

Figure 5:
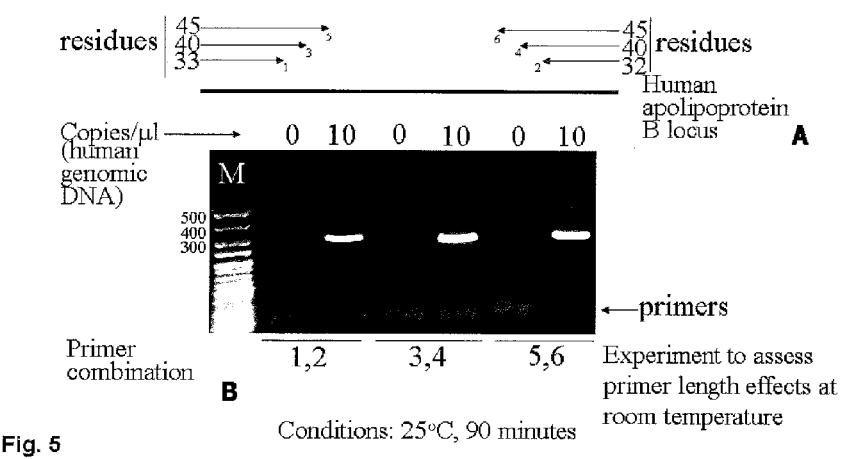
FIG. 5. shows that primers for the Human ApolipoproteinB locus, ApoB4 and Apo300, demonstrate amplification at 25° C. regardless of whether the 3' end is elongated.

Primers for the Human Apolipoprotein B locus show rapid kinetics without primer elongation. In this case kinetic studies using SYBR-green revealed that no rate increase was found with longer RPA primers. It appears that the ApoB4 and Apo300 primers used here, even when short, possess high rate behavior to the extent that they are not the rate limiting factor in the reaction. Presumably, in this reaction, polymerase rate is now the main rate-limiting part of the reaction and more active (longer) primers cannot achieve an overall speed benefit. Consistent with our hypothesis, we find that all of the Apolipoprotein B primers generate the expected product at 25° C. (FIG. 5). FIG. 5A is the same as FIG. 4A in that it shows the arrangement of the primers used. FIG. 5B shows gel electrophoresis of RPA reactions performed at 25° C. using the indicated primer pairs. Copy numbers of zero or 10 copies/µl were tested in each case. Conditions used were as in FIG. 4 with the exception of the omission of SYBR-green. In this case, no artifact band is seen—supporting the idea that RPA reactions do not significantly suffer from 'noise' at reduced temperatures.

Contamination Control Using UNG Inhibitor from Bacteriophage PBS2

RPA reactions are compatible with the use of dUTP as a method to control carry-over contamination. One caveat with the earlier experimental data is that in order to initiate the reaction the uracil glycosylase enzyme had to be heat inactivated. This poses two incompatibility issues with RPA. First, heat inactivation would also inactivate complete RPA reactions because RPA reagents are not heat stable. Second, heat inactivation is inconsistent with one goal of RPA—the avoidance of thermal cycling.

Because of the reasons above, we set to investigate another technical route to implement contamination control. It is known that the *Bacillus subtilis* phages PBS 1 (See, Savva and Pearl, 1995) and PBS2 (See, Wang, Z. and Mosbaugh, D. W. (1989)) possess a specific small peptide inhibitor of *E. coli* and *B. subtilis* uracil-DNA glycosylase (Wang and Mosbaugh, 1988). They require a highly effective system as their own DNA is synthesized using dUTP rather than dTTP. We cloned the PBS2 DNA sequencing encoding the inhibitor peptide and expressed it in *E. coli* with a C-terminal hexahistidine tag (SEQ ID NO:92). We also cloned the *E. coli* uracil glycosylase gene and expressed it with a C-terminal hexahistidine (SEQ ID NO:92). We used these protein preparations to test whether a carry-over contamination system could be employed with them. FIG. 6 shows an example of experiments performed which validate that such an approach. In FIG. 6, the start target copy numbers of the template were 800 copies of human DNA where used. Reaction conditions were as follows: 50 mM Tris pH 8.4, 100 mM Potassium acetate, 10 mM Magnesium acetate, 2 mM DTT, 5% PEG compound (Carbowax-20M), 3 mM ATP, 25 mM Phosphocreatine, 100 ng/µl creatine kinase, 600 ng/µl gp32, 125 ng/µl uvsX, 30 ng/µl uvsY, 100 µM dNTPs, 300 nM each oligonucleotide (SRY8 and SRY9 primers). Reaction time, 75 minutes. Reaction volume 50 µl. Where used *E. coli* UNG was used at 150 ng/µl, and UNG inhibitor was used at 140 ng/µl. Contamination was genuine carry-over contamination present for this amplicon in the laboratory liquid-handling equipment. Reactions were established with all amplification components apart from the polymerase. Reactions 1-4 carried genomic template DNA, reactions 5 and 6 contained only contaminating material. The samples were treated for 5 minutes with UNG in samples 2, 3, 4, and 6. In samples 2, 4, and 6 UNG inhibitor was added after 5 minutes. In all cases after the 5 minute incubation period, with or without UNG and with or without subsequent addition of UNG inhibitor, polymerase was added to initiate DNA synthesis. In this experiment we show the following: (1) that *E. coli* UNG will inhibit RPA reactions containing dUTP substrate, (2) that co-inclusion of the inhibitor peptide overcomes this inhibition, (3) that dUTP-containing contaminants can be suppressed from generating amplicons if first treated with *E. coli* UNG and then with the inhibitor, but that bona fide templates are still effective. Under the conditions used we have seen some evidence of some decrease in robustness/product level when UNG was present in the reaction. We anticipate however that the system may be configured more optimally.

Fluorescent Real-Time Probes for RPA Reactions

Many possible applications of the RPA process in detecting DNA (or RNA) sequences would benefit from being applied in a real-time format. RPA has already been shown to be effective when combined with minor groove binding dyes such as SYBR-green (PCT Application PCT/IB2005/001560 filed Apr. 11, 2005). However there may be potential limitations of using such general indicators of DNA accumulation to assess reaction behavior. First, there is no capacity for multiplexing amplification reactions as the dyes cannot discriminate between the various products formed. In many clinical tests, for example, there would be a need to include an internal amplification control to exclude false negatives. Second, RPA reactions are similar to most other DNA amplification processes insofar as even when no target is present in a sample, some DNA synthesis will eventually ensue. Consequently may be difficult or impossible to discriminate between the presences of a few copies of target nucleic acid or no copies of a nucleic acid based on current methods of florescent detection.

In response to these issues we have developed a proprietary fluorescence-based probe system to monitor RPA reactions. We investigated using the 5'-3' nuclease associated with the polymerases of the *E. coli* Pol I class. This nuclease is used in a fluorescent probe methodology for PCR known as the 5'nuclease, or 'Taqman', assay. We found that both *Bacillus subtilis* Pol I retaining the 5'-3' nuclease domain and the *E. coli* PolI enzyme would not support RPA reactions. On reflection we believe this arises because these nucleases are structural/functional homologs of the FEN1 FLAP endonuclease family and most likely are structure-specific endonucleases (Kaiser et al.). We suppose these enzymes progressively digest the displaced strand during the strand-displacement synthesis thus inhibiting DNA amplification.

We focused our attentions particularly on the *E. coli* glycosylase enzymes and AP endonucleases involved in DNA repair known as fpg, Nth, Nfo, and more recently *E. coli* exonuclease III. Importantly these enzymes will only remove damaged bases and/or nick DNA backbones at positions in which base modifications have occurred and, critically, in the context of duplex DNA. All of these enzymes are able to cleave such appropriate duplex DNA molecules with high specificity in the RPA environment (see application). Test probes were utilized that contained a modified base within the body of the oligonucleotide (8-oxoguanine, thymine glycol, or abasic site mimic respectively) and an additional distinct elongation blocking group on the 3' end (provided by a 3'-dR-biotin). Despite obvious promise for all of these enzymes, and potentially other repair/processing enzymes, we focused on the behavior of the *E. coli* Nfo and exonuclease III enzymes for the following reasons. First, we observed when testing fpg, Nth, and Nfo proteins that the degree of successful probe processing was highest for the probe containing a tetrahydrofuran residue (THF—an abasic site mimic), and processed by Nfo. Second, because Nfo, and the functionally similar *E. coli* exonuclease III, split the oligonucleotide into two smaller oligonucleotides separated by a single nucleotide gap, in which the new 3' end that is formed can be elongated by a strand displacing polymerase that can initiate at nicks. This property endows the THF/Nfo or THF/exonuclease III processing system with a wealth of application opportunities that extend beyond application to fluorescent probe processing. (Note that other abasic site mimics, or true abasic sites might also be employed).

A previous report has also illustrated a potential use of employing an abasic, or other blocking residue, in the context of an amplification process, with the preferred intention to remove the residue in the context of PCR or LCR reactions using a thermostable nuclease (U.S. Pat. No. 5,792,607, referred to herein as the '607 patent). However the approach we used is distinct from that of the '607 patent. In the '607 patent, an abasic site is described as one member of a broader selection of modifying groups, to be positioned preferentially at the 3' end of the intended amplification oligonucleotide, and designed to serve as a reversible 3' sugar modifying group by effectively preventing substrate recognition or catalysis by the polymerase. The intention is to decrease the propensity of the amplification system to amplify unintended targets in sample DNA because of the tendency of PCR and LCR techniques to form, albeit at reduced frequency, hybrids with sequences sharing limited homology to the 3'-region of oligonucleotide primers. Furthermore it is intended, critically, in the '607 patent that this modification preventing substrate recognition be specifically corrected in a target-dependent fashion. Such an activity might be performed by the activity of an agent such as endonuclease IV which can 'polish' groups from a 3' sugar residue. However, quite distinctly, in the process described herein the THF residue does not serve as an elongation-blocking modification agent to the 3' sugar that prevents the initial oligonucleotide/template hybrid being recognized as a bona fide substrate. Indeed the THF residue, instead of being located at the very 3' end of an oligonucleotide, is positioned within the body of the oligonucleotide, away from the substrate target of the polymerase (i.e. the 3' end region of the hybridized primer on the template DNA). In this disclosure the principal motivation is to prevent noise arising from primer fold-back artifacts. Thus, instead, herein the processing of the THF residue by an endonuclease activity leads to incision of the oligonucleotide backbone in the context of a bona fide duplex in a distinct event from 'correction' of the modification that prevents polymerase substrate recognition. We also describe herein 3' terminal elongation-blocking modifications, however these are not the 'corrected' modification in this case, and are not necessarily removed from 3'-terminal nucleotides as in the '607 patent. Instead, in the case described here we would employ two separable entities, a non-corrected 3'-blocking group, and a centrally located abasic-like residue which can be incised by an AP endonuclease to generate a nicked structure and two independent daughter annealed primers, only one of whom is a polymerase substrate.

Figure 7:
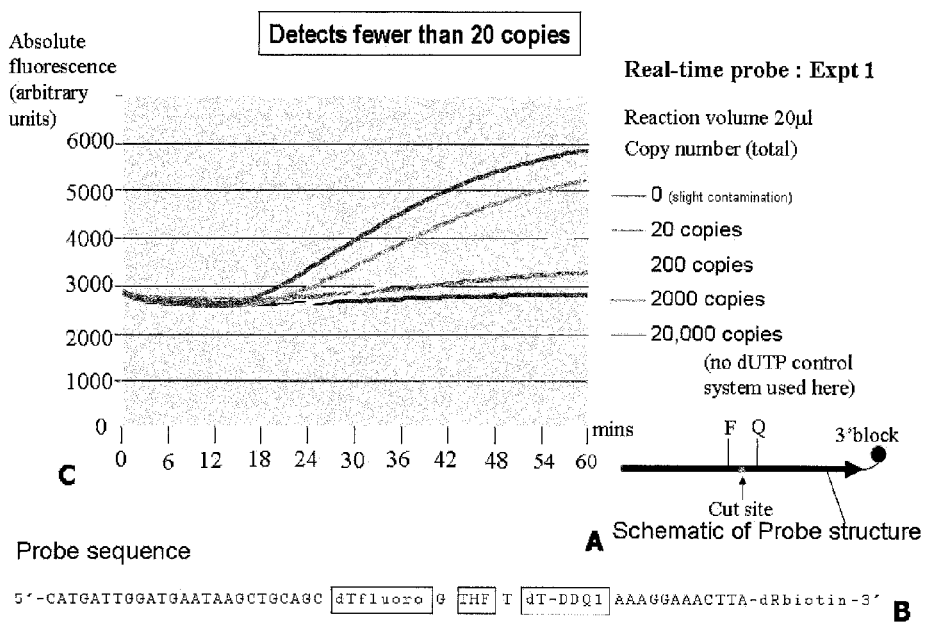
FIG. 7. depicts experimental data showing (a) A real-time detection probe comprising a FAM fluorophore, (b) a deep dark quencher, (c) an abasic site mimic, and (d) a blocked 3' end, provide excellent characteristics in RPA reactions for monitoring specific product accumulation.

FIG. 7 shows the results of an experiment in which a fluorescent sensing probe has been employed to assay for the accumulation of a specific amplicon in an RPA reaction. FIG. 7A shows a schematic structure of the probe. The probe has internal base-labeled fluorophore and quencher (fluorescein and deep dark quencher II) which were incorporated during synthesis by using commercially available (Glen Research, Sterling, Va., USA) fluorescein-dT or DDQ2-dT amidites.

A THF residue was inserted at a nucleotide position between these modified bases. The probe was blocked by the presence of a 3'-dR-biotin group. FIG. 7B shows the probe sequence which is:

```
                         (SEQ ID NOS 8 and 81, respectively)
5'-catgattggatgaataagctgcagc (dTfluoro) g (THF)
t (dT-DDQ1)aaaggaaactta-dRbiotin-3'
```

The probe is homologous to part of the *Bacillus subtilis* SpoOB locus contained within an amplicon generated by primers J1 and K2. The fluorophore and quencher were designed to be on T residues in the sequence so that they could be incorporated directly on commercially available amidites. FIG. 7C shows the amplification and probe cleavage kinetics as monitored by fluorescence increase. Amplification reactions were established with varying concentrations of target *Bacillus subtilis* genomic DNA. Reactions were established on ice and then incubated in a BIOTEK F1x800 microplate reader with stage set at 38° C. Amplification conditions are as follows: Start target copy numbers were as indicated. Reaction conditions: 50 mM Tris pH 7.9, 100 mM Potassium acetate, 12 mM Magnesium acetate, 2 mM DTT, 5% PEG compound (Carbowax-20M), 3 mM ATP, 25 mM Phosphocreatine, 100 ng/µl creatine kinase, 900 ng/µl gp32, 120 ng/µl uvsX, 30 ng/µl uvsY, 180 ng/µl Nfo, 100 µM dNTPs, 450 nM of K2 primer, 150 nM J1 primer, 100 nM probe. Reaction time, 60 minutes. Reaction volume 20 µl.

The sensing probe was designed to possess a fluorophore and quencher separated by (a) less than 10 bases (to ensure efficient quenching) and (b) a cleavable site (THF residue). In this case the primary amplicon was generated using the primers J1 and K2 to amplify a fragment from the *Bacillus subtilis* SpoOB locus. RPA reactions were modified from our usual conditions in the following manner. First the probe was included, whose overall structure and sequence is shown in the lower part of the figure. Second the amplification primers were biased in concentration so that there was a relative excess of the amplification primer opposing the probe in order that there might be a steady-state excess of complementary sequences to the probe. Finally the Nfo enzyme was included in the reaction. Reactions were performed in 20 microliter volumes in a standard 384-well plate and fluorescence monitored using excitation/detection filters of 485/525 in a BIO-TEK Flx800 plate reader. We observed that there was a template-dependent increase in fluorescence. The time at which accumulation begins was dependent on the copy number, as was the level of total fluorescence at the end of the period of reaction monitoring at one hour.

Figure 8:
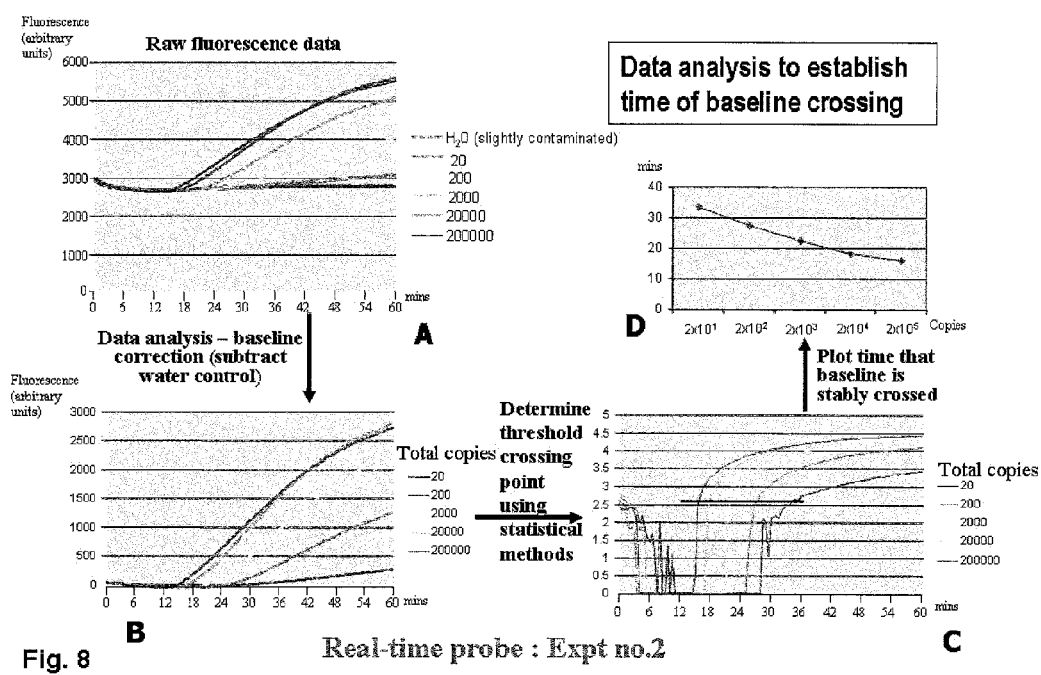
FIG. 8. depicts the development of a third probe detection system. Fluorescence data may be best interpreted through a process of normalization and plotting the log of fluorescence.

In FIG. 8 this experiment was repeated. FIG. 8A shows the raw fluorescence data while FIG. 8B shows normalized fluorescent signals. The fluorescence signal present in the water control at any given time was subtracted from all other sample fluorescence signals. All samples were normalized to one another by adjusting them to a common baseline based on the period prior to measurable fluorescence rise. In FIG. 8C, the log of the normalized fluorescence data was plotted and in FIG. 8D the time of threshold crossing of the fluorescence signal (set to about 2.6) was plotted against start copy number.

In this case we have shown the result of normalizing the samples against the signal in the water control, and then the results of plotting the logarithm of the normalized fluorescence signal. We set a fluorescence signal of 2.5 or above as constituting a positive signal. Note that it is easy to distinguish the low copy samples from water in contrast to the situation usually observed when using SYBR-green. The slight fluorescence increase in the water sample is almost certainly due to slight carry-over contamination associated with this particular amplicon which has been handled widely in the laboratory.

With respect to the quenchers of this disclosure, it is understood that a quencher need not be a fluorophore. A non-fluorescent chromophore can be used that overlaps with the donor's emission (a dark quencher). In such a case, the transferred energy is dissipated as heat.

High efficiency dark quenchers, such as Dark Quencher 1, Dark Quencher 2 and Black Hole Quencher 1 and Black Hole Quencher 2 are known and commercially available (Biosearch Technologies, Inc., Novato, Calif.). As is known in the art, the high quenching efficiency and lack of native fluorescence of the dark quencher allows attachment of a fluorophore and a quencher on one oligonucleotide and ensures that such an oligonucleotide does not fluoresce when it is in solution.

Suitable fluorophores and quenchers for use with the polynucleotides of the present invention can be readily determined by one skilled in the art (see also, Tgayi et al., Nature Biotechnol. 16:49-53 (1998); Marras et al., Genet. Anal.: Biomolec. Eng. 14:151-156 (1999)). Many fluorophores and quenchers are available commercially, for example from Molecular Probes (Eugene, Oreg.) or Biosearch Technologies, Inc. (Novato, Calif.). Examples of fluorophores that can be used in the present invention include, but are not limited to, fluorescein and fluorescein derivatives such as FAM, VIC, and JOE, 5-(2'-aminoethyl) aminonaphthalene-1-sulphonic acid (EDANS), coumarin and coumarin derivatives, Lucifer yellow, NED, Texas red, tetramethylrhodamine, tetrachloro-6-carboxyfluoroscein, 5 carboxyrhodamine, cyanine dyes and the like. Quenchers include, but are not limited to, DABSYL, 4'-(4-dimethylaminophenylazo)benzoic acid (DABCYL), 4-dimethylaminophenylazophenyl-4'-maleimide (DABMI), tetramethylrhodamine, carboxytetramethylrhodamine (TAMRA), Black Hole Quencher, Dark Quencher 1, and Dark Quencher 2. Methods of coupling fluorophores and quenchers to nucleic acids are well-known in the art.

We have successfully implemented a fluorescent probe system in the RPA reaction environment and established the general structure of probes. With this knowledge it should be easy to develop probes to detect any amplicon, and by judicious selection of alternate fluorophores, to multiplex more than one amplification at once. To demonstrate this we have developed a multiplex test for the antibiotic-resistant *S. aureus* pathogen known in the United Kingdom as methicillin-resistant *Staphylococcus aureus*, or MRSA for short.

The Detection of methicillin-resistant *Staphylococcus aureus*

MRSA comprises a collection of *Staphylococcus aureus* strains which have developed antibiotic resistance by integration of a resistance cassette, the mecA cassette, at a specific location in the *S. aureus* genome. While the same general genomic integration site is always used, the precise integration site junctions and orientation of the cassettes can vary. Despite this variation, independent isolates can be segregated into a limited number of general groups with representative integration structures. In addition to this complexity, further difficulties arise due to the existence of base polymorphisms between strains which can compromise the effectiveness of amplification primers and probes. The MRSA pathogen thus represents a complex target because in order to capture over 90% of the strains commonly found in clinical specimens in a single test it is necessary to accommodate detection of three structurally distinct variations of the mecA resistance cassette integration locus, and account for some common polymorphisms. Additionally, it is necessary that the amplicon spans one arm of the integration cassette to ensure that any mecA sequences amplified are in the context of the *S. aureus* genome, and were not present in an unrelated bacterium.

Figure 10:
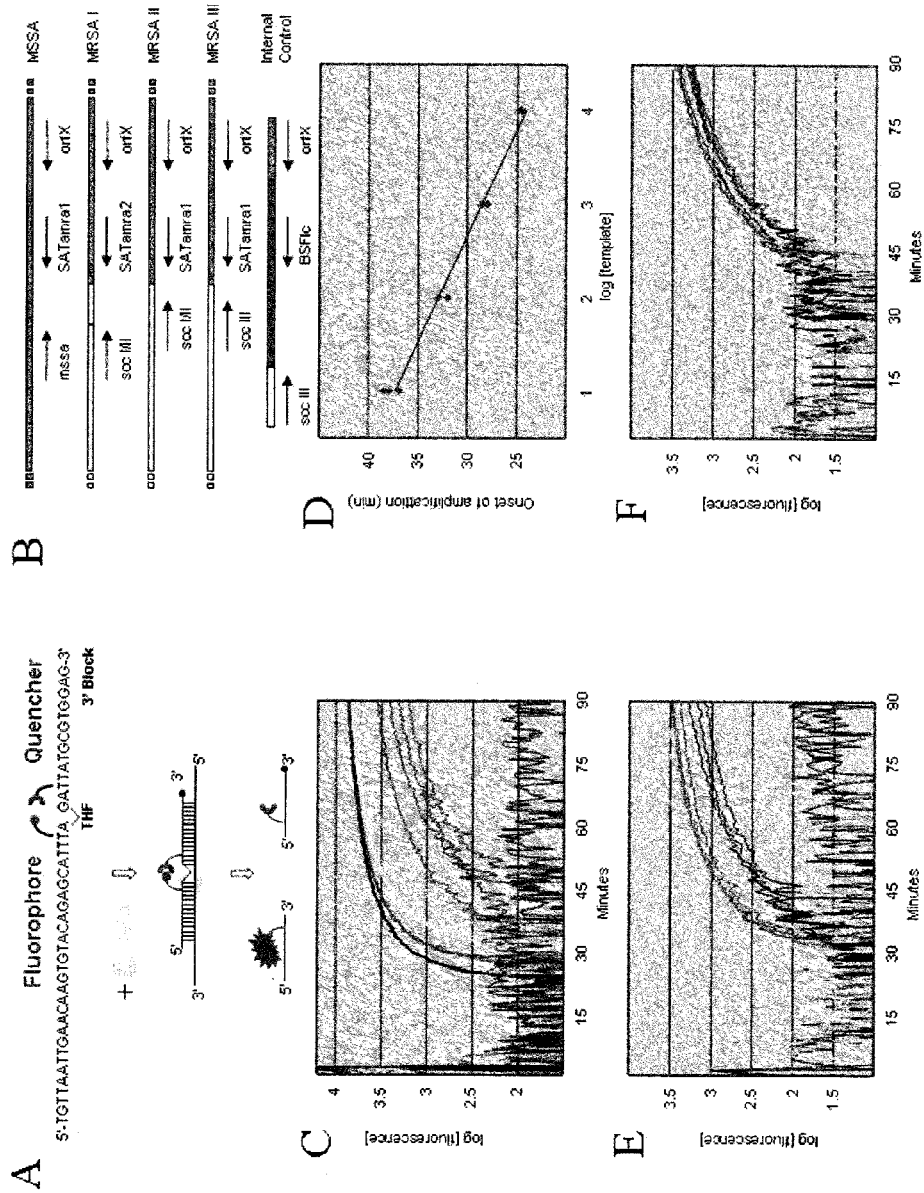
FIG. 10. depicts experimental results showing development of a dual-probe amplification/detection system for the hospital superbug MRSA.

In order to configure an RPA test for over 90% of common MRSA strains, we developed a primer design strategy which is illustrated in FIG. 10. FIG. 10 depicts the real-time detection of MRSA alleles in a multiplex test environment. FIG. 10A is a schematic of the RPA probe principle. Signal generation depends on probe cutting by double-strand specific Nfo. FIG. 10B depicts an arrangement of primers and probes relative to the targets used in 2C-F and 3C. A PCR fragment that fused an unrelated sequence to the target sites sccIII and orfX served as internal control. FIG. 10C shows probe signal of RPA reactions using the primer set orfX/sccIII. MRSAIII DNA at $10^4$ (black, reactions 1-3), $10^3$ (red, 4-6), 100 (yellow, 7-9), 10 (green, 10-12) or 2 copies (purple, 13-17) or water (blue, 18-20) served as template. FIG. 10D shows a plot of the onset time of amplification (defined as passing the 2.5 threshold) in reactions 1-12 in 2C against the logarithm of the template copy number reveals a linear relationship. (E) A multiplex RPA approach enables detection of different MRSA alleles and an internal control in the same reaction. MRSAI (green), MRSAII (dark blue), MRSAIII DNA (red) at 10 copies or MSSA DNA at $10^4$ copies (blue, negative control) or water (yellow, turquoise) served as a template (in triplicate for each template condition). (F) Detection of the 50 copies of internal control DNA included in the reactions in 2E. A negative control contained water (turquoise). The RPA reactions were performed as follows: Real-time RPA was performed in a plate-reader (BioTek Flx-800) in the presence of fluorophore/quencher probes. Reactions were performed at 37° C. for 90 minutes. Conditions were 50 mM Tris (pH 7.9), 100 mM Potassium-acetate, 14 mM Magnesium-acetate, 2 mM DTT, 5.5% Carbowax20M, 200 µM dNTPs, 3 mM ATP, 50 mM Phosphocreatine, 100 ng/µl Creatine-kinase, 20 ng/µl Bsu. Concentrations of gp32/uxsX/uvsY (in ng/ul) were 900/120/30. Primers were employed at 265 nM sccI/II, 265 nM sccIII, 70 nM orfX. Reaction volumes were 20 µl.

Three probes were employed:

```
SATamra1
           (SEQ ID NOS 9 and 82, respectively)
5'-tgttaattga acaagtgtac agagcatt (T)a(H)ga(q1)

tatgcgtgga g-Biotin-3'

SATamra2
           (SEQ ID NOS 10 and 83, respectively)
5'-tgttaattga gcaagtgtat agagcatt (T)a(H)ga(q2)

tatgcgtgga g-Biotin-3'

BSF1c
           (SEQ ID NOS 11 and 84, respectively)
5'-catgattgga tgaataagct gcagc (F)g(H)t(q3)

aaaggaaact ta-Biotin-3'
```

Here (T) is dT-TAMRA, (F) is dT-Fluorescein, (H) is THF, (q1) is dT-BHQ1, (q2) is dT-BHQ2, (q3) is dT-DDQ1. Probes were employed at 60 nM SATamra1 (MRSAIII experiment) or at 45 nM SATamra1, 45 nM SATamra2, 60 nM BSF1c (multiplex experiment). Nfo was used at 200 ng/ul. Excitation/detection was at 485/525 nm (SybrGreenI, BSF1c) or 530/575 nm (SATamra1/2). Measurements were taken every 30 sec or 45 sec (multiplex experiment). Fluorescence probe data were normalized against water control and pre-amplification baseline adjusted. The logarithm of the read-out was plotted against reaction time.

Briefly, a single primer was designed to recognize the *S. aureus* genomic DNA outside of the integration cassette region, and is termed orfX. Two further primers specific to the mec cassette were designed, and one of these (scc I/II) can be used to amplify the locus from two of the strain variants, while the second (scc III) amplified the locus from the third variant. Two probes for the amplicons are used, differing in two residues to account for common single nucleotide polymorphisms. Both these MRSA probes use TAMRA as fluorophore. Finally a control amplicon is included in the reaction which comprises a unique segment of an unrelated *B. subtilis* genomic DNA fragment fused to the orfx and sccIII primers, and a third probe may be used to sense this amplicon (BSF1c, and this is the same probe used in the experiments in FIG. 7, contains a fluorescein and deep dark quencher I). FIG. 10 part A illustrates once again the strategy for developing increased fluorescence in the reaction by processing of probes forming hybrids with amplicons. In Part C detection of one MRSA genomic DNA template is demonstrated over a wide concentration range in a non-multiplexed environment. Part E shows the results of an experiment in which (approximately) 10 copies of each of the three types of MRSA were separately detected using a single reaction mastermix. In part F the signal generated by the control sequence in the fluorescein channel is shown, and we can see that all those samples containing control DNA score positive.

Figure 11:
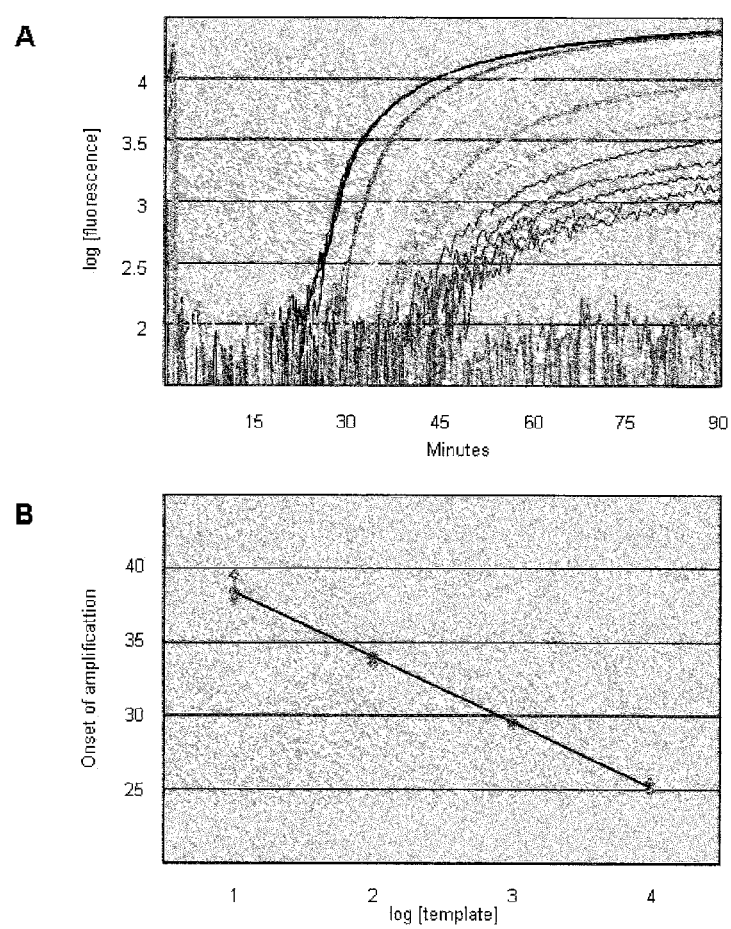
FIG. 11. depicts real-time probe-based detection of control MSSA DNA sequences.

Included in these experiments are control reactions containing relatively high concentrations of ($10^4$ copies) of non-resistant *S. aureus* DNA. Satisfyingly, these samples do not score positive indicating a strict requirement for both *S. aureus* sequences as well as the mecA cassette. To ensure that this control DNA was functional and that the copy concentration was as indicated, the DNA was used in control reactions employing a combination of the orfx primer and a second *S. aureus* specific primer termed mssa. In this case the same probes may be employed as the probes recognize common sections of the *S. aureus* genome. In FIG. 11 we can observe the results of an experiment performed with these non-resistant strain specific primers, and see how the control MSSA DNA is indeed effective, and shows appropriate response of the quantitative analysis to copy number. FIG. 11 depicts the detection of MSSA DNA in a real-time quantitative RPA reaction. Probe signal of RPA reactions using the primer set orfX/mssa and probe SATamra2. FIG. 11A depicts measurement of MSSA DNA at $10^4$ (black, reactions 1-3), $10^3$ (red, 4-6), 100 (yellow, 7-9), 10 (green, 10-12) or 2 copies (purple, 13-17) or MRSAI DNA at $10^4$ copies (grey, reactions 18-20) or water (blue, 21-23) served as template. Reaction conditions were 50 mM Tris (pH 7.9), 100 mM Potassium-acetate, 14 mM Magnesium-acetate, 2 mM DTT, 200 μM dNTPs, 3 mM ATP, 20 mM Phosphocreatine, 100 ng/μl Creatine-kinase, 5% Carbowax20M, 900 ng/μl gp32, 120 ng/μl uvsX, 30 ng/μl uvsY and 20 ng/μl Bsu. Oligonucleotides were employed at 500 nM mssa, 100 nM orfX and 60 nM SATamra2. Whilst the MSSA target is amplified even at very low concentrations, the negative control (MRSAI) does not generate a signal. FIG. 11B depicts a plot of the onset time of amplification (defined as passing the 2.5 threshold) in reactions 1-12 against the logarithm of the template copy number reveals a linear relationship.

Detection Of Trace Nucleic Acids by Association of Primers Following Enzymatic Generation of an Extendable 3' end RPA is ideally suited to the development of portable equipment-free, or equipment-light, DNA tests. However such tests would ideally employ cheap, easy-to-use, approaches to determine whether amplification has occurred. Traditionally gel electrophoresis is used to assess whether a product of a defined size has accumulated. Alternatively fluorescent probes may be employed. In either case significant hardware is required to perform the analysis and this prevents the test being used by end-users lacking appropriate equipment.

Other approaches may be used to determine whether or not DNA amplification has occurred. One convenient hardware-free approach is to perform a sandwich assay in which the presence of an amplicon is assessed by interrogating whether two labeled gene-specific primers have become associated in a common DNA duplex. This can be achieved by labeling one amplification primer with a label, such as biotin, and an opposing primer with a second label, such as FAM. A variety of approaches can be employed to determine whether the two labeled primers become associated. For example in a conventional lateral flow strip assay (see for example patent EP0810436A1), two antibodies (or other moiety such as streptavidin that binds with high affinity to one of the oligonucleotide labels) are employed. One antibody would be immobilized on a flow membrane in a line or spot. The other is coupled to visible particles such as colloidal gold, latex particles, or similar. When the sample, in this case a diluted or undiluted amplification reaction, is applied to a sample pad in which the antibody-coupled visible particles are pre-deposited, the visible particles become stably associated with one of the labeled oligonucleotides. The entire sample then moves by capillary action up the membrane and as it flows the other labeled primer becomes 'caught' on the immobilized antibody. If the labeled primers are not co-associated in a duplex then the antibodies 'caught' on the membrane are not associated with the visible particles associated with the other primer. If, however, they are associated as a consequence of amplification then the visible particles also become trapped on the line or spot, and a visible signal accumulates. Other approaches to assess for association of primers can be configured.

One problem with simple association assays, such as sandwich assays, is the requirement that the primers do not associate unless bona fide amplification of the desired target has occurred. Any undesired association will lead to a false positive signal. However such a clean-cut situation is rarely the case with most amplification methods, particularly when the target is not abundant. For example primer dimers, or other artifacts, tend to accumulate to some extent in the PCR method regardless of optimization. RPA also suffers from the accumulation of primer-related artifacts as detailed earlier, and these are likely to interfere with the direct combination of RPA with such simple read-outs. Indeed this general problem may underpin part of the reason that sandwich assays have not been broadly implemented in currently available high sensitivity/specificity DNA tests. Those commercially available lateral flow systems marketed to assess PCR product accumulation are inconvenient, requiring a final step of hybridizing an additional probe primer to the product after the reaction has been performed in order to avoid aberrant co-association of primers through DNA synthesis (e.g. The Genline *Chlamydia* Direct test strip from Milenia).

We have configured RPA reactions to permit easy assessment of bona fide target amplification by direct addition to lateral flow strips, or potentially by other similar methods. To attain a clean distinction between positive and negative samples we have employed a labeled primer which is split by the *E. coli* Nfo or exonuclease III enzymes to generate two primers, one of which may be elongated. This is attained by blocking the 3' end of the oligonucleotide, and separately incorporating a THF residue or product of employing a 5'-O-Dimethoxytrityl-1',2'-Dideoxyribose-3'-[(2-cyano-ethyl)-(N,N-diisopropyl)]-phosphoramidite during oligonucleotide synthesis, referred to herein as "D-spacer" available from Glen Research, Sterling, Va., USA) within the oligonucleotide to act as a splitting target for the enzyme. The dependence on formation of a stable duplex before the Nfo or exonuclease III enzymes will incise/split the primer ensures that aberrant association of this primer with the other labeled opposing primer does not occur, or is so infrequent as to fall below threshold of detection.

Figure 9:
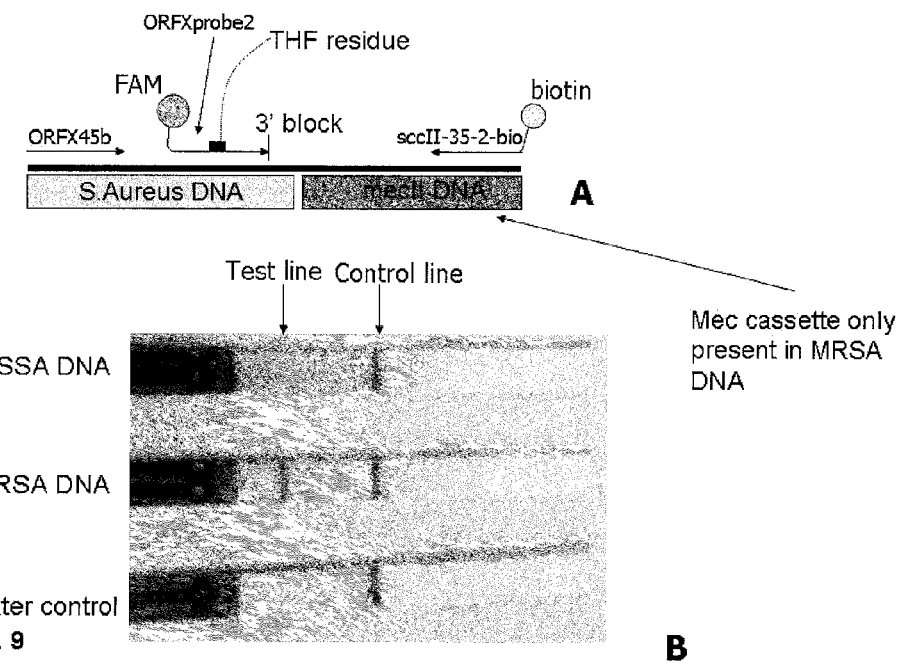
FIG. 9. depicts the use of reversibly blocked primers to gain high signal to noise ratios for sandwich assays. RPA reactions configured with a blocked, splittable, probe active only after splitting by Nfo enzyme can be analyzed directly on lateral flow test strips.

FIG. 9 shows data from experiment in which DNA from a methicillin-resistant *S. aureus* strain (EMRSA 16 strain containing the mec2 cassette), or from a non-resistant reference strain (MSSA) has been subjected to amplification in the presence of 3 primers. This experiment shows that a high signal to noise ratio amplification strategy suitable for lateral flow assays or other simple sandwich detection schemes is feasible. FIG. 9A shows a schematic of the arrangement of primers. The left-most primer, and the probe, recognize sequences present in the *S. aureus* genome, and similarly present in the *S. aureus* MSSA reference strain as well as the MRSA16 strain which contains a downstream mecII cassette insert. The right-most amplification primer is specific for sequences in the mecII cassette and is not found in the non-resistant *S. aureus* genome. The right-most primer is 5'-labelled with a biotin moiety, while the probe is labeled with a 5'-FAM moiety. The probe is blocked with 3' ddC, and contains an internal THF residue. In FIG. 9B, amplification reactions were established with the following conditions: 50 mM Tris pH 7.9, 100 mM Potassium acetate, 14 mM Magnesium acetate, 2 mM DTT, 5% PEG compound (Carbowax-20M), 3 mM ATP, 25 mM Phosphocreatine, 100 ng/µl creatine kinase, 600 ng/µl gp32, 125 ng/µl uvsX, 30 ng/µl uvsY, 270 ng/µl Nfo, 100 µM dNTPs, 100 nM of ORFX45b primer, 100 nM sccII-35-2-bio primer, 50 nM probe ORFXprobe2. Reaction time, 60 minutes. Reaction volume 304 Reaction temperature 37° C. Copy numbers were 1000 copies of MSSA DNA or 1000 copies of MRSA16 DNA, or water. After 60 minutes 1 µl of the reaction was diluted with 5 µl of PBS/3% Tween-20, and applied to the sample pad of a commercial lateral flow test strip from Milenia using 100 µl of PBS/3% Tween-20 (Milenia product: Genline hybri-detect MGHD1).

In this case 2 of the primers act as the main amplification primer pair, and a third acts as a probe. The probe contains a 3' blocking group and a separate internal THF residue to act as a splitting target, as well as a FAM label at the 5' end. The probe opposes one of the main amplification primers which is labeled with a biotin residue. Only if a bona fide amplicon accumulates will the probe form stable hybrids that are nicked/split by Nfo, elongated, and thus associate the 2 labeled primers. The results of an experiment are shown in which RPA amplifications established in this way were performed on DNA from the resistant and non-resistant strains. A small quantity of the reaction (1 µl) was then mixed with 5 µl of lateral flow running buffer (Phosphate buffered saline with 3% Tween-20) and directly applied to a commercial lateral flow strip (Milenia-germany). After about 1-2 minutes the strips were assessed for signal, and a photograph was taken. The test clearly distinguishes positive from negative.

Other processing enzymes might be employed in such approaches. In particular the *E. coli* fpg, Nth, and exonuclease III enzymes, homologs from other phyla, base mismatch repair enzymes such as *E. coli* MutY, MutS and MutM, *E. coli* MUG, Human MUG, Ogg1, and the vertebrate Nei-like (Neil) glycosylases. Any combination of the above repair enzymes might also be employed. In particular note that *E. coli* Nfo (endonuclease IV), and *E. coli* exonuclease III, possess phosphodiesterase activities and are capable of processing the non-extendable 3' ends of nicked products of the other glycosylase/lyases to extendable 3'-hydroxyl residues.

All patents, patent applications and references, cited anywhere in this disclosure, are incorporated by reference in their entirety.

The invention will now be described further by way of examples. The examples are illustrative of the invention and are not intended to limit it in any way.

EXAMPLE

Example 1

Nucleic Acid Sequences

Proteins and DNA

Coding sequences for uvsx, uvsy, gp32, Bsu and Nfo were amplified from genomic DNA (DSMZ, Germany), fused to hexahistidine-tags (SEQ ID NO:92) (N-terminal for uvsY, Bsu and Nfo, C-terminal for uvsX and gp32) and cloned into suitable expression vectors. Overexpression and purification was done by standard protocols using Nickel-NTA resin (Qiagen). *S. aureus* alleles were EMRSA-3 (SCCmec type I; MRSAI), EMRSA-16 (MRSAII), EMRSA-1 (MRSAIII) and wild-type MSSA. See additional sequence information provided below.

Primer sequences
Human locus ApoB (product size experiment S1):
Apo700
(SEQ ID NO: 12)
tggtaaacgg aagtctggca gggtgattct cg Apo800
(SEQ ID NO: 13)
caattgtgtg tgagatgtgg ggaagctgga at Apo900
(SEQ ID NO: 14)
gaggtggttc cattccctat gtcagcattt gc Apo1000
(SEQ ID NO: 15)
gggtttgaga gttgtgcatt tgcttgaaaa tc Human loci for STR markers (STR experiment and primer size experiment, SI):
CSF1PO
(SEQ ID NO: 16)
5' gttgctaacc accctgtgtc tcagttttcc tac CSF1PO
(SEQ ID NO: 17)
3' agactcttcc acacaccact ggccatcttc agc D7S820
(SEQ ID NO: 18)
5' gaacacttgt catagtttag aacgaactaa cg D7S820
(SEQ ID NO: 19)
3' gaattataac gattccacat ttatcctcat tgac D13S317
(SEQ ID NO: 20)
5' ttgctggaca tggtatcaca gaagtctggg atg D13S317
(SEQ ID NO: 21)
3' ccataggcag cccaaaaaga cagacagaaa ga D16S539
(SEQ ID NO: 22)
5' aaacaaaggc agatcccaag ctcttcctct tcc D16S539
(SEQ ID NO: 23)
5' ataccattta cgtttgtgtg tgcatctgta agc D18S51
(SEQ ID NO: 24)
5' ggtggacatg ttggcttctc tctgttctta ac D18S51
(SEQ ID NO: 25)
3' ggtggcacgt gcctgtagtc tcagctactt gc THO1
(SEQ ID NO: 26)
5' tacacagggc ttccggtgca ggtcacaggg a THO1
(SEQ ID NO: 27)
3' ccttcccagg ctctagcagc agctcatggt gg TPOX
(SEQ ID NO: 28)
5' actggcacag aacaggcact tagggaaccc TPOX
(SEQ ID NO: 29)
3' ggaggaactg ggaaccacac aggttaatta Human loci ApoB, D18S51 and Sry (primer size experiment, SI):
APOB500
(SEQ ID NO: 30)
atggtaaatt ctggtgtgga aaacctggat gg APO500-28
(SEQ ID NO: 31)
taaattctgg tgtggaaaac ctggatgg APO500-25
(SEQ ID NO: 32)
attctggtgt ggaaaacctg gatgg APOB300REV
(SEQ ID NO: 33)
ctatccaaga ttgggctaaa cgtatgaaag ca APOB300REV-28
(SEQ ID NO: 34)
ccaagattgg gctaaacgtatgaaagca APOB300REV-25
(SEQ ID NO: 35)
agattgggct aaacgtatga aagca D18S515'-28
(SEQ ID NO: 36)
gacatgttgg cttctctctg ttcttaac D18S51 5'-25
(SEQ ID NO: 37)
atgttggctt ctctctgttc ttaac D18S51 3'-28
(SEQ ID NO: 38)
gcacgtgcct gtagtctcag ctacttgc D18S51 Y-25
(SEQ ID NO: 39)
cgtgcctgta gtctcagcta cttgc SRY3
(SEQ ID NO: 40)
aaagctgtaa ctctaagtat cagtgtgaaa c SRY3-28
(SEQ ID NO: 41)
gctgtaactc taagtatcag tgtgaaac SRY3-25
(SEQ ID NO: 42)
gtaactctaa gtatcagtgt gaaac SRY4
(SEQ ID NO: 43)
gttgtccagt tgcacttcgc tgcagagtac c SRY4-28
(SEQ ID NO: 44)
gtccagttgc acttcgctgc agagtacc SRY4-25
(SEQ ID NO:45)
cagttgcact tcgctgcaga gtacc DNAs Used in this Disclosure BsA1
(SEQ ID NO: 46)
ttgggcactt ggatatgatg gaactggcac BsA1-36
(SEQ ID NO: 47)
ttgggcactt ggatatgatg gaactggcac ggttgt -continued BsA1-40
(SEQ ID NO: 48)
ttgggcactt ggatatgatg gaactggcac ggttgttgcg BsA1-45
(SEQ ID NO: 49)
ttgggcactt ggatatgatg gaactggcac ggttgttgcg tccat BsB3
(SEQ ID NO: 50)
ccatcttcag agaacgcttt aacagcaatc c BsB3-36
(SEQ ID NO: 51)
cgccatcttc agagaacgct ttaacagcaa tccatt BsB3-40
(SEQ ID NO: 52)
cgccatcttc agagaacgct ttaacagcaa tccattttgc BsB3-45
(SEQ ID NO: 53)
cgccatcttc agagaacgct ttaacagcaa tccattttgc gccag ApoB4
(SEQ ID NO: 54)
cagtgtatct ggaaagccta caggacacca aaa ApoB4-40
(SEQ ID NO: 55)
cagtgtatct ggaaagccta caggacacca aaataacctt ApoB4-45
(SEQ ID NO: 56)
cagtgtatct ggaaagccta caggacacca aaataacctt aatca Apo300
(SEQ ID NO: 57)
tgctttcata cgtttagccc aatcttggat ag Apo300-40
(SEQ ID NO: 58)
tgctttcata cgtttagccc aatcttggat agaatattgc Apo300-45
(SEQ ID NO: 59)
tgctttcata cgtttagccc aatcttggat agaatattgc tctgc SRY8
(SEQ ID NO: 60)
ccagctgtgc aagagaatat tcccgctctc cg SRY9
(SEQ ID NO: 61)
cctgttgtcc agttgcactt cgctgcagag t J1
(SEQ ID NO: 62)
acggcattaa caaacgaact gattcatctg cttgg K2
(SEQ ID NO: 63)
ccttaatttc tccgagaact tcatattcaa gcgtc NfoI probe
(SEQ ID NOS 64 and 85, respectively)
5'-catgattgga tgaataagct gcagc-[dTfluorescein]

-g-[tetrahydrofuranyl]-t-[dT-DDQ1]-aaaggaaact ta-dRbiotin-3'

ORFX45-b
(SEQ ID NO: 65)
ccaagaattg aaccaacgca tgacccaagg gcaaagcgac tttgt

ORFXprobe2
(SEQ ID NOS 66 and 86, respectively)
5'-(FAM)-CCACATCAAATGATGCGGGTTGTGTTAAT-[d-

SPACER]-GAACAAGTGTACAGAG-3'ddC (block)

SATamra1
(SEQ ID NOS 67 and 87, respectively)
5'-tgttaattga acaagtgtac agagcatt-[dT tamra]a (THF)ga(BHQ1)tatgcgtggag-Biotin-3'.

SATamra2
(SEQ ID NOS 68 and 88, respectively)
5'-tgttaattga gcaagtgtat agagcatt(dT tamra])a (THF)ga(BHQ2)tatgcgtgga g-Biotin-3'

BSF1c
(SEQ ID NOS 69 and 89, respectively)
5'-catgattgga tgaataagct gcagc (F)g(H)t(q3)

aaaggaaact ta-Biotin-3'

Sequence of MSSA and MRSA Alleles and Primers Used Here:

Primer target sites are bold/underlined, probe binding site is in bold/italic.
MRSA/MSSA primers (*S. aureus* experiment):
SCCI/II
(SEQ ID NO: 70)
ctcaaagcta gaactttgct tcactataag tattc SCCIII
(SEQ ID NO: 71)
ccaatatttc atatatgtaa ttcctccaca tctca ORFX
(SEQ ID NO: 72)
cccaagggca aagcgacttt gtattcgtca ttggcggatc aaacg MSSA
(SEQ ID NO: 73)
ccaatttgat agggcctaat ttcaactgtt agcta (SEQ ID NO: 74)
sccII-35-2-bio5'-bio-ctatgtcaaa aatcatgaac ctcattactt atgat MSSA DNA sequence:
(SEQ ID NO: 75)
ttttagatat aaaccaattt gatagggcct aatttcaact gttagctact acttaagtta tatgcgcaat tatcgtgata tatcttatat attgaatgaa cgtggattta atgtccacca tttaacaccc tccaattat tatctcctca tacagaattt tttagtttta cttatgatac gcct *ctccac gcataatctt*

*aaatgctcta tacacttgct caattaaca* c aacccgcatc

-continued atttgatgtg ggaatgtcat tttgctgaat gatagtgcgt agttactgcg ttgtaagacg tccttgtgca ggccgtttga tccgccaatg acgaatacaa agtcgctttg cccttgggtc atgcg

MRSAI DNA sequence:
(SEQ ID NO: 76)
tttagttgcagaaagaattttctcaaagctagaactttgcttcact ataagtattcagtataaagaatatttcgctattatttacttgaaat gaaagactgcggaggctaactatgtcaaaaatcatgaacctcatta cttatgataagctt *ctccacgcataatcttaaatgctct*

*atacacttgctcaattaaca* caacccgcatcatttgatgtgg gaatgtcattttgctgaatgatagtgcgtagttactgcgttgtaa gacgtccttgtgcaggccgtttgatccgccaatgacgaatacaaa gtcgctttgcccttgggtcatgcg

MRSAII DNA sequence:
(SEQ ID NO: 77)
tttagttgcagaaagaattttctcaaagctagaactttgcttcac tataagtattcagtataaagaatatttcgctattatttacttgaa atgaaagactgcggaggctaactatgtcaaaaatcatgaacctca ttacttatgataagcttcttaaaaacataacagcaattcacataa acctcatatgttctgatacattcaaaatccctttatgaagcggct gaaaaaccgcatcatttatgatatgctt

*ctccacgcataatcttaaatgctctgtacacttgttcatt*

*aaca* caacccgcatcatttgatgtgggaatgtcattttgctga atgatagtgcgtagttactgcgttgtaagacgtccttgtgcaggc cgtttgatccgccaatgacgaatacaaagtcgctttgcccttggg tcatgcg

MRSAIII DNA sequence:
(SEQ ID NO: 78)
aaggtataatccaatatttcatatatgtaattcctccacatctca ttaaatttttaaattatacacaacctaatttttagttttatttat gatacgctt *ctccacgcataatcttaaa*

*tgctctgtacacttgttcaattaaca* caacccgcatcatttg atgtgggaatgtcattttgctgaatgatagtgcgtagttactgc gttgtaagacgtccttgtgcaggccgtttgatccgccaatgacg aatacaaagtcgctttgcccttgggtcatgcg

Example 2

Kinetics of an RPA Reaction

Figure 12:
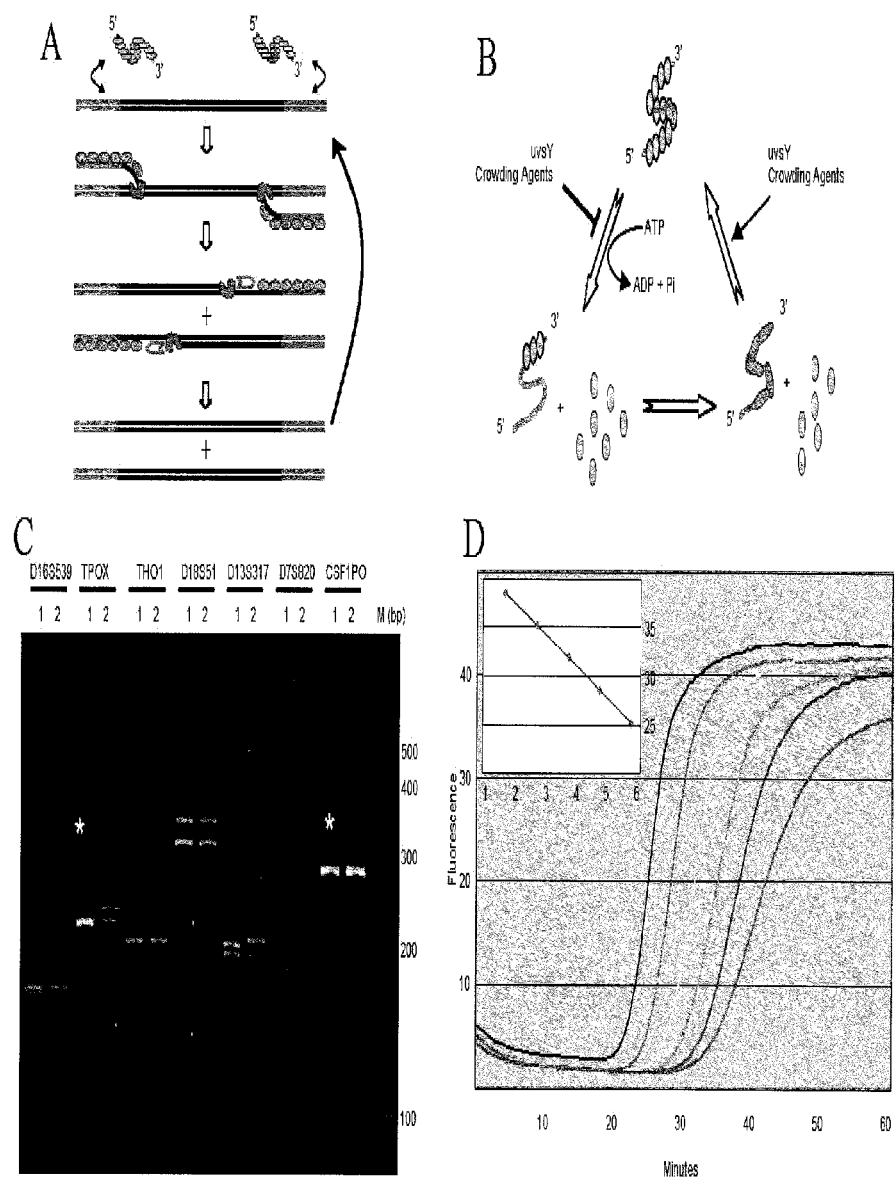
FIG. 12 depicts a schematic of an RPA process.

A schematic of the RPA process is shown in FIG. 12A. Recombinase/primer filaments scan template DNA for homologous sequences (red/blue). Following strand exchange the displaced strand is bound by gp32 (green), primers are extended by Bsu polymerase (blue). Repeated binding/extension events of opposing primers result in exponential DNA amplification.

The kinetics of recombinase/primer filament formation is shown in FIG. 12B. In the presence of ATP uvsX (grey) binds cooperatively to oligonucleotides (red, top). Upon ATP hydrolysis the nucleoprotein complex disassembles (left) and uvsX can be replaced by gp32 (green, right). The presence of uvsY and Carbowax20M shifts the equilibrium in favor of recombinase loading.

The result of a typical RPA reaction is shown in FIG. 12C which is a PAGE of RPA reactions using primers for STR markers. Genomic DNA from two individuals (½, father/son) served as template. Occasionally (D7S820, D16S539), low-level amounts of dimeric forms of full-length product can be observed (asterisks).

The ability to monitor RPA reaction in real time is shown in FIG. 12D. In FIG. 12D, a real-time RPA using primers for the *B. subtilis* SpoB locus was monitored by monitoring the fluorescence of a reaction. Fluorescence upon intercalation of SybrGreenI into nascent product is detected. *B. subtilis* DNA at $5\times10^5$ (black), $5\times10^4$ (red), $5\times10^3$ (yellow), 500 (green) or 50 copies (purple) or water (blue) served as template. The onset of amplification depends linearly on the logarithm of the starting template copy number (see inset; time (midpoint of growth curve) versus log [template concentration]).

Example 3

Detection of RPA Amplicons Using Lateral Flow Strips

Figure 13:
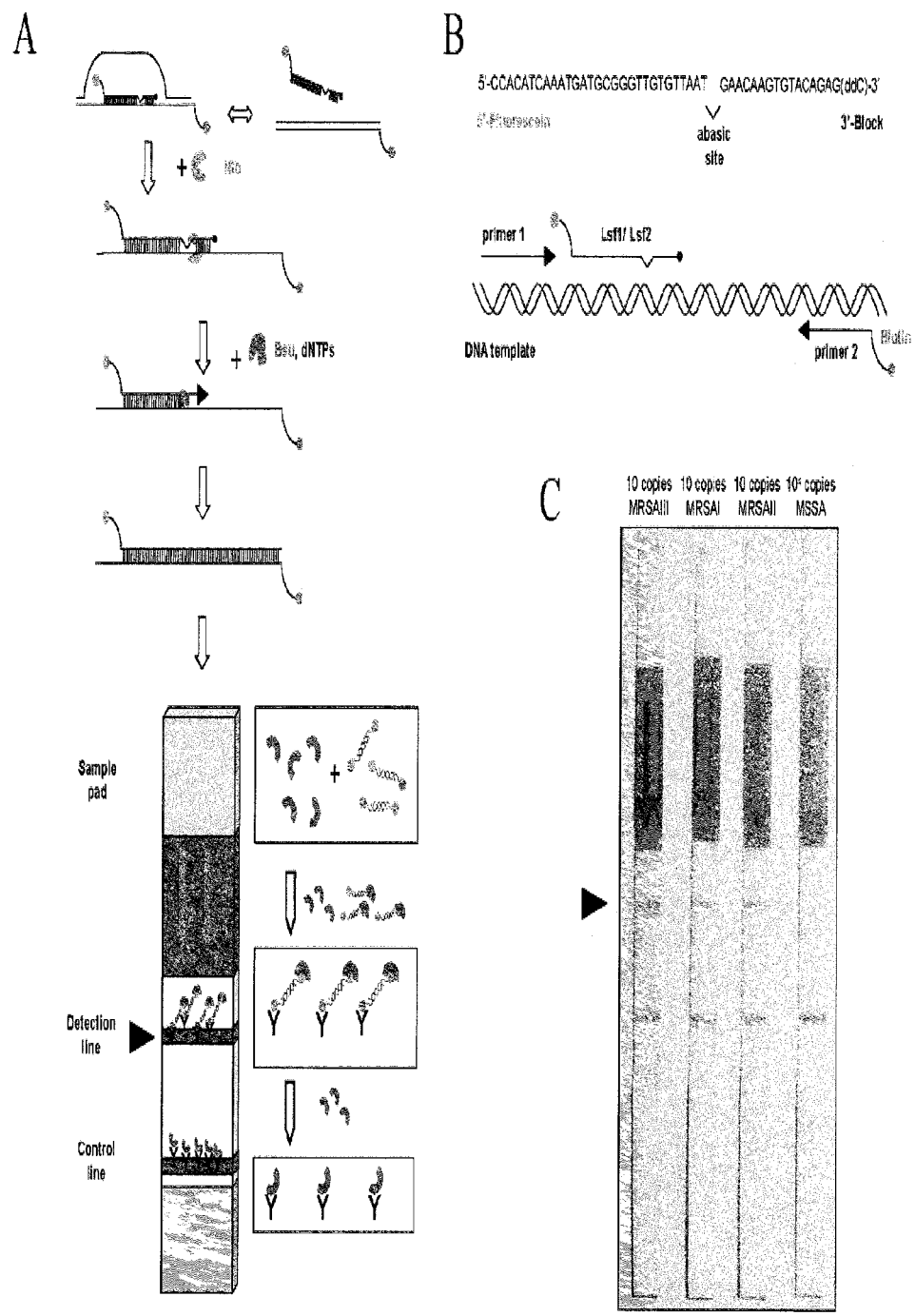
FIG. 13 depicts the use of specific antibodies to immobilize and detect complexes containing two antigenic labels on a flowstrip.

We devised a method of using lateral-flow-strip technology for the detection of RPA amplicon. This method uses specific antibodies to immobilize and detect complexes containing two antigenic labels (FIG. 13A). Briefly, a target nucleic acid is amplified using two different oligonucleotide primers, wherein each primer comprises a different label or antigen. Thus, all generated amplicons would be linked to two labels or antigens (i.e., a double labeled amplicon).

To detect the presences of the double labeled amplicons, samples suspected of containing the amplicons a pad soaked in visible (gold) particles coupled to an antibody recognizing one of the two labels (in this case, the label is an antigen) (FIG. 13C). The complexes then travel in a buffer stream through the membrane and an additional, immobilized antibody captures the second antigen (Id.). If the antigens are conjoined in a DNA duplex, a colored line appears at a defined location on the strip. In a variation of our probe detection system we produced such dual antigen complexes by coupling Biotin- and FAM-bearing oligonucleotides in RPA amplicons (FIG. 3B). The 5′-biotinylated primer and its opposing counterpart ensure the efficient amplification of a target for probe binding. The probe, including a 5′-FAM label, an internal THF and a 3′-blocking group, is incised by Nfo upon binding, creating a 3′OH substrate for elongation by Bsu. The extension of the probe remnant stabilizes its interaction with the Biotin-labeled strand and produces an amplicon that contains both, Biotin and FAM. The THF/3′block prevents the production of Biotin/FAM containing primer artifacts, as processing of bona fide duplexes by Nfo adds a critical proofreading step. After application of the sample to the lateral-flow-strip Biotin/FAM-amplicons will create a visible signal on the FAM detection line, while RPA reactions that fail to generate a conjoined complex will not. We used a multiplex approach similar to the one employed in FIG. 10E to detect 10 copies of each of the three MRSA alleles and distinguish them from MSSA (FIG. 3C).

A number of research and clinical applications could benefit from employing RPA and the various detection methods disclosed herein. For example, RPA offers a significant breakthrough for the development of non-laboratory devices. When integrated with handheld instruments or entirely equipment free DNA detection systems, RPA will enable an easy-to-use testing system for a variety of pathogens as well as field kits for other applications.

Materials and Methods

Proteins and DNA

Coding sequences for uvsx, uvsy, gp32, Bsu and Nfo were amplified from genomic DNA (DSMZ, Germany), fused to hexahistidine-tags (SEQ ID NO:92) (N-terminal for uvsY, Bsu and Nfo, C-terminal for uvsX and gp32) and cloned into suitable expression vectors. Overexpression and purification was done by standard protocols using Nickel-NTA resin (Qiagen).

Human DNA was purified from blood (Wizard-Genomic-purification-kit, Promega), B. subtilis DNA was from ATCC (USA), S. aureus DNAs were a gift from Jodi Lindsay. S. aureus alleles were EMRSA-3 (SCCmec type I; MRSAI), EMRSA-16 (MRSAII), EMRSA-1 (MRSAIII) and wild-type MSSA (12). See supplementary information for sequences.

RPA Conditions

Reactions were performed at 37° C. for 60 min or as indicated. Standard conditions were 50 mM Tris (pH 8.4), 80 mM Potassium-acetate, 10 mM Magnesium-acetate, 2 mM DTT, 5% Carbowax20M, 200 μM dNTPs, 3 mM ATP, 20 mM Phosphocreatine, 100 ng/μl Creatine-kinase, 20 ng/μl Bsu. In contrast, MRSA amplifications were done at 50 mM Tris (pH 7.9), 100 mM Potassium-acetate, 14 mM Magnesium-acetate; in the multiplex experiment Carbowax20M was at 5.5%. Concentrations of gp32/uxsX/uvsY (in ng/ul) were 600/200/60 (STR experiment), 600/120/30 (B. subtilis experiment) or 900/120/30 (MRSA experiments). Primers were employed at 300 nM each, except in MRSA amplification, where 500 nM sccIII, 100 nM orfX (MRSAIII experiment) or 265 nM sccI/II, 265 nM sccIII, 70 nM orfX (multiplex experiment) or 240 nM BiosccI/II, 240 nM Bio-sccIII, 120 nM orfX (lateral-flow-strip experiment) have been used. Reaction volumes were 20 μl, except for the STR experiment (40 μl) and the B. subtilis experiment (50 μl).

Real-Time Monitoring

Real-time RPA was performed in a plate-reader (BioTek Flx-800) in the presence of SybrGreenI (1:50000, Molecular Probes) or fluorophore/quencher probes (Eurogentec). Three probes were employed:

```
SATamra1
            (SEQ ID NOS 67 and 87, respectively)
5'-tgttaattgaacaagtgtacagagcatt(T)a(H)ga(q1)

tatgcgtggag-Biotin-3'

SATamra2
            (SEQ ID NOS 68 and 88, respectively)
5'-tgttaattgagcaagtgtatagagcatt(T)a(H)ga(q2)

tatgcgtggag-Biotin-3'

BSF1c
            (SEQ ID NOS 69 and 89, respectively)
5'-catgattggatgaataagctgcagc(F)g(H)t(q3)

aaaggaaactta-Biotin-3'
```

Here (T) is dT-TAMRA, (F) is dT-Fluorescein, (H) is THF, (q1) is dT-BHQ1, (q2) is dT-BHQ2, (q3) is dT-DDQ1. Probes were employed at 60 nM SATamra1 (MRSAIII experiment) or at 45 nM SATamra1, 45 nM SATamra2, 60 nM BSF1c (multiplex experiment). Nfo was used at 200 ng/ul. Excitation/detection was at 485/525 nm (SybrGreenI, BSF1c) or 530/575 nm (SATamra1/2). Measurements were taken every 30 sec or 45 sec (multiplex experiment). Fluorescence probe data were normalised against water control and pre-amplification baseline adjusted. The logarithm of the read-out was plotted against reaction time.

Lateral-Flow-Strip Detection

For lateral-flow-strip experiments two probes were used at 75 nM each:

```
Lfs1
            (SEQ ID NOS 79 and 90, respectively)
5'FAM-ccacatcaaatgatgcgggttgtgttaat(H)gaaca agtgtacagag-ddC-3'

Lfs2
            (SEQ ID NOS 80 and 91, respectively)
5'FAM-ccacatcaaatgatgegggttgtgttaat(H)gagca agtgtatagag-ddC-3'
```

5'-biotinylated forms of sccI/II and sccIII were utilised as primers. For each reaction (20 ul) 1 ul was diluted with 5 ul running buffer (PBS/3% Tween) and applied directly to HybriDetect-strips (Milenia) according to manufacturer instructions.

The result of the lateral flow strip detection is shown in FIG. 13C. Reactions contained (left to right) 10 copies MRSAIII, 10 copies MRSAII, 10 copies MRSAI or 10000 copies MSSA (negative control) as template. Positive signals are generated in the first 3 reactions (arrowhead).

Example 4

Analysis of Optimal Conditions for RPA

RPA Conditions

Figure 14:
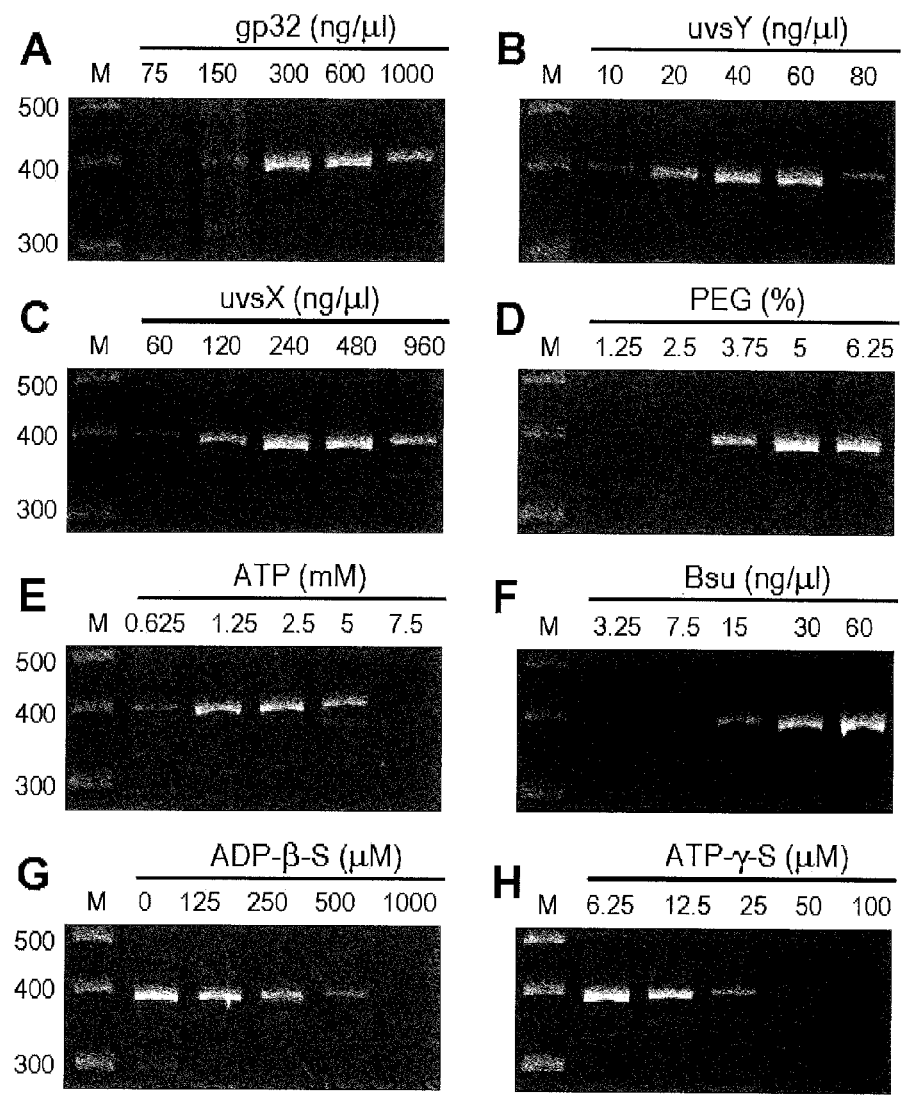
FIG. 14 shows polyacrylamide gel electrophoresis of RPA reactions using primers for the human Sry locus.

RPA relies on the establishment of a reaction environment that support the formation of recombinase-oligonucleotide complexes. Since the process is also ATPdependent (Formosa et al., 1986), it requires an energy regeneration system for sustained activity. In this experiment, we titrated key components of the RPA reaction mixture in order to determine their influence on amplification performance. The results are shown in FIG. 14. FIG. 14 shows polyacrylamide gel electrophoresis of RPA reactions using primers for the human Sry locus. Reactions were performed at 37° C. for 120 min and contained the primers sry3 and sry4 at 300 nM, 50 mM Tris (pH 8.4), 80 mM Potassium-acetate, 10 mM Magnesium-acetate, 2 mM DTT, 3 mM ATP, 200 μM dNTPs, 20 mM Phosphocreatine, 100 ng/μl Creatine-kinase, 5% Carbowax20M, 600 ng/μl gp32, 200 ng/μl uvsX, 60 ng/μl uvsY and 20 ng/μl Bsu, except when a given component was that under investigation. Optimal quantities of (FIG. 14 A) gp32, (FIG. 14 B) uvsY, (FIG. 14 C) uvsX, (FIG. 14 D) Carbowax20M, (FIG. 14 E) ATP and (FIG. 14 F) Bsu for effective amplification of this particular target were determined. (G) ADP-®-S and (H) ATP-©-S inhibit the reactions. 1500 copies/μl of the human Y-chromosomal DNA served as template in 30 ul reactions (per sample the equivalent of 10 ul reaction volume was loaded on the gel).

RPA proved to work robustly over a relatively wide range of reagent concentrations. We found, however, that optimal reaction conditions varied between different primer pairs and therefore had to be defined individually.

Primer Requirements

Figure 15:
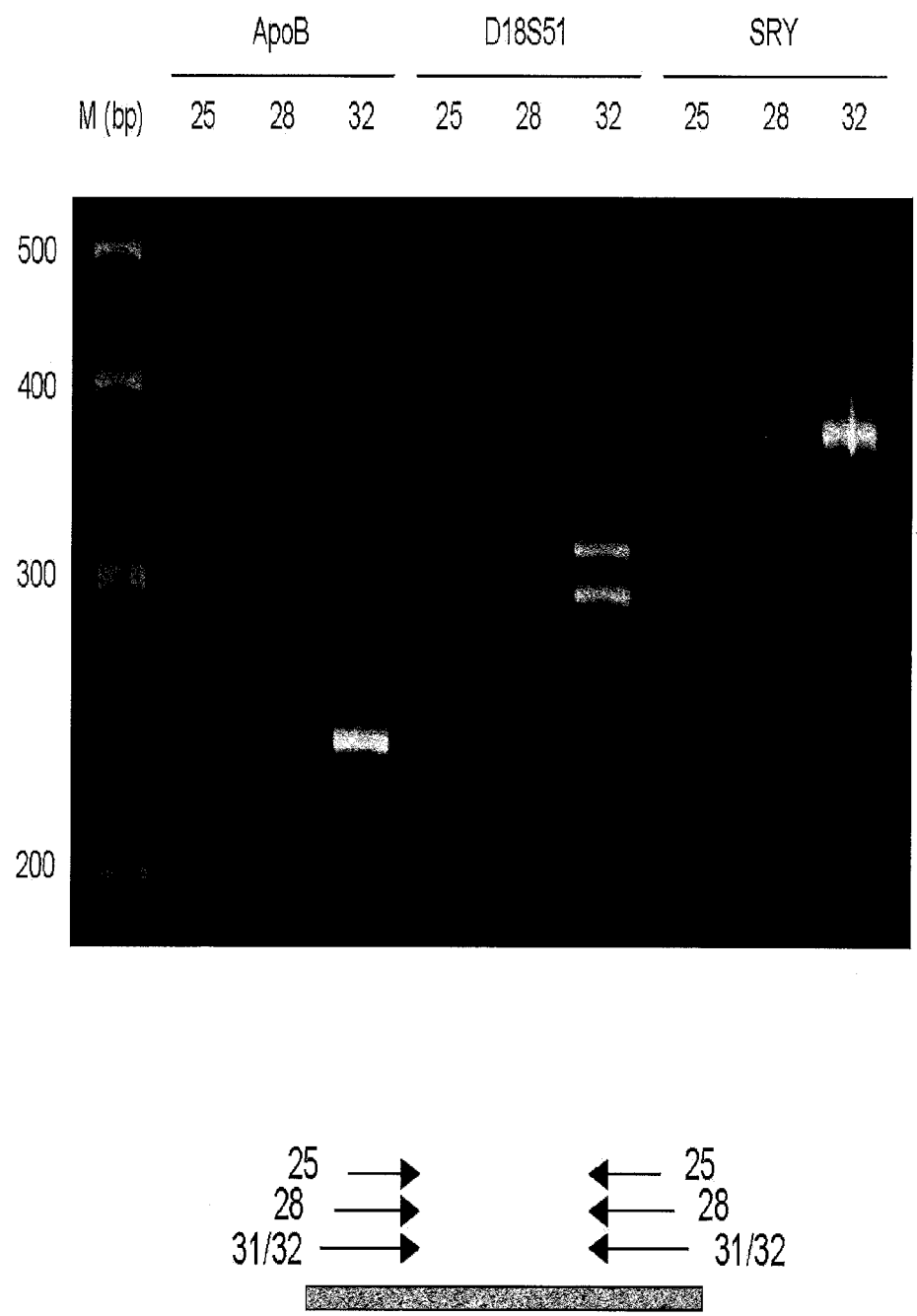
FIG. 15 shows agarose gel electrophoresis of RPA reactions using primers for the human Apolipoprotein B locus.

We used RPA to amplify of a wide range of targets. While the design of primers revealed no limitations on sequence composition itself, certain parameters have to be met for an oligonucleotide to be suitable for RPA. We investigated these parameters in the experiments shown in FIG. 15. FIG. 15 shows agarose gel electrophoresis of RPA reactions using primers for the human Apolipoprotein B locus. Primer ApoB4 was combined with opposing primers capable of generating products of the indicated sizes. Reactions were performed at 37° C. for 120 min and conditions used were 50 mM Tris (pH 8.4), 80 mM Potassiumacetate, 10 mM Magnesium-acetate, 2 mM DTT, 3 mM ATP, 200 µM dNTPs, 20 mM Phosphocreatine, 100 ng/µl Creatine-kinase, 5% Carbowax20M, 600 ng/µl gp32, 125 ng/µl uvsX, 25 ng/µl uvsY, and 20 ng/µl Bsu. 450 copies of human DNA were used as template in 30 µl reactions (per sample the equivalent of 10 ul reaction volume was loaded on the gel). Note that some hairpin-mediated product duplication occurred, converting some of the 300 bp amplicon to 2× and 3× unit length (*). RPA failed to produce amplicons of 1500 bp or more. This experiment shows that amplicon size under the conditions employed is limited to approximately 1 kb.

Shown is polyacrylamide gel electrophoresis of RPA reactions using primers for the three independent loci in human genomic DNA (Apolipoprotein B, STR D18S51, Sry). Primers were 25, 28, or >31 bases, as indicated. Reactions were performed at 37° C. for 120 min. Conditions used were 50 mM Tris/Cl pH 8.4, 80 mM Potassium acetate, 10 mM Magnesium-acetate, 2 mM DTT, 3 mM ATP, 2000 µM dNTPs, 20 mM Phosphocreatine, 100 ng/µl Creatine kinase, 5% Carbowax20M, 600 ng/µl gp32, 200 ng/µl uvsX and 60 ng/µl uvsY, and 20 ng/µl Bsu polymerase. 3000 copies of target served as template in 30 ul reactions (per sample the equivalent of 10 ul reaction volume was loaded on the gel). The finding that a primer length of >28 bases is required to support RPA is in good agreement with reports that investigated the ATP hydrolysis activity of uvsX-oligonucleotide filaments at different oligonucleotide sizes (See, Huletsky et al., 2004).

Figure 16:
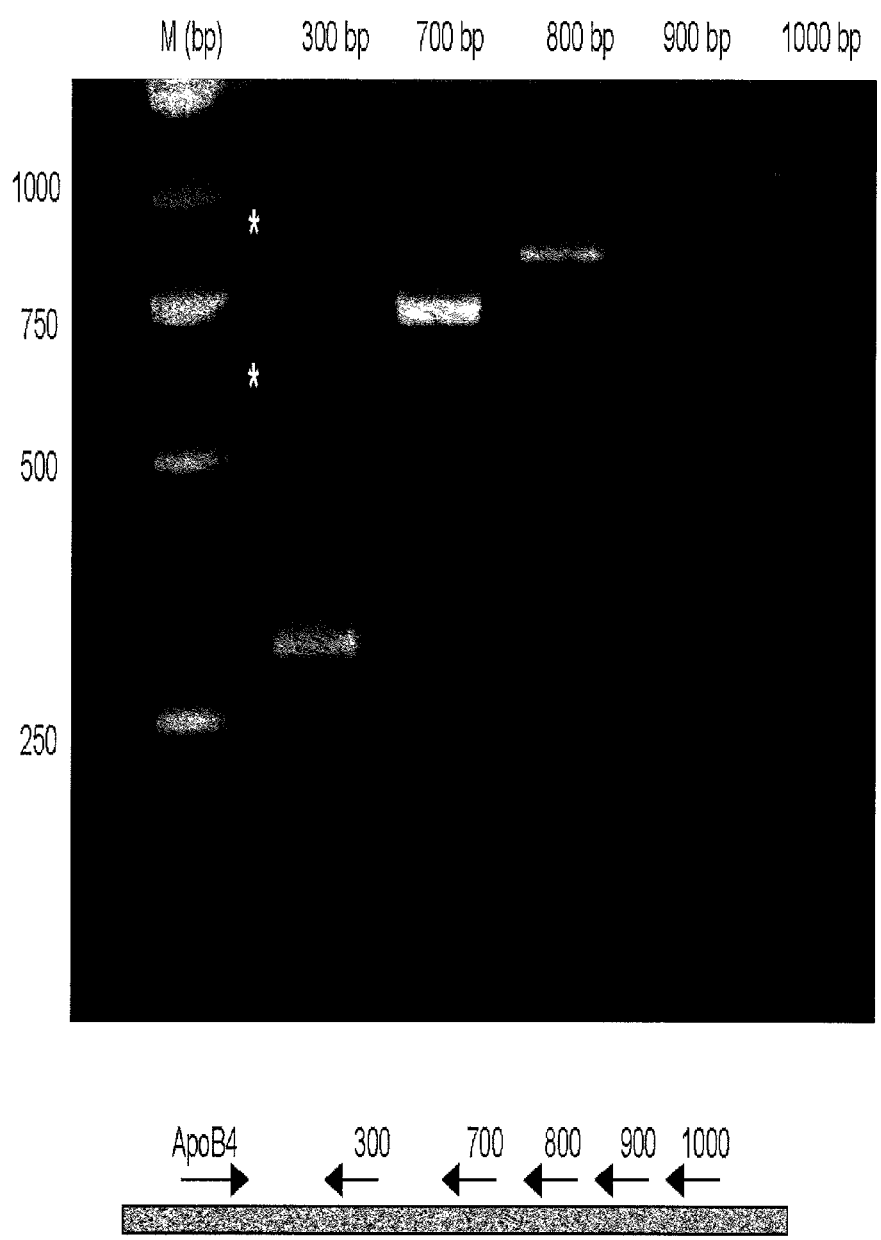
FIG. 16 depicts an investigation of the minimum oligonucleotides size necessary to support RPA

The minimum length of a primer proved to be about 30 nucleotides (FIG. 16). We observed variability in the performance of oligonucleotides that differ in sequences but are similar in length and position relative to their counterpart. The rules governing the influence of nucleotide sequence on the quality of a particular RPA primer are currently under investigation.

Control DNA

The wild-type *S. aureus* DNA (MSSA) (See, Enright et al., 2002; Huletsky et al., 2004) serving as a negative control in the experiment shown in 2C does act as a template for RPA when combined with the primer pair orfX/mssa (FIG. 16).

REFERENCES

Amasino R. M., Acceleration of nucleic acid hybridization rate by polyethylene glycol. Anal Biochem, Volume 152, Issue 2, 304-7, Feb. 1, 1986.

Armes N. A. and Stemple D. L., Recombinase Polymerase Amplification, U.S. patent application Ser. No. 10/371,641.

Benedict R. C. and Kowalczykowski S. C. Increase in the DNA strand assimilation activity of recA protein by removal of the C terminus and structure-function studies of the resulting protein fragment. J. Biol. Chem. 1988 Oct. 25; 263(30):15513-20.

Chan E. W., Dale P. J., Greco I. L., Rose J. G., O'Connor T. E., Biochim Biophys Acta, Volume 606, Issue 2, 353-61, Feb. 29, 1980.

Edwards, A., Hammond, H. A., Jin, L., Caskey, C. T. & Chakraborty, R. Genetic variation at five trimeric and tetrameric tandem repeat loci in four human population groups. Genomics 12, 241-53 (1992).

Eggler A. L., Lusetti S. L., Cox M. M. The C terminus of the *Escherichia coli* RecA protein modulates the DNA binding competition with single-stranded DNA-binding protein. J. Biol. Chem. 2003 May 2; 278(18):16389-96.

Ellouze C., Takahashi M., Wittung P., Mortensen K., Schnarr M., Norden B. Eur. J. Biochem. 1995 Oct. 15; 233(2): 579-83.

Enright, M. C. et al. The evolutionary history of methicillin-resistant *Staphylococcus aureus* (MRSA). *Proc Natl Acad Sci USA* 99, 7687-92 (2002).

Formosa T. and Alberts B. M. Purification and characterization of the T4 bacteriophage uvsX protein. J. Biol. Chem. 1986 May 5; 261(13):6107-18.

Giedroc D. P., Gin H. W., Khan R., King G. C., Chen K. Zn(II) coordination domain mutants of T4 gp32 protein. Biochemistry. 1992 Jan. 28; 31(3):765-74.

Giedroc D. P., Keating K. M., Williams K. R., and Coleman J. E. The function of zinc in gene 32 protein from T4. Biochemistry 1987 Aug. 25; 26(17):5251-9.

Hammond, H. A., Jin, L., Zhong, Y., Caskey, C. T. & Chakraborty, R. Evaluation of 13 short tandem repeat loci for use in personal identification applications. *Am J Hum Genet.* 55, 175-89 (1994).

Harris, L. D. & Griffith, J. D. Formation of D loops by the UvsX protein of T4 bacteriophage: a comparison of the reaction catalyzed in the presence or absence of gene 32 protein. Biochemistry 27, 6954-9 (1988).

Harris, L. D. & Griffith, J. D. UvsY protein of bacteriophage T4 is an accessory protein for in vitro catalysis of strand exchange. *J Mol Biol* 206, 19-27 (1989).

Huletsky, A. et al. New real-time PCR assay for rapid detection of methicillinresistant *Staphylococcus aureus* directly from specimens containing a mixture of staphylococci. *J Clin Microbiol* 42, 1875-84 (2004).

Ischenko A A, Saparbaev M K. Alternative nucleotide incision repair pathway for oxidative DNA damage. Nature 2002 Jan. 10; 415(6868):183-7.

Kaiser M W, Lyamicheva N, Ma W, Miller C, Neri B, Fors L, Lyamichev V I. A comparison of eubacterial and archaeal structure-specific 5'-exonucleases. J Biol. Chem. 1999 Jul. 23; 274(30):21387-94.

Kuil M E, van der Oord C J, Vlaanderen C A, van Haeringen B, van Grondelle R. A refined calculation of the solution dimensions of the complex between gene 32 protein and single stranded DNA based on estimates of the bending persistence length. J Biomol Struct Dyn. 1990 February; 7(4):943-57.

Lavery P. E. and Kowalczykowski S. C., J. Biol. Chem., Vol. 267, Issue 13, 9307-14, May 5, 1992.

Lerman L. S., A transition to a Compact Form of DNA in Polymer Solutions. Proc Natl Acad Sci USA. 1971 April; 68(8):1886-1890.

Levin, J. D., Johnson, A. W. & Demple, B. Homogeneous *Escherichia coli* endonuclease IV. Characterization of an enzyme that recognizes oxidative damage in DNA. *J Biol Chem* 263, 8066-71 (1988).

Lusetti S. L., Shaw J. J., Cox M. M. Magnesium ion-dependent activation of the RecA protein involves the C terminus. J. Biol. Chem. 2003 May 2; 278(18):16389-96.

Malkov V. A. and Camerini-Otero R. D. Photocross-links between single-stranded DNA and *Escherichia coli* RecA protein map to loops L1 (amino acid residues 157-164) and L2 (amino acid residues 195-209). J. Biol. Chem. 1995 Dec. 15, Volume 270, Issue 50, 30230-3.

Minton A. P. The Influence of Macromolecular Crowding and Macromolecular Confinement on Biochemical Reactions in Physiological Media. J. Biol. Chem., Vol. 276, Issue 14, 10577-10580, Apr. 6, 2001.

Morrison, T. B., Weis, J. J. & Wittwer, C. T. Quantification of low-copy transcripts by continuous SYBR Green I monitoring during amplification. *Biotechniques* 24, 954-8, 960, 962 (1998).

Nadler S. G., Roberts W. J., Shamoo Y., Williams K. R. A novel function for Zinc(II) in a nucleic acid-binding protein. Contribution of Zinc(II) toward the cooperativity of bacteriophage T4 gp32 protein binding. J. Biol. Chem. 1990 Jun. 25; 265(18):10389-94.

Naimushin A. N., Quach M., Fujimoto B. S., Schurr J. M. Effect of polyethylene glycol on the supercoiling free energy of DNA. Biopolymers. 2001, Volume 58, Issue 2, 204-17.

Okazaki, T. & Kornberg, A. Enzymatic Synthesis of Deoxyribonucleic Acid. Xv. Purification and Properties of a Polymerase from *Bacillus Subtilis*. *J Biol Chem* 239, 259-68 (1964).

Qiu H. and Giedroc D. P. Effects of substitution of proposed Zn(II) ligand His81 or His64 in phage gp32 protein: spectroscopic evidence for a novel zinc coordination complex. Biochemistry 1994 Jul. 5; 33(26):8139-48.

Rivas G., Ferrone F., Herzfeld J. Life in a crowded world—Workshop on the Biological Implications of Macromolecular Crowding. EMBO reports 5, 1, 23-27 (2004) doi:10.1038/sj.embor.7400056 Published online: 19 Dec. 2003.

Savva, R. and Pearl, L. H. Cloning and expression of the uracil-DNA glycosylase inhibitor (UGI) from bacteriophage PBS-1 and crystallization of a uracil-DNA glycosylase-UGI complex, Proteins 22 (3), 287-289 (1995).

Scheerhagen M A, Kuil M E, van Grondelle R, Blok J. Hydrodynamic studies of a DNA-protein complex. Dimensions of the complex of single-stranded 145 base DNA with gene 32 protein of phage T4 deduced from quasi-elastic light scattering. FEBS Lett. 1985 May 20; 184(2):221-5.

Shibata, T., Cunningham, R. P., DasGupta, C. & Radding, C. M. Homologous pairing in genetic recombination: complexes of recA protein and DNA. *Proc Natl Acad Sci USA* 76, 5100-4 (1979).

Story R. M., Bishop D. K., Kleckner N., Steitz, T. A. Structural relationship of bacterial RecA proteins to recombination proteins from bacteriophage T4 and yeast. Science. 1993 Mar. 26, 259(5103):1892-6.

Takeshita, M., Chang, C. N., Johnson, F., Will, S. & Grollman, A. P. Oligodeoxynucleotides containing synthetic abasic sites. Model substrates for DNA polymerases and apurinic/apyrimidinic endonucleases. *J Biol Chem* 262, 10171-9 (1987).

Voloshin O. N., Wang L., Camerini-Otero R. D. Homologous DNA pairing Promoted by a 20-Amino Acid Peptide Derived From RecA. Science 10 May 1996. Vol 272 Number 5263, pages 868-872.

Voloshin O. N., Wang L., Camerini-Otero R. D. The homologous pairing domain of RecA also mediates the allosteric regulation of DNA binding and ATP hydrolysis: a remarkable concentration of functional residues. J. Mol. Biol. 2000 Nov. 10; 303(5):709-20.

Walker J. E., Saraste M., Runswick M., and Gay N. J. 1982 EMBO J. Volume 1. Pages 945-51.

Wang Z, Mosbaugh D W. Uracil-DNA glycosylase inhibitor of bacteriophage PBS2: cloning and effects of expression of the inhibitor gene in *Escherichia coli*. J. Bacteriol. 1988 March; 170(3):1082-91.

Yang S, VanLoock M S, Yu X, Egelman E H. Comparison of bacteriophage T4 UvsX and human Rad51 filaments suggests that recA-like polymerase may have evolved independently. J Mol. Biol. 2001 Oct. 5; 312(5):999-1009.

Yonesaki, T., Ryo, Y., Minagawa, T. & Takahashi, H. Purification and some of the functions of the products of bacteriophage T4 recombination genes, uvsX and uvsY. *Eur J Biochem* 148, 127-34 (1985).

Zarling, D. A., Sena E. P., Green C. J., U.S. Pat. No. 5,223,414 filed May 7, 1990.

Zimmerman S B and Harrison B. Macromolecular crowding increases binding of DNA polymerase to DNA: an adaptive effect. Proc Natl Acad Sci USA. 1987 April; 84(7): 1871-5.

Zinchenko A. A. and Yoshikawa, K. Biophysical Journal, June 2005.

The invention claimed is:

1. A composition comprising:
   (a) at least one recombinase;
   (b) at least one polymerase;
   (c) a target nucleic acid;
   (d) a first and a second nucleic acid primer; and
   (e) an extension blocked oligonucleotide which comprises an elongation blocking group at the 3' end;
      at least one internal residue non-complementary to the target nucleic acid;
      a modified internal residue selected from the group consisting of a tetrahydrofuran residue and a D-spacer; and
      a fluorophore and a quencher.

2. The composition of claim 1, further comprising a nuclease.

3. The composition of claim 2, wherein the nuclease is a DNA glycosylase or AP endonuclease.

4. The composition of claim 1, wherein the at least one internal residue is a uracil or inosine residue.

5. The composition of claim 1, wherein the elongation blocking group at the 3' end prevents polymerase extension.

6. The composition of claim 1, wherein the at least one recombinase is in contact with at least one primer.

7. The composition of claim 1, further comprising a crowding agent.

8. The composition of claim 1, further comprising a single strand binding protein and/or a recombinase loading protein.

9. The composition of claim 8, wherein the recombinase is UvsX, the single strand binding protein is gp32, and the recombinase loading protein is UvsY.

* * * * *

SEQUENCE LISTING

<160> NUMBER OF SEQ ID NOS: 96

<210> SEQ ID NO 1
<211> LENGTH: 5
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1 aaaaa                                                                    5

<210> SEQ ID NO 2

```
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 ttatt                                                                    5

<210> SEQ ID NO 3
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3 aagaa                                                                    5

<210> SEQ ID NO 4
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4 ttatt                                                                    5

<210> SEQ ID NO 5
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5 aacaa                                                                    5

<210> SEQ ID NO 6
<211> LENGTH: 5
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6 ttatt                                                                    5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      FLAG peptide

<400> SEQUENCE: 7

Asp Tyr Lys Asp Asp Asp Asp Lys
1               5

<210> SEQ ID NO 8
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: dT-Fluorescein
<220> FEATURE:
<221> NAME/KEY: modified_base
<222> LOCATION: (27)..(27)
<223> OTHER INFORMATION: G-Tetrahydrofuranyl

<400> SEQUENCE: 8
catgattgga tgaataagct gcagctg                                              27

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: dT-TAMRA
<220> FEATURE:
<221> NAME/KEY: modified_base
<222> LOCATION: (30)..(30)
<223> OTHER INFORMATION: A-Tetrahydrofuranyl

<400> SEQUENCE: 9
tgttaattga acaagtgtac agagcattta                                           30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: dT-TAMRA
<220> FEATURE:
<221> NAME/KEY: modified_base
<222> LOCATION: (30)..(30)
<223> OTHER INFORMATION: A-Tetrahydrofuranyl

<400> SEQUENCE: 10
tgttaattga gcaagtgtat agagcattta                                           30

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: dT-Fluorescein
<220> FEATURE:
<221> NAME/KEY: modified_base
<222> LOCATION: (27)..(27)
<223> OTHER INFORMATION: G-Tetrahydrofuranyl

<400> SEQUENCE: 11
```
catgattgga tgaataagct gcagctg                                          27

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tggtaaacgg aagtctggca gggtgattct cg                                    32

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
caattgtgtg tgagatgtgg ggaagctgga at                                    32

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gaggtggttc cattccctat gtcagcattt gc                                    32

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
gggtttgaga gttgtgcatt tgcttgaaaa tc                                    32

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gttgctaacc accctgtgtc tcagttttcc tac                                   33

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cgacttctac cggtcaccac acaccttctc aga            33

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaacacttgt catagtttag aacgaactaa cg              32

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagttactcc tatttacacc ttagcaatat taag            34

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ttgctggaca tggtatcaca gaagtctggg atg             33

<210> SEQ ID NO 21
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
agaaagacag acagaaaaac ccgacggata cc              32

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aaacaaaggc agatcccaag ctcttcctct tcc             33

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ataccattta cgtttgtgtg tgcatctgta agc             33

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggtggacatg ttggcttctc tctgttctta ac                          32

<210> SEQ ID NO 25
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cgttcatcga ctctgatgtc cgtgcacggt gg                          32

<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tacacagggc ttccggtgca ggtcacaggg a                           31

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
ggtggtactc gacgacgatc tcggaccctt cc                          32

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
actggcacag aacaggcact tagggaaccc                             30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
attaattgga cacaccaagg gtcaaggagg                             30

```
<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
atggtaaatt ctggtgtgga aaacctggat gg                                   32

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
taaattctgg tgtggaaaac ctggatgg                                        28

<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
attctggtgt ggaaaacctg gatgg                                           25

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ctatccaaga ttgggctaaa cgtatgaaag ca                                   32

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ccaagattgg gctaaacgta tgaaagca                                        28

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agattgggct aaacgtatga aagca                                           25
```

```
<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
gacatgttgg cttctctctg ttcttaac                                          28

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atgttggctt ctctctgttc ttaac                                             25

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gcacgtgcct gtagtctcag ctacttgc                                          28

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cgtgcctgta gtctcagcta cttgc                                             25

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
aaagctgtaa ctctaagtat cagtgtgaaa c                                      31

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctgtaactc taagtatcag tgtgaaac                                          28

<210> SEQ ID NO 42
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gtaactctaa gtatcagtgt gaaac                                           25

<210> SEQ ID NO 43
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
gttgtccagt tgcacttcgc tgcagagtac c                                    31

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gtccagttgc acttcgctgc agagtacc                                        28

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cagttgcact tcgctgcaga gtacc                                           25

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttgggcactt ggatatgatg gaactggcac                                      30

<210> SEQ ID NO 47
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
ttgggcactt ggatatgatg gaactggcac ggttgt                               36

<210> SEQ ID NO 48
<211> LENGTH: 40
```

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttgggcactt ggatatgatg gaactggcac ggttgttgcg                          40

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ttgggcactt ggatatgatg gaactggcac ggttgttgcg tccat                    45

<210> SEQ ID NO 50
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccatcttcag agaacgcttt aacagcaatc c                                   31

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cgccatcttc agagaacgct taacagcaa tccatt                               36

<210> SEQ ID NO 52
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cgccatcttc agagaacgct ttaacagcaa tccattttgc                          40

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
cgccatcttc agagaacgct ttaacagcaa tccattttgc gccag                    45

<210> SEQ ID NO 54
<211> LENGTH: 33
<212> TYPE: DNA

<213> ORGANISM: Artificial Sequence
<220> FEATURE:
<223> OTHER INFORMATION: Description of Artificial Sequence: Synthetic
oligonucleotide

<400> SEQUENCE: 54
cagtgtatct ggaaagccta caggacacca aaa                              33

<210> SEQ ID NO 55
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 55
cagtgtatct ggaaagccta caggacacca aaataacctt                       40

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 56
cagtgtatct ggaaagccta caggacacca aaataacctt aatca                 45

<210> SEQ ID NO 57
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 57
tgctttcata cgtttagccc aatcttggat ag                               32

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 58
tgctttcata cgtttagccc aatcttggat agaatattgc                       40

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 59
tgctttcata cgtttagccc aatcttggat agaatattgc tctgc                 45

<210> SEQ ID NO 60
<211> LENGTH: 32
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 60
ccagctgtgc aagagaatat tcccgctctc cg                                    32

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
cctgttgtcc agttgcactt cgctgcagag t                                     31

<210> SEQ ID NO 62
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
acggcattaa caaacgaact gattcatctg cttgg                                 35

<210> SEQ ID NO 63
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccttaatttc tccgagaact tcatattcaa gcgtc                                 35

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: dT-Fluorescein
<220> FEATURE:
<221> NAME/KEY: modified_base
<222> LOCATION: (27)..(27)
<223> OTHER INFORMATION: G-Tetrahydrofuranyl

<400> SEQUENCE: 64
catgattgga tgaataagct gcagctg                                          27

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
```
ccaagaattg aaccaacgca tgacccaagg gcaaagcgac tttgt       45

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-C
<220> FEATURE:
<221> NAME/KEY: modified_base
<222> LOCATION: (29)..(29)
<223> OTHER INFORMATION: d-SPACER

<400> SEQUENCE: 66
ccacatcaaa tgatgcgggt tgtgttaat       29

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: dT-TAMRA
<220> FEATURE:
<221> NAME/KEY: modified_base
<222> LOCATION: (30)..(30)
<223> OTHER INFORMATION: A-Tetrahydrofuranyl

<400> SEQUENCE: 67
tgttaattga acaagtgtac agagcattta       30

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: dT-TAMRA
<220> FEATURE:
<221> NAME/KEY: modified_base
<222> LOCATION: (30)..(30)
<223> OTHER INFORMATION: A-Tetrahydrofuranyl

<400> SEQUENCE: 68
tgttaattga gcaagtgtat agagcattta       30

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(26)
<223> OTHER INFORMATION: dT-Fluorescein
<220> FEATURE:
<221> NAME/KEY: modified_base

```
<222> LOCATION: (27)..(27)
<223> OTHER INFORMATION: G-Tetrahydrofuranyl

<400> SEQUENCE: 69
catgattgga tgaataagct gcagctg                                           27

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctcaaagcta gaactttgct tcactataag tattc                                  35

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ccaatatttc atatatgtaa ttcctccaca tctca                                  35

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cccaagggca aagcgacttt gtattcgtca ttggcggatc aaacg                       45

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
ccaatttgat agggcctaat ttcaactgtt agcta                                  35

<210> SEQ ID NO 74
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Biotin-C

<400> SEQUENCE: 74
ctatgtcaaa aatcatgaac ctcattactt atgat                                  35

<210> SEQ ID NO 75
<211> LENGTH: 365
```

```
<212> TYPE: DNA
<213> ORGANISM: Staphylococcus aureus

<400> SEQUENCE: 75
ttttagatat aaaccaattt gatagggcct aatttcaact gttagctact acttaagtta      60
tatgcgcaat tatcgtgata tatcttatat attgaatgaa cgtggattta atgtccacca     120
tttaacaccc tccaaattat tatctcctca tacagaattt tttagtttta cttatgatac     180
gcctctccac gcataatctt aaatgctcta tacacttgct caattaacac aacccgcatc     240
atttgatgtg ggaatgtcat tttgctgaat gatagtgcgt agttactgcg ttgtaagacg     300
tccttgtgca ggccgtttga tccgccaatg acgaatacaa agtcgctttg cccttgggtc     360
atgcg                                                                 365

<210> SEQ ID NO 76
<211> LENGTH: 333
<212> TYPE: DNA
<213> ORGANISM: Staphylococcus aureus

<400> SEQUENCE: 76
tttagttgca gaaagaattt tctcaaagct agaactttgc ttcactataa gtattcagta      60
taagaatat ttcgctatta tttacttgaa atgaaagact gcggaggcta actatgtcaa      120
aaatcatgaa cctcattact tatgataagc ttctccacgc ataatcttaa atgctctata     180
cacttgctca attaacacaa cccgcatcat ttgatgtggg aatgtcattt tgctgaatga     240
tagtgcgtag ttactgcgtt gtaagacgtc cttgtgcagg ccgtttgatc cgccaatgac     300
gaatacaaag tcgctttgcc cttgggtcat gcg                                  333

<210> SEQ ID NO 77
<211> LENGTH: 435
<212> TYPE: DNA
<213> ORGANISM: Staphylococcus aureus

<400> SEQUENCE: 77
tttagttgca gaaagaattt tctcaaagct agaactttgc ttcactataa gtattcagta      60
taagaatat ttcgctatta tttacttgaa atgaaagact gcggaggcta actatgtcaa      120
aaatcatgaa cctcattact tatgataagc ttcttaaaaa cataacagca attcacataa     180
acctcatatg ttctgataca ttcaaaatcc ctttatgaag cggctgaaaa aaccgcatca     240
tttatgatat gcttctccac gcataatctt aaatgctctg tacacttgtt caattaacac     300
aacccgcatc atttgatgtg ggaatgtcat tttgctgaat gatagtgcgt agttactgcg     360
ttgtaagacg tccttgtgca ggccgtttga tccgccaatg acgaatacaa agtcgctttg     420
cccttgggtc atgcg                                                      435

<210> SEQ ID NO 78
<211> LENGTH: 280
<212> TYPE: DNA
<213> ORGANISM: Staphylococcus aureus

<400> SEQUENCE: 78
aaggtataat ccaatatttc atatatgtaa ttcctccaca tctcattaaa ttttaaatt       60
atacacaacc taattttag ttttatttat gatacgcttc tccacgcata atcttaaatg      120
ctctgtacac ttgttcaatt aacacaaccc gcatcatttg atgtgggaat gtcattttgc     180
tgaatgatag tgcgtagtta ctgcgttgta agacgtcctt gtgcaggccg tttgatccgc     240
```

```
caatgacgaa tacaaagtcg ctttgccctt gggtcatgcg                                    280
```

```
<210> SEQ ID NO 79
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-C
<220> FEATURE:
<221> NAME/KEY: modified_base
<222> LOCATION: (29)..(29)
<223> OTHER INFORMATION: T-Tetrahydrofuranyl

<400> SEQUENCE: 79
ccacatcaaa tgatgcgggt tgtgttaat                                                29
```

```
<210> SEQ ID NO 80
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: FAM-C
<220> FEATURE:
<221> NAME/KEY: modified_base
<222> LOCATION: (29)..(29)
<223> OTHER INFORMATION: T-Tetrahydrofuranyl

<400> SEQUENCE: 80
ccacatcaaa tgatgcgggt tgtgttaat                                                29
```

```
<210> SEQ ID NO 81
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: dT-DDQ1
<220> FEATURE:
<221> NAME/KEY: modified_base
<222> LOCATION: (14)..(14)
<223> OTHER INFORMATION: A-dRbiotin

<400> SEQUENCE: 81
ttaaaggaaa ctta                                                                14
```

```
<210> SEQ ID NO 82
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: dT-BHQ1
<220> FEATURE:
<221> NAME/KEY: modified_base
```

<222> LOCATION: (14)..(14)
<223> OTHER INFORMATION: G-biotin

<400> SEQUENCE: 82
gattatgcgt ggag                                                            14

<210> SEQ ID NO 83
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: dT-BHQ2
<220> FEATURE:
<221> NAME/KEY: modified_base
<222> LOCATION: (14)..(14)
<223> OTHER INFORMATION: G-biotin

<400> SEQUENCE: 83
gattatgcgt ggag                                                            14

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: dT-DDQ1
<220> FEATURE:
<221> NAME/KEY: modified_base
<222> LOCATION: (13)..(13)
<223> OTHER INFORMATION: A-biotin

<400> SEQUENCE: 84
taaaggaaac tta                                                             13

<210> SEQ ID NO 85
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: dT-DDQ1
<220> FEATURE:
<221> NAME/KEY: modified_base
<222> LOCATION: (14)..(14)
<223> OTHER INFORMATION: A-dRbiotin

<400> SEQUENCE: 85
ttaaaggaaa ctta                                                            14

<210> SEQ ID NO 86
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 86
gaacaagtgt acagag                                                  16

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: dT-BHQ1
<220> FEATURE:
<221> NAME/KEY: modified_base
<222> LOCATION: (14)..(14)
<223> OTHER INFORMATION: G-biotin

<400> SEQUENCE: 87
gattatgcgt ggag                                                    14

<210> SEQ ID NO 88
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: dT-BHQ2
<220> FEATURE:
<221> NAME/KEY: modified_base
<222> LOCATION: (14)..(14)
<223> OTHER INFORMATION: G-biotin

<400> SEQUENCE: 88
gattatgcgt ggag                                                    14

<210> SEQ ID NO 89
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: dT-DDQ1
<220> FEATURE:
<221> NAME/KEY: modified_base
<222> LOCATION: (14)..(14)
<223> OTHER INFORMATION: A-biotin

<400> SEQUENCE: 89
ttaaaggaaa ctta                                                    14

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Dideoxycytidine
```

<400> SEQUENCE: 90
gaacaagtgt acagagc                                                     17

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Dideoxycytidine

<400> SEQUENCE: 91
gagcaagtgt atagagc                                                     17

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 92

His His His His His His
1               5

<210> SEQ ID NO 93
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (30)..(30)
<223> OTHER INFORMATION: A-Tetrahydrofuranyl

<400> SEQUENCE: 93
tgttaattga acaagtgtac agagcattta                                       30

<210> SEQ ID NO 94
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
gattatgcgt ggag                                                        14

<210> SEQ ID NO 95
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
ccacatcaaa tgatgcgggt tgtgttaat                                        29

```
<210> SEQ ID NO 96
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: Dideoxycytidine

<400> SEQUENCE: 96
gaacaagtgt acagagc                                                    17
```